(12) United States Patent
Ferrari et al.

(10) Patent No.: US 9,523,088 B2
(45) Date of Patent: Dec. 20, 2016

(54) MODIFIED PROTEASES

(71) Applicant: Danisco US Inc., Palo Alto, CA (US)

(72) Inventors: Eugenio Ferrari, San Francisco, CA (US); David A. Estell, San Francisco, CA (US)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 14/305,884

(22) Filed: Jun. 16, 2014

(65) Prior Publication Data

US 2014/0295526 A1  Oct. 2, 2014

Related U.S. Application Data

(62) Division of application No. 12/047,157, filed on Mar. 12, 2008, now Pat. No. 8,779,112.

(60) Provisional application No. 60/906,734, filed on Mar. 12, 2007.

(51) Int. Cl.
*C12N 9/54* (2006.01)
*C12N 15/00* (2006.01)

(52) U.S. Cl.
CPC ......... *C12N 9/54* (2013.01); *C12Y 304/21062* (2013.01)

(58) Field of Classification Search
None
See application file for complete search history.

(56) References Cited

U.S. PATENT DOCUMENTS

| | | |
|---|---|---|
| 4,302,544 A | 11/1981 | Young et al. |
| 4,450,235 A | 5/1984 | Dean et al. |
| 4,760,025 A | 7/1988 | Estell et al. |
| 4,914,031 A | 4/1990 | Zukowski et al. |
| 4,980,288 A | 12/1990 | Bryan et al. |
| 5,208,158 A | 5/1993 | Bech et al. |
| 5,264,366 A | 11/1993 | Ferrari et al. |
| RE34,606 E | 5/1994 | Estell et al. |
| 5,310,675 A | 5/1994 | Estell et al. |
| 5,336,611 A | 8/1994 | van Eekelen et al. |

(Continued)

FOREIGN PATENT DOCUMENTS

| | | |
|---|---|---|
| EP | 0 134 048 A1 | 3/1985 |
| JP | 2004-187669 | 7/2004 |

(Continued)

OTHER PUBLICATIONS

Nakamura, T., et al., 1992, "Nucleotide sequence of the subtilisin NAT gene, aprN, of Bacillus subtilis (natto)", Bioscience, Biotechnology, and Biochemistry, vol. 56, No. 11, pp. 1869-1871.*

(Continued)

*Primary Examiner* — Nashaat Nashed
*Assistant Examiner* — William W Moore
(74) *Attorney, Agent, or Firm* — Danisco US Inc.

(57) ABSTRACT

This invention relates to modified polynucleotides encoding modified proteases, and methods for altering the production of proteases in microorganisms. In particular, the present invention relates to methods for altering the expression of proteases in microorganisms, such as *Bacillus* species. The invention discloses modified polynucleotides, vectors, modified polypeptides, and processes for enhancing the production of proteases.

13 Claims, 11 Drawing Sheets

(56) References Cited

U.S. PATENT DOCUMENTS

| | | | |
|---|---|---|---|
| 5,399,283 A | 3/1995 | Stabinsky et al. | |
| 5,441,882 A | 8/1995 | Estell et al. | |
| 5,482,849 A | 1/1996 | Branner et al. | |
| 5,631,217 A | 5/1997 | Branner et al. | |
| 5,665,587 A | 9/1997 | Aaslyng et al. | |
| 5,700,676 A | 12/1997 | Bott et al. | |
| 5,741,694 A | 4/1998 | Hastrup et al. | |
| 5,858,757 A | 1/1999 | Von Der Osten et al. | |
| 5,880,080 A | 3/1999 | Amory et al. | |
| 6,197,567 B1 | 3/2001 | Aaslyng et al. | |
| 6,218,165 B1 | 4/2001 | Estell et al. | |
| 6,376,450 B1 | 4/2002 | Ghosh et al. | |
| 7,109,016 B2 * | 9/2006 | Outtrup et al. | 435/221 |
| 7,262,042 B2 | 8/2007 | Weber et al. | |
| 8,530,218 B2 * | 9/2013 | Ferrari | C12N 15/75 435/183 |
| 8,779,112 B2 * | 7/2014 | Ferrari | C12Y 304/21062 435/221 |
| 9,115,351 B2 * | 8/2015 | Ferrari | C12N 15/75 |
| 2003/0186378 A1 * | 10/2003 | Hastrup | C12N 9/54 435/69.1 |
| 2004/0241820 A1 | 12/2004 | Outtrup et al. | |
| 2005/0009167 A1 * | 1/2005 | Weber et al. | 435/221 |
| 2005/0113273 A1 | 5/2005 | Weber et al. | |
| 2006/0073559 A1 * | 4/2006 | Ferrari | C07K 14/32 435/69.1 |
| 2006/0134740 A1 * | 6/2006 | Bryan | 435/69.1 |
| 2008/0090747 A1 | 4/2008 | Augustinus et al. | |

FOREIGN PATENT DOCUMENTS

| | | |
|---|---|---|
| WO | WO 88/06624 | 9/1988 |
| WO | WO 89/06279 A1 | 7/1989 |
| WO | WO 98/55634 | 12/1998 |
| WO | WO 99/020726 A1 | 4/1999 |
| WO | WO 99/20769 A2 | 4/1999 |
| WO | WO 99/20770 A2 | 4/1999 |
| WO | WO 99/34011 A2 | 7/1999 |
| WO | WO 02/16547 A2 | 2/2002 |

OTHER PUBLICATIONS

Matsui, A., et al., 1994, "Stabilization and rational design of serine protease AprM under highly alkaline and high-temperature conditions", Applied and Environmental Microbiology, vol. 60, No. 10, pp. 3579-3584.*

Yamagata, Y., et al., 1995, "Subtilisin Sendai from alkalophilic Bacillus sp.: Molecular and enzymatic properties of the enzyme and molecular cloning and characterization of the gene, aprS", Enzyme and Microbial Technology, vol. 17, pp. 653-663.*

Yamagata, Y., et al., 1995,"The structure of subtilisin ALP I from alkalophilic Bacillus sp. NKS-21", Current Microbiology, vol. 30, pp. 201-209.*

Takami, H., et al., 2000, "Complete genome sequence of the alkaliphilic bacterium Bacillus halodurans and genomic sequence comparison with Bacillus subtilis", Nucleic Acids Research, vol. 28, pp. 4317-4331.*

Kobayashi, T., et al., 2007, "Extremely high alkaline protease from a deep-subsurface bacterium, Alkaliphilus transvaalensis", Applied Microbiology and Biotechnology, vol. 75, No. 1, pp. 71-80.*

Kobayashi, T., et al., 1992, "Functional analysis of the intramolecular chaperone. Mutational hot spots in the subtilisin pro-peptide and a second-site suppressor mutation within the subtilisin molecule", Journal of Molecular Biology, vol. 226, No. 4, 931-933.*

Shinde, U., et al., 1995, "Folding mediated by an intramolecular chaperone: Autoprocessing pathway of the precursor resolved via a substrate assisted catalysis mechanism", Journal of Molecular Biology, vol. 247, No. 3, pp. 390-395.*

Li, Y., et al., 1995, "Functional analysis of the propeptide of subtilisin E as an intramolecular chaperone for protein folding. Refolding and inhibitory abilities of propeptide mutants", The Journal of Biological Chemistry, vol. 270, No. 42, pp. 25127-25132.*

Kojima, S. et al., 1997, "The propeptide of subtilisin BPN' as a temporary inhibitor and effect of an amino acid replacement on its inhibitory activity", FEBS Letters, vol. 411, No. 1, pp. 128-132.*

Kojima, S., et al., 1998, "Tertiary structure formation in the propeptide of subtilisin BPN' by successive amino acid replacements and its close relation to function", Journal of Molecular Biology, vol. 277, No. 5, pp. 1007-1013.*

Takahashi, M., et al., 2001, "Improved autoprocessing efficiency of mutant subtilisins E with altered specificity by engineering of the pro-region", Journal of Biochemistry, vol. 130, No. 1, pp. 99-106.*

Kojima, S. et al., 2001, "Accelerated refolding of subtilisin BPN' by tertiary-structure-forming mutants of its propeptide",J. Biochemical Journal, vol. 130, pp. 471-474.*

Yabuta, Y., et al., 2003, "Folding pathway mediated by an intramolecular chaperone", The Journal of Biological Chemistry, vol. 278, No. 17, pp. 15246-15251.*

Altschul, S.F. et al. "Basic local alignment search tool." *J. Mol. Biol* 215(3): 403-410, 1990.

Arigoni, F. et al. "The SpoIIE phosphatase, the sporulation septum and the establishment of forespore-specific transcription in *Bacillus subtilis*: a reassessment." *Molecular Microbiology* 31(5): 1407-1415, 1999.

Bakhiet, N. et al. "Studies on transfection and transformation of protoplasts of *Bacillus larvae*, *Bacillus subtilis*, and *Bacillus popilliae*." *Appl. Environ. Microbiol* 49(3): 577-581, Mar. 1, 1985.

Bron, S. et al. "Plasmids." In *Molecular Biological Methods for Bacillus*, edited by C.R. Harwood et al., pp. 75-174. Chichester, England: John Wiley & Sons, 1990.

Bryan, P.N. "Protein engineering of subtilisin." *Biochimica et Biophysica Acta* 1543(2): 203-222, Dec. 29, 2000.

Caldwell, R. et al. "Correlation between *Bacillus subtilis* scoC Phenotype and Gene Expression Determined Using Microarrays for Transcriptome Analysis." *J. Bacteriol.* 183(24): 7329-7340, Dec. 15, 2001.

Chang, S. et al. "High frequency transformation of *Bacillus subtilis* protoplasts by plasmid DNA." Mol. Gen. Genet 168: 111-115, 1979.

Christianson, T. et al. "Peptide Mapping of Subtilisins as a Practical Tool for Locating Protein Sequence Errors during Extensive Protein Engineering Projects." *Analytical Biochemistry* 223(1): 119-129, Nov. 15, 1994.

Contente, S. et al. "Marker rescue transformation by linear plasmid DNA in *Bacillus subtilis.*" *Plasmid* 2(4): 555-71, Oct. 1979.

DelMar, E.G. et al. "A sensitive new substrate for chymotrypsin." *Analytical Biochemistry* 99(2): 316-320, Nov. 1, 1979.

Estell, D.A. et al. "Engineering an enzyme by site-directed mutagenesis to be resistant to chemical oxidation." *J. Biol. Chem.* 260(11): 6518-6521, Jun. 10, 1985.

Fahnestock, S.R. et al. "Expression of the staphylococcal protein A gene in *Bacillus subtilis* by gene fusions utilizing the promoter from a *Bacillus amyloliquefaciens* alpha-amylase gene." *J. Bacteriol.* 165(3): 796-804, Mar. 1, 1986.

Ferrari, E. et al. "Genetics." In *Bacillus*, edited by C.R. Harwood, pp. 57-72. Biotechnology Handbooks 2. New York: Plenum Press, 1989.

Fischer, H.-M. et al. "Introduction of plasmid pC194 into *Bacillus thuringiensis* by protoplast transformation and plasmid transfer." *Archives of Microbiology* 139(2): 213-217, Oct. 1, 1984.

Haima, P. et al. "Novel plasmid marker rescue transformation system for molecular cloning in *Bacillus subtilis* enabling direct selection of recombinants." *Molecular and General Genetics* 223(2): 185-191, 1990.

Henikoff, S. et al. "Amino Acid Substitution Matrices from Protein Blocks." *Proc. Natl. Acad. Sci. USA* 89: 10915-10919, 1992.

Hoch, J.A. et al. "Transformation and Transduction in Recombination-defective Mutants of *Bacillus subtilis.*" *J. Bacteriol.* 93(6): 1925-1937, Jun. 1, 1967.

Hoch, J.A. et al. "Chromosomal location of pleiotropic negative sporulation mutations in *Bacillus subtilis.*" *Genetics* 73(2): 215-28, Feb. 1973.

(56) References Cited

OTHER PUBLICATIONS

Holubová, I. et al. "Transfer of liposome-encapsulated plasmid DNA to *Bacillus subtilis* protoplasts and calcium-treated *Escherichia coli* cells." *Folia Microbiologica* 30(2): 97-100, 1985.
Hsia, C.Y. et al. "Active-Site Titration of Serine Proteases Using a Fluoride Ion Selective Electrode and Sulfonyl Fluoride Inhibitors." *Analytical Biochemistry* 242(2): 221-227, Nov. 15, 1996.
Ikemura, H., et al., "Requirement of Pro-sequence for the Production of Active Subtilisin E in *Escherichia coli.*" *J. Biological Chem.* 262(16): 7859-7864, 1987.
Kalisz, H.M. "Microbial proteinases." *Advances in Biochemical Engineering/Biotechnology* 36: 1-65, 1988.
Karlin, S. et al. "Applications and statistics for multiple high-scoring segments in molecular sequences." *Proc. Natl. Acad. Sci. USA* 90(12): 5873-7, Jun. 15, 1993.
Kroll, D.J. et al. "A multifunctional prokaryotic protein expression system: overproduction, affinity purification, and selective detection." *DNA Cell Biol* 12(5): 441-53, 1993.
Maddox, D.E. "Elevated serum levels in human pregnancy of a molecule immunochemically similar to eosinophil granule major basic protein." *J. Exp. Med.* 158(4): 1211-1226, 1983.
Mann, S.P. et al. "Transformation of *Bacillus* spp.: An examination of the transformation of *Bacillus* protoplasts by plasmids pUB110 and pHV33." *Current Microbiology* 13(4): 191-195, Jul. 29, 1986.
McDonald, K.O. et al. "Plasmid transformation of *Bacillus sphaericus* 1593." *Journal of General Microbiology* 130(1): 203-8, Jan. 1984.
Msadek, T. et al. "Signal transduction pathway controlling synthesis of a class of degradative enzymes in *Bacillus subtilis*: expression of the regulatory genes and analysis of mutations in *degS* and *degU.*" *J. Bacteriol.* 172(2): 824-834, Feb. 1, 1990.
Olmos, J. et al. "Effects of the *sinR* and *degU32* (Hy) mutations on the regulation of the aprE gene in *Bacillus subtilis.*" *Molecular and General Genetics* 253(5): 562-567, Feb. 4, 1997.
Palmeros, B. et al. "A family of removable cassettes designed to obtain antibiotic-resistance-free genomic modifications of *Escherichia coli* and other bacteria." *Gene* 247(1-2): 255-264, Apr. 18, 2000.
Palva, I. "Molecular cloning of alpha-amylase gene from *Bacillus amyloliquefaciens* and its expression in *B. subtilis.*" *Gene* 19(1): 81-7, Aug. 1982.
Perego, M. "Integrational vectors for genetic manipulation in *Bacillus subtilis.*" In *Bacillus subtilis and other Gram-positive bacteria: biochemistry physiology and molecular genetics*, edited by A.L. Sonenshein et al., pp. 615-624. Washington, D.C.: American Society for Microbiology, 1993.

Perego, M. et al. "The oligopeptide transport system of *Bacillus subtilis* plays a role in the initiation of sporulation." *Molecular Microbiology* 5(1): 173-85, Jan. 1991.
Porath, J. "Immobilized metal ion affinity chromatography." *Protein Expr Purif* 3(4): 263-81, 1992.
Power, S.D. et al. "Secretion and autoproteolytic maturation of subtilisin." *Proc. Natl. Acad. Sci. U.S.A* 83(10): 3096-100, May 1986.
Priest, F.G. "Extracellular enzyme synthesis in the genus Bacillus." *Bacteriological Reviews* 41(3): 711-753, Sep. 1977.
Ruan, B. et al. "Rapid foldingof calcium-free subtilism by a stabilized pro-domain mutant." *Biochemistry* 38(26) 8562-8571, Jun. 29, 1999.
Saunders, C.W. et al. "Use of chromosomal integration in the establishment and expression of *blaZ*, a *Staphylococcus aureus* beta-lactamase gene, in *Bacillus subtilis.*" *J. Bacteriol.* 157(3): 718-726, Mar. 1, 1984.
Smith, M.D. et al. "Protoplast transformation in coryneform bacteria and introduction of an α-amylase gene from *Bacillus amyloliquefaciens* into *Brevibacterium lactofermentum.*" *Appl. Enviro. Microbiol.* 51(3): 634-639, 1986.
Stahl, M.L. et al. "Replacement of the *Bacillus subtilis* subtilisin structural gene with an in vitro-derived deletion mutation." *J. Bacteriol.* 158(2): 411-418, May 1, 1984.
Van der Laan et al., 1993, GenEmbl database Accession No. BACALKPR and sequence alignment with SEQ ID No.1.
Vorobjeva, I.P. et al. "Transformation of *Bacillus megaterium* protoplasts by plasmid DNA." *FEMS Microbiology Ecology* 7(3): 261-3, 1980.
Wang, L. et al. "Engineering the Independent Folding of the Subtilisin BPN' Pro-Domain: Correlation of Pro-Domain Stability with the Rate of Subtilisin Folding." *Biochemistry* 37(9): 3165-3171, Mar. 3, 1998.
Wang, L.F. et al. "Expression and secretion of human atrial natriuretic alpha-factor in *Bacillus subtilis* using the subtilisin signal peptide." *Gene* 69(1): 39-47, Sep. 15, 1988.
Ward, O.P. "Proteinases." In *Microbial Enzymes and Biotechnology*, edited by William Fogarty, pp. 251-317. London: Applied Science Publishers, 1983.
Weinrauch, Y. et al. "Plasmid marker rescue transformation in *Bacillus subtilis.*" *J. Bacteriol.* 154(3): 1077-1087, Jun. 1, 1983.
Weinrauch, Y. et al. "Plasmid marker rescue transformation proceeds by breakage-reunion in *Bacillus subtilis.*" *J. Bacteriol.* 169(3): 1205-1211, Mar. 1, 1987.
Wells, J.A. et al. "Cloning, sequencing, and secretion of *Bacillus amyloliquefaciens* subtilisin in *Bacillus subtilis.*" *Nucl. Acids Res.* 11(22): 7911-7925, Nov. 25, 1983.
English translation of Office Action dated Apr. 7, 2015 in a Japanese counterpart application, Application No. 2009-553618.

\* cited by examiner

**Polynucleotides encoding *B. clausii* Maxacal precursor protease**

SEQ ID NO: 1
ATGAAGAAACCGTTGGGGAAAATTGTCGCAAGCACCGCACTACTCATTTCTGTTGCTTTTAG
TTCATCGATCGCATCGGCT**GCTGAAGAAGCAAAAGAAAAATATTTAATTGGCTTTAATGAGC
AGGAAGCTGTCAGTGAGTTTGTAGAACAAGTAGAGGCAAATGACGAGGTCGCCATTCTCTCT
GAGGAAGAGGAAGTCGAAATTGAATTGCTTCATGAATTTGAAACGATTCCTGTTTTATCCGT
TGAGTTAAGCCCAGAAGATGTGGACGCGCTTGAACTCGATCCAGCGATTTCTTATATTGAAG
AGGATGCAGAAGTAACGACAATG**GCGCAATCAGTGCCATGGGGAATTAGCCGTGTGCAAGCC
CCAGCTGCCCATAACCGTGGATTGACAGGTTCTGGTGTAAAAGTTGCTGTCCTCGATACAGG
TATTTCCACTCATCCAGACTTAAATATTCGTGGTGGCGCTAGCTTTGTACCAGGGGAACCAT
CCACTCAAGATGGGAATGGGCATGGCACGCATGTGGCTGGGACGATTGCTGCTTTAAACAAT
TCGATTGGCGTTCTTGGCGTAGCACCGAACGCGGAACTATACGCTGTTAAAGTATTAGGGGC
GAGCGGTTCAGGTTCGGTCAGCTCGATTGCCCAAGGATTGGAATGGGCAGGGAACAATGGCA
TGCACGTTGCTAATTTGAGTTTAGGAAGCCCTTCGCCAAGTGCCACACTTGAGCAAGCTGTT
AATAGCGCGACTTCTAGAGGCGTTCTTGTTGTAGCGGCATCTGGGAATTCAGGTGCAGGCTC
AATCAGCTATCCGGCCCGTTATGCGAACGCAATGGCAGTCGGAGCTACTGACCAAAACAACA
ACCGCGCCAGCTTTTCACAGTATGGCGCAGGGCTTGACATTGTCGCACCAGGTGTAAACGTG
CAGAGCACATACCCAGGTTCAACGTATGCCAGCTTAAACGGTACATCGATGGCTACTCCTCA
TGTTGCAGGTGCAGCAGCCCTTGTTAAACAAAAGAACCCATCTTGGTCCAATGTACAAATCC
GCAATCATCTAAAGAATACGGCAACGAGCTTAGGAAGCACGAACTTGTATGGAAGCGGACTT
GTCAATGCAGAAGCGGCAACACGCTAA

*FIG. 1A*

SEQ ID NO: 2
ATGAAGAAACCGTTGGGGAAAATTGTCGCAAGCACCGCACTACTCATTTCTGTTGCTTTTAG
TTCATCGATCGCATCGGCT

*FIG. 1B*

SEQ ID NO: 3
GCTGAAGAAGCAAAAGAAAAATATTTAATTGGCTTTAATGAGCAGGAAGCTGTCAGTGAGTT
TGTAGAACAAGTAGAGGCAAATGACGAGGTCGCCATTCTCTCTGAGGAAGAGGAAGTCGAAA
TTGAATTGCTTCATGAATTTGAAACGATTCCTGTTTTATCCGTTGAGTTAAGCCCAGAAGAT
GTGGACGCGCTTGAACTCGATCCAGCGATTTCTTATATTGAAGAGGATGCAGAAGTAACGACAATG

*FIG. 1C*

SEQ ID NO: 4
GCGCAATCAGTGCCATGGGGAATTAGCCGTGTGCAAGCCCCAGCTGCCCATAACCGTGGATT
GACAGGTTCTGGTGTAAAAGTTGCTGTCCTCGATACAGGTATTTCCACTCATCCAGACTTAA
ATATTCGTGGTGGCGCTAGCTTTGTACCAGGGGAACCATCCACTCAAGATGGGAATGGGCAT
GGCACGCATGTGGCTGGGACGATTGCTGCTTTAAACAATTCGATTGGCGTTCTTGGCGTAGC
ACCGAACGCGGAACTATACGCTGTTAAAGTATTAGGGGCGAGCGGTTCAGGTTCGGTCAGCT
CGATTGCCCAAGGATTGGAATGGGCAGGGAACAATGGCATGCACGTTGCTAATTTGAGTTTA
GGAAGCCCTTCGCCAAGTGCCACACTTGAGCAAGCTGTTAATAGCGCGACTTCTAGAGGCGT
TCTTGTTGTAGCGGCATCTGGGAATTCAGGTGCAGGCTCAATCAGCTATCCGGCCCGTTATG
CGAACGCAATGGCAGTCGGAGCTACTGACCAAAACAACAACCGCGCCAGCTTTTCACAGTAT
GGCGCAGGGCTTGACATTGTCGCACCAGGTGTAAACGTGCAGAGCACATACCCAGGTTCAAC
GTATGCCAGCTTAAACGGTACATCGATGGCTACTCCTCATGTTGCAGGTGCAGCAGCCCTTG
TTAAACAAAAGAACCCATCTTGGTCCAATGTACAAATCCGCAATCATCTAAAGAATACGGCA
ACGAGCTTAGGAAGCACGAACTTGTATGGAAGCGGACTTGTCAATGCAGAAGCGGCAACACGCTAA

FIG. 1D

Amino acid sequences of *B. clausii* Maxacal precursor protease
SEQ ID NO: 5
MKKPLGKIVASTALLISVAFSSSIAS**AAEEAKEKYLIGFNEQEAVSEFVEQVEANDEVAILS
EEEEVEIELLHEFETIPVLSVELSPEDVDALELDPAISYIEEDAEVTTM**RVQAPAAHNRGLT
GSGVKVAVLDTGISTHPDLNIRGGASFVPGEPSTQDGNHGTHVAGTIAALNNSIGVLGVAP
NAELYAVKVLGASGSGSVSSIAQGLEWAGNNGMHVANLSLGSPSPSATLEQAVNSATSRGVL
VVAASGNSGAGSISYPARYANAMAVGATDQNNNRASFSQYGAGLDIVAPGVNVQSTYPGSTY
ASLNGTSMATPHVAGAAALVKQKNPSWSNVQIRNHLKNTATSLGSTNLYGSGLVNAEAATR

FIG. 2A

SEQ ID NO: 6
MKKPLGKIVASTALLISVAFSSSIASA

FIG. 2B

SEQ ID NO: 7
AEEAKEKYLIGFNEQEAVSEFVEQVEANDEVAILSEEEEVEIELLHEFETIPVLSVELSPED
VDALELDPAISYIEEDAEVTTM

FIG. 2C

SEQ ID NO: 8
RVQAPAAHNRGLTGSGVKVAVLDTGISTHPDLNIRGGASFVPGEPSTQDGNHGTHVAGTIA
ALNNSIGVLGVAPNAELYAVKVLGASGSGSVSSIAQGLEWAGNNGMHVANLSLGSPSPSATL
EQAVNSATSRGVLVVAASGNSGAGSISYPARYANAMAVGATDQNNNRASFSQYGAGLDIVAP
GVNVQSTYPGSTYASLNGTSMATPHVAGAAALVKQKNPSWSNVQIRNHLKNTAT
SLGSTNLYGSGLVNAEAATR

FIG. 2D

Polynucleotides encoding *B. clausii* 049 precursor protease

SEQ ID NO: 9

GTGAGAAGCAAAAAATTGTGGATCGTCGCGTCGACCGCACTACTCATTTCTGTTGCTTTTAG
TTCATCGATCGCATCGGCT**GCTGAAGAAGCAAAAGAAAAATATTTAATTGGCTTTAATGAGC
AGGAAGCTGTCAGTGAGTTTGTAGAACAAGTAGAGGCAAATGACGAGGTCGCCATTCTCTCT
GAGGAAGAGGAAGTCGAAATTGAATTGCTTCATGAATTTGAAACGATTCCTGTTTTATCCGT
TGAGTTAAGCCCAGAAGATGTGGACGCGCTTGAACTCGATCCAGCGATTTCTTATATTGAAG
AGGATGCAGAAGTAACGACAATG**GCGCAATCGGTACCATGGGGAATTAGCCGTGTGCAAGCC
CCAGCTGCCCATAACCGTGGATTGACAGGTTCTGGTGTAAAAGTTGCTGTCCTCGATACAGG
TATTTCCACTCATCCAGACTTAAATATTCGTGGTGGCGCTAGCTTTGTACCAGGGGAACCAT
CCACTCAAGATGGGAATGGGCATGGCACGCATGTGGCTGGACGATTGCTGCTTTAAACAAT
TCGATTGGCGTTCTTGGCGTAGCACCGAACGCGGAACTATACGCTGTTAAAGTATTAGGGGC
GAGCGGTTCAGGTTCGGTCAGCTCGATTGCCCAAGGATTGGAATGGGCAGGGAACAATGTTA
TGCACGTTGCTAATTTGAGTTTAGGACTGCAGGCACCAAGTGCCACACTTGAGCAAGCTGTT
AATAGCGCGACTTCTAGAGGCGTTCTTGTTGTAGCGGCATCTGGGAATTCAGGTGCAGGCTC
AATCAGCTATCCGGCCCGTTATGCGAACGCAATGGCAGTCGGAGCTACTGACCAAAACAACA
ACCGCGCCAGCTTTTCACAGTATGGCGCAGGGCTTGACATTGTCGCACCAGGTGTAAACGTG
CAGAGCACATACCCAGGTTCAACGTATGCCAGCTTAAACGGTACATCGATGGCTACTCCTCA
TGTTGCAGGTGCAGCAGCCCTTGTTAAACAAAAGAACCCATCTTGGTCCAATGTACAAATCC
GCAATCATCTAAAGAATACGGCAACGAGCTTAGGAAGCACGAACTTGTATGGAAGCGGACTT
GTCAATGCAGAAGCGGCAACACGTTAA

FIG. 3A

SEQ ID NO: 10

GTGAGAAGCAAAAAATTGTGGATCGTCGCGTCGACCGCACTACTCATTTCTGTTGCTTTTAG
TTCATCGATCGCATCGGCT

FIG. 3B

SEQ ID NO: 11

GCTGAAGAAGCAAAAGAAAAATATTTAATTGGCTTTAATGAGCAGGAAGCTGTCAGTGAGTT
TGTAGAACAAGTAGAGGCAAATGACGAGGTCGCCATTCTCTCTGAGGAAGAGGAAGTCGAAA
TTGAATTGCTTCATGAATTTGAAACGATTCCTGTTTTATCCGTTGAGTTAAGCCCAGAAGAT
GTGGACGCGCTTGAACTCGATCCAGCGATTTCTTATATTGAAGAGGATGCAGAAGTAACGAC
AATG

FIG. 3C

SEQ ID NO: 12
```
GCGCAATCGGTACCATGGGGAATTAGCCGTGTGCAAGCCCCAGCTGCCCATAACCGTGGATT
GACAGGTTCTGGTGTAAAAGTTGCTGTCCTCGATACAGGTATTTCCACTCATCCAGACTTAA
ATATTCGTGGTGGCGCTAGCTTTGTACCAGGGGAACCATCCACTCAAGATGGGAATGGGCAT
GGCACGCATGTGGCTGGGACGATTGCTGCTTTAAACAATTCGATTGGCGTTCTTGGCGTAGC
ACCGAACGCGGAACTATACGCTGTTAAAGTATTAGGGGCGAGCGGTTCAGGTTCGGTCAGCT
CGATTGCCCAAGGATTGGAATGGGCAGGGAACAATGTTATGCACGTTGCTAATTTGAGTTTA
GGACTGCAGGCACCAAGTGCCACACTTGAGCAAGCTGTTAATAGCGCGACTTCTAGAGGCGT
TCTTGTTGTAGCGGCATCTGGGAATTCAGGTGCAGGCTCAATCAGCTATCCGGCCCGTTATG
CGAACGCAATGGCAGTCGGAGCTACTGACCAAAACAACAACCGCGCCAGCTTTTCACAGTAT
GGCGCAGGGCTTGACATTGTCGCACCAGGTGTAAACGTGCAGAGCACATACCCAGGTTCAAC
GTATGCCAGCTTAAACGGTACATCGATGGCTACTCCTCATGTTGCAGGTGCAGCAGCCCTTG
TTAAACAAAAGAACCCATCTTGGTCCAATGTACAAATCCGCAATCATCTAAAGAATACGGCA
ACGAGCTTAGGAAGCACGAACTTGTATGGAAGCGGACTTGTCAATGCAGAAGCGGCAACACG
TTAA
```

FIG. 3D

Amino acid sequences of *B. clausii* 049 precursor protease

SEQ ID NO: 13
VRSKKLWIVASTALLISVAFSSSIASA**AEEAKEKYLIGFNEQEAVSEFVEQVEANDEVAILS
EEEEVEIELLHEFETIPVLSVELSPEDVDALELDPAISYIEEDAEVTTM**AQSVPWGISRVQA
PAAHNRGLTGSGVKVAVLDTGISTHPDLNIRGGASFVPGEPSTQDGNGHGTHVAGTIAALNN
SIGVLGVAPNAELYAVKVLGASGSGSVSSIAQGLEWAGNNVMHVANLSLGLQAPSATLEQAV
NSATSRGVLVVAASGNSGAGSISYPARYANAMAVGATDQNNNRASFSQYGAGLDIVAPGVNV
QSTYPGSTYASLNGTSMATPHVAGAAALVKQKNPSWSNVQIRNHLKNTATSLGSTNLYGSGL
VNAEAATR

FIG. 4A

SEQ ID NO: 14
VRSKKLWIVASTALLISVAFSSSIASA

FIG. 4B

SEQ ID NO: 15
AEEAKEKYLIGFNEQEAVSEFVEQVEANDEVAILSEEEEVEIELLHEFETIPVLSVELSPED
VDALELDPAISYIEEDAEVTTM

FIG. 4C

SEQ ID NO: 16
AQSVPWGISRVQAPAAHNRGLTGSGVKVAVLDTGISTHPDLNIRGGASFVPGEPSTQDGNGH
GTHVAGTIAALNNSIGVLGVAPNAELYAVKVLGASGSGSVSSIAQGLEWAGNNVMHVANLSL
GLQAPSATLEQAVNSATSRGVLVVAASGNSGAGSISYPARYANAMAVGATDQNNNRASFSQY
GAGLDIVAPGVNVQSTYPGSTYASLNGTSMATPHVAGAAALVKQKNPSWSNVQIRNHLKNTA
TSLGSTNLYGSGLVNAEAATR

FIG. 4D

Alignment of polypeptide sequences of SEQ ID NO:5 (Maxacal),
SEQ ID NO:13 (V049) and SEQ ID NO:244 (GG36)

```
                  1                                                 50
    V049    (1)   MRSKKLWIVASTALLISVAFSSSIASAAEEAKEKYLIGFNEQEAVSEFVE
    GG36    (1)   MRSKKLWIVASTALLISVAFSSSIASAAEEAKEKYLIGFNEQEAVSEFVE
 Maxacal    (1)   MKKPLGKIVASTALLISVAFSSSIASAAEEAKEKYLIGFNEQEAVSEFVE 51                                                100
    V049   (51)   QVEANDEVAILSEEEEVEIELLHEFETIPVLSVELSPEDVDALELDPAIS
    GG36   (51)   QVEANDEVAILSEEEEVEIELLHEFETIPVLSVELSPEDVDALELDPAIS
 Maxacal   (51)   QVEANDEVAILSEEEEVEIELLHEFETIPVLSVELSPEDVDALELDPAIS 101                                               150
    V049  (101)   YIEEDAEVTTMAQSVPWGISRVQAPAAHNRGLTGSGVKVAVLDTGISTHP
    GG36  (101)   YIEEDAEVTTMAQSVPWGISRVQAPAAHNRGLTGSGVKVAVLDTGISTHP
 Maxacal  (101)   YIEEDAEVTTMAQSVPWGISRVQAPAAHNRGLTGSGVKVAVLDTGISTHP 151                                               200
    V049  (151)   DLNIRGGASFVPGEPSTQDGNGHGTHVAGTIAALNNSIGVLGVAPNAELY
    GG36  (151)   DLNIRGGASFVPGEPSTQDGNGHGTHVAGTIAALNNSIGVLGVAPSAELY
 Maxacal  (151)   DLNIRGGASFVPGEPSTQDGNGHGTHVAGTIAALNNSIGVLGVAPNAELY 201                                               250
    V049  (201)   AVKVLGASGSGSVSSIAQGLEWAGNNVMHVANLSLGLQAPSATLEQAVNS
    GG36  (201)   AVKVLGASGSGSVSSIAQGLEWAGNNGMHVANLSLGSPSPSATLEQAVNS
 Maxacal  (201)   AVKVLGASGSGSVSSIAQGLEWAGNNGMHVANLSLGSPSPSATLEQAVNS 251                                               300
    V049  (251)   ATSRGVLVVAASGNSGAGSISYPARYANAMAVGATDQNNNRASFSQYGAG
    GG36  (251)   ATSRGVLVVAASGNSGAGSISYPARYANAMAVGATDQNNNRASFSQYGAG
 Maxacal  (251)   ATSRGVLVVAASGNSGAGSISYPARYANAMAVGATDQNNNRASFSQYGAG 301                                               350
    V049  (301)   LDIVAPGVNVQSTYPGSTYASLNGTSMATPHVAGAAALVKQKNPSWSNVQ
    GG36  (301)   LDIVAPGVNVQSTYPGSTYASLNGTSMATPHVAGAAALVKQKNPSWSNVQ
 Maxacal  (301)   LDIVAPGVNVQSTYPGSTYASLNGTSMATPHVAGAAALVKQKNPSWSNVQ 351                      381
    V049  (351)   IRNHLKNTATSLGSTNLYGSGLVNAEAATR-  (SEQ ID NO: 13)
    GG36  (351)   IRNHLKNTATSLGSTNLYGSGLVNAEAATR-  (SEQ ID NO: 244)
 Maxacal  (351)   IRNHLKNTATSLGSTNLYGSGLVNAEAATR-  (SEQ ID NO: 5)
```

FIG. 5

Polynucleotide Sequence of pXX-049 Plasmid

SEQ ID NO: 17

AATTCCTCCATTTTCTTCTGCTATCAAAATAACAGACTCGTGATTTTCCAAACGAGCTTTCA
AAAAAGCCTCTGCCCCTTGCAAATCGGATGCCTGTCTATAAAATTCCCGATATTGGCTTAAA
CAGCGGCGCAATGGCGGCCGCATCTGATGTCTTTGCTTGGCGAATGTTCATCTTATTTCTTC
CTCCCTCTCAATAATTTTTTCATTCTATCCCTTTTCTGTAAAGTTTATTTTTCAGAATACTT
TTATCATCATGCTTTGAAAAAATATCACGATAATATCCATTGTTCTACGGAAGCACACGCA
GGTCATTTGAACGAATTTTTTCGACAGGAATTTGCCGGGACTCAGGAGCATTTAACCTAAAA
AAGCATGACATTTCAGCATAATGAACATTTACTCATGTCTATTTTCGTTCTTTTCTGTATGA
AAATAGTTATTTCGAGTCTCTACGGAAATAGCGAGAGATGATATACCTAAATAGAGATAAAA
TCATCTCAAAAAAATGGGTCTACTAAAATATTATTCCATCTATTACAATAAATTCACAGAAT
AGTCTTTTAAGTAAGTCTACTCTGAATTTTTTTAAAAGGAGAGGGTAAAGAGTGAGAAGCAA
AAAATTGTGGATCGTCGCGTCGACCGCACTACTCATTTCTGTTGCTTTTAGTTCATCGATCG
CATCGGCTGCTGAAGAAGCAAAAGAAAAATATTTAATTGGCTTTAATGAGCAGGAAGCTGTC
AGTGAGTTTGTAGAACAAGTAGAGGCAAATGACGAGGTCGCCATTCTCTCTGAGGAAGAGGA
AGTCGAAATTGAATTGCTTCATGAATTTGAAACGATTCCTGTTTTATCCGTTGAGTTAAGCC
CAGAAGATGTGGACGCGCTTGAACTCGATCCAGCGATTTCTTATATTGAAGAGGATGCAGAA
GTAACGACAATGGCGCAATCGGTACCATGGGGAATTAGCCGTGTGCAAGCCCCAGCTGCCCA
TAACCGTGGATTGACAGGTTCTGGTGTAAAAGTTGCTGTCCTCGATACAGGTATTTCCACTC
ATCCAGACTTAAATATTCGTGGTGGCGCTAGCTTTGTACCAGGGGAACCATCCACTCAAGAT
GGGAATGGGCATGGCACGCATGTGGCTGGGACGATTGCTGCTTTAAACAATTCGATTGGCGT
TCTTGGCGTAGCACCGAACGCGGAACTATACGCTGTTAAAGTATTAGGGGCGAGCGGTTCAG
GTTCGGTCAGCTCGATTGCCCAAGGATTGGAATGGGCAGGGAACAATGTTATGCACGTTGCT
AATTTGAGTTTAGGACTGCAGGCACCAAGTGCCACACTTGAGCAAGCTGTTAATAGCGCGAC
TTCTAGAGGCGTTCTTGTTGTAGCGGCATCTGGGAATTCAGGTGCAGGCTCAATCAGCTATC
CGGCCCGTTATGCGAACGCAATGGCAGTCGGAGCTACTGACCAAAACAACAACCGCGCCAGC
TTTTCACAGTATGGCGCAGGGCTTGACATTGTCGCACCAGGTGTAAACGTGCAGAGCACATA
CCCAGGTTCAACGTATGCCAGCTTAAACGGTACATCGATGGCTACTCCTCATGTTGCAGGTG
CAGCAGCCCTTGTTAAACAAAAGAACCCATCTTGGTCCAATGTACAAATCCGCAATCATCTA
AAGAATACGGCAACGAGCTTAGGAAGCACGAACTTGTATGGAAGCGGACTTGTCAATGCAGA
AGCGGCAACACGTTAATCAATAAAAAACGCTGTGCGGTTAAAGGGCACAGCGTTTTTTTGT
GTATGAATCGGGATCCTCGATCGAGACTAGAGTCGATTTTTACAAGAATTAGCTTTATATAA
TTTCTGTTTTTCTAAAGTTTTATCAGCTACAAAAGACAGAAATGTATTGCAATCTTCAACTA
AATCCATTTGATTCTCTCCAATATGACGTTTAATAAATTTCTGAAATACTTGATTTCTTTGT
TTTTTCTCAGTATACTTTTCCATGTTATAACACATAAAAACAACTTAGTTTTCACAAACTAT
GACAATAAAAAAGTTGCTTTTTCCCCTTTCTATGTATGTTTTTACTAGTCATTTAAAACG
ATACATTAATAGGTACGAAAAAGCAACTTTTTTTGCGCTTAAAACCAGTCATACCAATAACT
TAAGGGTAACTAGCCTCGCCGGCAATAGTTACCCTTATTATCAAGATAAGAAAGAAAAGGAT
TTTTCGCTACGCTCAAATCCTTTAAAAAAACACAAAAGACCACATTTTTTAATGTGGTCTTT
ATTCTTCAACTAAAGCACCCATTAGTTCAACAAACGAAAATTGGATAAAGTGGGATATTTTT
AAAATATATATTTATGTTACAGTAATATTGACTTTTAAAAAGGATTGATTCTAATGAAGAA
AGCAGACAAGTAAGCCTCCTAAATTCACTTTAGATAAAAATTTAGGAGGCATATCAAATGAA

*FIG. 7A*

```
CTTTAATAAAATTGATTTAGACAATTGGAAGAGAAAAGAGATATTTAATCATTATTTGAACC
AACAAACGACTTTTAGTATAACCACAGAAATTGATATTAGTGTTTTATACCGAAACATAAAA
CAAGAAGGATATAAATTTTACCCTGCATTTATTTTCTTAGTGACAAGGGTGATAAACTCAAA
TACAGCTTTTAGAACTGGTTACAATAGCGACGGAGAGTTAGGTTATTGGGATAAGTTAGAGC
CACTTTATACAATTTTTGATGGTGTATCTAAAACATTCTCTGGTATTTGGACTCCTGTAAAG
AATGACTTCAAAGAGTTTTATGATTTATACCTTTCTGATGTAGAGAAATATAATGGTTCGGG
GAAATTGTTTCCCAAAACACCTATACCTGAAATGCTTTTTCTCTTTCTATTATTCCATGGA
CTTCATTTACTGGGTTTAACTTAAATATCAATAATAATAGTAATTACCTTCTACCCATTATT
ACAGCAGGAAAATTCATTAATAAAGGTAATTCAATATATTTACCGCTATCTTTACAGGTACA
TCATTCTGTTTGTGATGGTTATCATGCAGGATTGTTTATGAACTCTATTCAGGAATTGTCAG
ATAGGCCTAATGACTGGCTTTTATAATATGAGATAATGCCGACTGTACTTTTTACAGTCGGT
TTTCTAATGTCACTAACCTGCCCCGTTAGTTGAAGAAGGTTTTTATATTACAGCTCCAGATC
CATATCCTTCTTTTTCTGAACCGACTTCTCCTTTTTCGCTTCTTTATTCCAATTGCTTTATT
GACGTTGAGCCTCGGAACCCTTAACAATCCCAAAACTTGTCGAATGGTCGGCTTAATAGCTC
ACGCTATGCCGACATTCGTCTGCAAGTTTAGTTAAGGGTTCTTCTCAACGCACAATAAATTT
TCTCGGCATAAATGCGTGGTCTAATTTTTATTTTTAATAACCTTGATAGCAAAAAATGCCAT
TCCAATACAAAACCACATACCTATAATCGACCTGCAGGAATTAATTCCTCCATTTTCTTCTG
CTATCAAAATAACAGACTCGTGATTTTCCAAACGAGCTTTCAAAAAGCCTCTGCCCCTTGC
AAATCGGATGCCTGTCTATAAAATTCCCGATATTGGCTTAAACAGCGGCGCAATGGCGGCCG
CATCTGATGTCTTTGCTTGGCGAATGTTCATCTTATTTCTTCCTCCCTCTCAATAATTTTTT
CATTCTATCCCTTTTCTGTAAAGTTTATTTTTCAGAATACTTTTATCATCATGCTTTGAAAA
AATATCACGATAATATCCATTGTTCTCACGGAAGCACACGCAGGTCATTTGAACGAATTTTT
TCGACAGGAATTTGCCGGGACTCAGGAGCATTTAACCTAAAAAGCATGACATTTCAGCATA
ATGAACATTTACTCATGTCTATTTTCGTTCTTTTCTGTATGAAAATAGTTATTTCGAGTCTC
TACGGAAATAGCGAGAGATGATATACCTAAATAGAGATAAAATCATCTCAAAAAAATGGGTC
TACTAAAATATTATTCCATCTATTACAATAAATTCACAGAATAGTCTTTTAAGTAAGTCTAC
TCTGAATTTTTTTATCAAGCTAGCTTGGCGTAATCATGGTCATAGCTGTTTCCTGTGTGAAA
TTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCG
GGAAACCTGTCGTGCCAGCTGCATTAATGAATCGGCCAACGCGCGGGGAGAGGCGGTTTGCG
TATTGGGCGCTCTTCCGCTTCCTCGCTCACTGACTCGCTGCGCTCGGTCGTTCGGCTGCGGC
GAGCGGTATCAGCTCACTCAAAGGCGGTAATACGGTTATCCACAGAATCAGGGGATAACGCA
GGAAAGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCG
TGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCG
TCTTGAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTACGGC
TACACTAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGTTTGCA
```

*FIG. 7B*

```
AGCAGCAGATTACGCGCAGAAAAAAAGGATCTCAAGAAGATCCTTTGATCTTTTCTACGGGG
TCTGACGCTCAGTGGAACGAAAACTCACGTTAAGGGATTTTGGTCATGAGATTATCAAAAAG
GATCTTCACCTAGATCCTTTTAAATTAAAAATGAAGTTTTAAATCAATCTAAAGTATATATG
AGTAAACTTGGTCTGACAGTTACCAATGCTTAATCAGTGAGGCACCTATCTCAGCGATCTGT
CTATTTCGTTCATCCATAGTTGCCTGACTCCCCGTCGTGTAGATAACTACGATACGGGAGGG
CTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCATGTTGTGCAAA
AAAGCGGTTAGCTCCTTCGGTCCTCCGATCGTTGTCAGAAGTAAGTTGGCCGCAGTGTTATC
ACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGC
TCTTGCCCGGCGTCAATACGGGATAATACCGCGCCACATAGCAGAACTTTAAAAGTGCTCAT
CATTGGAAAACGTTCTTCGGGGCGAAAACTCTCAAGGATCTTACCGCTGTTGAGATCCAGTT
CGATGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAAATG
TTGAATACTCATACTCTTCCTTTTTCAATATTATTGAAGCATTTATCAGGGTTATTGTCTCA
TGAGCGGATACATATTTGAATGTATTTAGAAAAATAAACAAATAGGGGTTCCGCGCACATTT
CCCCGAAAAGTGCCACCTGACGTCTAAGAAACCATTATTATCATGACATTAACCTATAAAAA
TAGGCGTATCACGAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAACTATGCGGCATCAGA
GCAGATTGTACTGAGAGTGCACCATATGCGGTGTGAAATACCGCACAGATGCGTAAGGAGAA
AATACCGCATCAGGCGCCATTCGCCATTCAGGCTGCGCAACTGTTGGGAAGGGCGATCGGTG
CGGGCCTCTTCGCTATTACGCCAGCTGGCGAAAGGGGGATGTGCTGCAAGGCGATTAAGTTG
GGTAACGCCAGGGTTTTCCCAGTCACGACGTTGTAAAACGACGGCCAGTG
```

FIG. 7C

**Polynucleotides encoding *B. lentus* GG36 precursor protease**

SEQ ID NO: 240

GTGAGAAGCAAAAAATTGTGGATCGTCGCGTCGACCGCACTACTCATTTCTGTTGCTTTTAG
TTCATCGATCGCATCGGCTGCTGAAGAAGCAAAAGAAAAATATTTAATTGGCTTTAATGAGC
AGGAAGCTGTCAGTGAGTTTGTAGAACAAGTAGAGGCAAATGACGAGGTCGCCATTCTCTCT
GAGGAAGAGGAAGTCGAAATTGAATTGCTTCATGAATTTGAAACGATTCCTGTTTTATCCGT
TGAGTTAAGCCCAGAAGATGTGGACGCGCTTGAACTCGATCCAGCGATTTCTTATATTGAAG
AGGATGCAGAAGTAACGACAATGGCGCAATCAGTGCCATGGGGAATTAGCCGTGTGCAAGCC
CCAGCTGCCCATAACCGTGGATTGACAGGTTCTGGTGTAAAAGTTGCTGTCCTCGATACAGG
TATTTCCACTCATCCAGACTTAAATATTCGTGGTGGCGCTAGCTTTGTACCAGGGGAACCAT
CCACTCAAGATGGGAATGGGCATGGCACGCATGTGGCCGGGACGATTGCTGCTCTAAACAAT
TCGATTGGCGTTCTTGGCGTAGCGCCGAGCGCGGAACTATACGCTGTTAAAGTATTAGGGGC
GAGCGGTTCAGGCTCGGTCAGCTCGATTGCCCAAGGATTGGAATGGGCAGGGAACAATGGCA
TGCACGTTGCTAATTTGAGTTTAGGAAGCCCTTCGCCAAGTGCCACACTTGAGCAAGCTGTT
AATAGCGCGACTTCTAGAGGCGTTCTTGTTGTAGCGGCATCTGGAAATTCAGGTGCAGGCTC
AATCAGCTATCCGGCCCGTTATGCGAACGCAATGGCAGTCGGAGCTACTGACCAAAACAACA
ACCGCGCCAGCTTTTCACAGTATGGCGCAGGGCTTGACATTGTCGCACCAGGTGTAAACGTG
CAGAGCACATACCCAGGTTCAACGTATGCCAGCTTAAACGGTACATCGATGGCTACTCCTCA
TGTTGCAGGTGCAGCAGCCCTTGTTAAACAAAAGAACCCATCTTGGTCCAATGTACAAATCC
GCAATCATCTAAAGAATACGGCAACGAGCTTAGGAAGCACGAACTTGTATGGAAGCGGACTT
GTCAATGCAGAAGCTGCAACTCGT

FIG. 8A

SEQ ID NO: 241

GTGAGAAGCAAAAAATTGTGGATCGTCGCGTCGACCGCACTACTCATTTCTGTTGCTTTTAG
TTCATCGATCGCATCGGCT

FIG. 8B

SEQ ID NO: 242

GCTGAAGAAGCAAAAGAAAAATATTTAATTGGCTTTAATGAGCAGGAAGCTGTCAGTGAGTT
TGTAGAACAAGTAGAGGCAAATGACGAGGTCGCCATTCTCTCTGAGGAAGAGGAAGTCGAAA
TTGAATTGCTTCATGAATTTGAAACGATTCCTGTTTTATCCGTTGAGTTAAGCCCAGAAGAT
GTGGACGCGCTTGAACTCGATCCAGCGATTTCTTATATTGAAGAGGATGCAGAAGTAACGAC
AATG

FIG. 8C

SEQ ID NO: 243

```
GCGCAATCAGTGCCATGGGGAATTAGCCGTGTGCAAGCCCCAGCTGCCCATAACCGTGGATT
GACAGGTTCTGGTGTAAAAGTTGCTGTCCTCGATACAGGTATTTCCACTCATCCAGACTTAA
ATATTCGTGGTGGCGCTAGCTTTGTACCAGGGGAACCATCCACTCAAGATGGGAATGGGCAT
GGCACGCATGTGGCCGGGACGATTGCTGCTCTAAACAATTCGATTGGCGTTCTTGGCGTAGC
GCCGAGCGCGGAACTATACGCTGTTAAAGTATTAGGGGCGAGCGGTTCAGGCTCGGTCAGCT
CGATTGCCCAAGGATTGGAATGGGCAGGGAACAATGGCATGCACGTTGCTAATTTGAGTTTA
GGAAGCCCTTCGCCAAGTGCCACACTTGAGCAAGCTGTTAATAGCGCGACTTCTAGAGGCGT
TCTTGTTGTAGCGGCATCTGGAAATTCAGGTGCAGGCTCAATCAGCTATCCGGCCCGTTATG
CGAACGCAATGGCAGTCGGAGCTACTGACCAAAACAACAACCGCGCCAGCTTTTCACAGTAT
GGCGCAGGGCTTGACATTGTCGCACCAGGTGTAAACGTGCAGAGCACATACCCAGGTTCAAC
GTATGCCAGCTTAAACGGTACATCGATGGCTACTCCTCATGTTGCAGGTGCAGCAGCCCTTG
TTAAACAAAAGAACCCATCTTGGTCCAATGTACAAATCCGCAATCATCTAAAGAATACGGCA
ACGAGCTTAGGAAGCACGAACTTGTATGGAAGCGGACTTGTCAATGCAGAAGCTGCAACTCGTTA
```

FIG. 8D

Amino acid sequences of *B. lentus* GG36 precursor protease

SEQ ID NO: 244

MRSKKLWIVASTALLISVAFSSSIASA**AEEAKEKYLIGFNEQEAVSEFVEQVEANDEVAILS
EEEEVEIELLHEFETIPVLSVELSPEDVDALELDPAISYIEEDAEVTTM**AQSVPWGISRVQA
PAAHNRGLTGSGVKVAVLDTGISTHPDLNIRGGASFVPGEPSTQDGNGHGTHVAGTIAALNN
SIGVLGVAPSAELYAVKVLGASGSGSVSSIAQGLEWAGNNGMHVANLSLGSPSPSATLEQAV
NSATSRGVLVVAASGNSGAGSISYPARYANAMAVGATDQNNNRASFSQYGAGLDIVAPGVNV
QSTYPGSTYASLNGTSMATPHVAGAAALVKQKNPSWSNVQIRNHLKNTATSLGSTNLYGSGL
VNAEAATR

FIG. 9A

SEQ ID NO: 245

MRSKKLWIVASTALLISVAFSSSIASA

FIG. 9B

SEQ ID NO: 246

AEEAKEKYLIGFNEQEAVSEFVEQVEANDEVAILSEEEEVEIELLHEFETIPVLSVELSPED
VDALELDPAISYIEEDAEVTTM

FIG. 9C

SEQ ID NO: 247

AQSVPWGISRVQAPAAHNRGLTGSGVKVAVLDTGISTHPDLNIRGGASFVPGEPSTQDGNGH
GTHVAGTIAALNNSIGVLGVAPSAELYAVKVLGASGSGSVSSIAQGLEWAGNNGMHVANLSL
GSPSPSATLEQAVNSATSRGVLVVAASGNSGAGSISYPARYANAMAVGATDQNNNRASFSQY
GAGLDIVAPGVNVQSTYPGSTYASLNGTSMATPHVAGAAALVKQKNPSWSNVQIRNHLKNTA
TSLGSTNLYGSGLVNAEAATR

FIG. 9D

MODIFIED PROTEASES

This application is a divisional of U.S. patent application Ser. No. 12/047,157, filed Mar. 12, 2008, and claims priority to U.S. provisional application Ser. No. 60/906,734, filed Mar. 12, 2007, both of which are herein incorporated by reference in their entirety.

REFERENCE TO A SEQUENCE LISTING

This application contains a Sequence Listing, which has been submitted via EFS, in compliance with 37 C.F.R. §1.52(e), and is hereby incorporated by reference in its entirety. The sequence listing text file submitted via EFS contains the file "30963-US-DIV_SequenceListing.txt" created on Jun. 12, 2014, which is 94,530 bytes in size.

FIELD OF THE INVENTION

This invention provides modified polynucleotides encoding modified proteases, and methods for altering the production of proteases in microorganisms. In particular, the present invention relates to methods for altering the expression of proteases in microorganisms, such as *Bacillus* species. The invention discloses modified polynucleotides, vectors, modified polypeptides, and processes for enhancing the production of proteases.

BACKGROUND

Microorganisms, such as the Gram-positive microorganism that are members of the genus *Bacillus*, have been used for large-scale industrial fermentation due, in part, to their ability to secrete their fermentation products into their culture media. Secreted proteins are exported across a cell membrane and a cell wall, and then are subsequently released into the external media. Secretion of polypeptides into periplasmic space or into their culture media is subject to a variety of parameters, which need to be carefully considered in industrial fermentations.

Indeed, secretion of heterologous polypeptides is a widely used technique in industry. Typically, cells are transformed with a nucleic acid encoding a heterologous polypeptide of interest to be expressed and secreted to produce large quantities of desired polypeptides. This technique has been used to produce large quantities of polypeptides. Expression and secretion of desired polypeptides has been controlled through genetic manipulation of the polynucleotides that encode the desired proteins. Despite various advances in protein production methods, there remains a need in the art to provide efficient methods for extracellular protein secretion.

SUMMARY OF THE INVENTION

This invention relates to modified polynucleotides encoding modified proteases, and methods for altering the production of proteases in microorganisms. In particular, the present invention relates to methods for altering the production of proteases in microorganisms, such as *Bacillus* species. The invention discloses modified polynucleotides, vectors, modified polypeptides, and processes for enhancing the production of proteases.

The present invention relates to polynucleotides, polypeptides and cells that have been genetically manipulated to enhance the production of modified proteins. In particular, the present invention relates to Gram-positive microorganisms having exogenous nucleic acid sequences introduced therein and methods for producing proteins in such host cells, such as members of the genus *Bacillus*. More specifically, the present invention relates to the production of proteases and to cells that have been genetically manipulated to have an altered capacity to produce the expressed proteins. In particular, the present invention provides for the enhanced production of proteases by a microorganism.

In some embodiments, the present invention provides for isolated modified polynucleotides encoding modified full-length proteases wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244. In some embodiments the modified full-length protease is a serine protease, wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244. In other embodiments, the full-length protease is an alkaline serine protease derived from a wild-type or variant precursor alkaline serine protease, wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244. In yet other embodiments, the full-length protease is an alkaline serine protease derived from a wild-type or variant precursor alkaline serine protease that is a *B. Clausii* or a *B. lentus* alkaline serine protease, wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244. In some embodiments, the isolated modified polynucleotide comprises the polynucleotide sequence set forth in SEQ ID NOS:1, 9 or 240.

In some embodiments, the present invention provides for isolated modified polynucleotides encoding modified full-length proteases wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244, wherein the at least one substitution is made at one amino acid position chosen from E33, E43, A44, E47, V49, E57, A59, E63, E70, E74, E84, and E88 of SEQ ID NO:5, 13 or 244. In some other embodiments, the amino acid substitution of E33 is chosen from E33D, E33I, E33S, E33N, E33K, E33H, E33Q and E33R. In yet other embodiments, the amino acid substitution of E57 is selected from E57F, E57W, E57K, E57R, E57D, E57M, E57C, E57Q, E57S, E57H and E57N.

In some embodiments, the invention provides isolated modified polynucleotides comprising a precursor pro sequence that has been mutated to encode substitutions at least at one amino acid position chosen from positions equivalent to amino acid positions 28-108 and 109 of SEQ ID NO:5, 13 or 244. In some additional embodiments, the isolated modified polynucleotides further comprise a polynucleotide encoding a full-length protease comprising a mature region, wherein the polynucleotide encodes a mature region of the protease that is at least about 70% identical to SEQ ID NOS:8, 16 or 247.

In some embodiments, the invention provides at least one vector comprising modified polynucleotides encoding modified full-length proteases wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244, or isolated modified polynucleotides comprising a precursor pro sequence that has been mutated to encode substitutions at least at one amino acid position chosen from positions equivalent to amino acid positions 28-108 and 109 of SEQ ID NO:5, 13 or 244.

In other embodiments, the invention provides a host cell that is transformed with the vector comprising the modified polynucleotides of the invention. In some preferred embodiments, the transformed host cell is a microorganism. For example, in some embodiments, the invention provides a host cell that is transformed with at least one vector comprising modified polynucleotides encoding modified full-length proteases wherein the portion of the polynucleotide sequence that encodes the pro region of the full-length precursor protease comprises mutations encoding substitutions at least at one amino acid position chosen from positions equivalent to amino acid positions 28-108 and 109 of SEQ ID NO:5, 13 and 244, or that is transformed with an isolated modified polynucleotides comprising a precursor pro sequence that has been mutated to encode substitutions at least at one amino acid position chosen from positions equivalent to amino acid positions 28-108 and 109 of SEQ ID NO:5, 13 or 244. In some embodiments, the host cell that is transformed with the polynucleotides of the invention is a microorganism is chosen from the group consisting of *Bacillus* sp., *Streptomyces* sp., *Escherichia* sp. and *Aspergillus* sp. In some other embodiments, the host cell is *B. subtilis*.

In some embodiments, the invention provides proteases produced by the transformed host cells of the invention.

The invention also provides methods for producing a heterologous protease in a microorganism, wherein the method comprises the steps of: (a) culturing a *Bacillus* host cell under suitable conditions, wherein the *Bacillus* host cell comprises a modified polynucleotide encoding a modified protease; and (b) allowing production of the protease by the microorganism. In some embodiments, the protease produced by the *Bacillus* host is recovered. Any one of the modified polynucleotides provided herein finds use in the methods of the invention.

In some embodiments, invention provides methods for producing a heterologous alkaline serine protease in a microorganism, wherein the method comprises the steps of: (a) culturing a *Bacillus* host cell under suitable conditions, wherein the *Bacillus* host cell comprises a modified polynucleotide encoding a modified protease; and (b) allowing production of the protease by the microorganism. The invention also provides methods for producing a heterologous protease in a microorganism, wherein the method comprises the steps of: (a) culturing a *Bacillus* host cell under suitable conditions, wherein the *Bacillus* host cell comprises a modified polynucleotide encoding a modified protease comprising a mature region that is at least about 70% identical to SEQ ID NOS:8, 16 or 247; and (b) allowing production of the protease by the microorganism. In some embodiments, the protease produced by the *Bacillus* host is recovered.

In some embodiments, the invention provides methods for producing a heterologous protease in a microorganism, wherein the method comprises the steps of: (a) culturing a *Bacillus* host cell under suitable conditions, wherein the *Bacillus* host cell comprises a modified polynucleotide encoding a modified protease that comprises a pro region comprising a mutation encoding a substitution at least at one amino acid position chosen from positions that are equivalent to amino acid positions 28-108 and 109 of SEQ ID NO:5, 13 or 244.; and (b) allowing production of the protease by the microorganism. In other embodiments, the at least one amino acid substitution is chosen from E33D, E33I, E33S, E33N, E33K, E33H, E33Q, E33R, E57F, E57W, E57K, E57R, E57D, E57M, E57C, E57Q, E57S, E57H and E57N.

The invention also provides methods for producing in a microorganism a heterologous protease that is a *B. clausii* or a *B. lentus* protease, wherein the method comprises the steps of: (a) culturing a *Bacillus* host cell under suitable conditions, wherein the *Bacillus* host cell comprises a modified polynucleotide encoding a modified protease; and (b) allowing production of the protease by the microorganism.

The invention also provides methods for producing a heterologous protease in a microorganism, wherein the method comprises the steps of: (a) culturing under suitable conditions a *Bacillus* host cell chosen from *B. licheniformis*, *B. lentus*, *B. subtilis*, *B. amyloliquefaciens*, *B. brevis*, *B. stearothermophilus*, *B. clausii*, *B. alkalophilus*, *B. halodurans*, *B. coagulans*, *B. circulans*, *B. pumilus*, and *B. thuringiensis*, wherein the *Bacillus* host cell comprises a modified polynucleotide encoding a modified protease; and (b) allowing production of the protease by the microorganism. In some embodiments, the host cell is a *B. subtilis* host cell.

The invention also provides methods for producing a heterologous protease in a microorganism, wherein the method comprises the steps of: (a) culturing a *Bacillus* host cell under suitable conditions, wherein the *Bacillus* host cell comprises a modified polynucleotide encoding a modified protease; and (b) allowing production of the protease by the microorganism, and wherein the heterologous protease exhibits a ratio of production of at least 1.

BRIEF DESCRIPTION OF THE DRAWINGS

FIG. 1A shows the full-length polynucleotide sequence of the wild-type protease from *B. clausii* (SEQ ID NO:1). The portion of the sequence that encodes the pro region of the protease is shown in bold letters.

FIGS. 1B, C and D show the polynucleotide sequences (SEQ ID NO:2, 3, and 4) respectively encoding the signal peptide (SEQ ID NO:6), the pro region (SEQ ID NO:7) and the mature form (SEQ ID NO:8) of the full-length *B. clausii* protease of SEQ ID NO:5.

FIG. 2A shows the full-length polypeptide sequence of the wild-type protease from *B. clausii* (SEQ ID NO:5). The portion of the sequence that encodes the pro region of the protease is shown in bold letters.

FIGS. 2B, C and D show the polypeptide sequences respectively encoding the signal peptide (SEQ ID NO:6), the pro region (SEQ ID NO:7) and the mature form (SEQ ID NO:8) of the full-length *B. clausii* protease of SEQ ID NO:5.

FIG. 3A shows the full-length polynucleotide sequence of the variant protease V049 from *B. clausii* (SEQ ID NO:9). The portion of the sequence that encodes the pro region of the protease is shown in bold letters.

FIGS. 3 B, C and D show the polynucleotide sequences (SEQ ID NO:10, 11, and 12) respectively encoding the signal peptide (SEQ ID NO:14), the pro region (SEQ ID NO:15) and the mature form (SEQ ID NO:16) of the full-length variant *B. clausii* protease of SEQ ID NO:13.

FIG. 4A shows the full-length polypeptide sequence of the variant protease V049 from *B. clausii* (SEQ ID NO:13). The portion of the sequence that encodes the pro region of the protease is shown in bold letters.

FIGS. 4B, C and D show the polypeptide sequences respectively encoding the signal peptide (SEQ ID NO:14), the pro region (SEQ ID NO:15) and the mature form (SEQ ID NO:16) of the full-length variant *B. clausii* protease of SEQ ID NO:13.

FIG. 5 shows an alignment of the amino acid sequences of the *B. clausii* wild-type serine protease of SEQ ID NO:5, the *B. clausii* variant serine protease of SEQ ID NO:13 and the *B. lentus* serine protease of SEQ ID NO:244. Differences in amino acids are underlined.

FIGS. 7A-C show the polynucleotide sequence of the pXX-V049 plasmid vector (SEQ ID NO:17) used in the present invention.

FIG. 8A shows the full-length polynucleotide sequence of the protease from *B. lentus* (SEQ ID NO:240). The portion of the sequence that encodes the pro region of the protease is shown in bold letters.

FIGS. 8B, C and D show the polynucleotide sequences (SEQ ID NO:241, 242, and 243) respectively encoding the signal peptide (SEQ ID NO:245), the pro region (SEQ ID NO:246) and the mature form (SEQ ID NO:247) of the *B. lentus* precursor protease of SEQ ID NO:244.

FIG. 9A shows the full-length polypeptide sequence of the variant protease GG36 from *B. clausii* (SEQ ID NO:244). The portion of the sequence that encodes the pro region of the protease is shown in bold letters.

FIGS. 9B, C and D show the polypeptide sequences respectively encoding the signal peptide (SEQ ID NO:245), the pro region (SEQ ID NO:246) and the mature form (SEQ ID NO:247) of the full-length *B. lentus* protease of SEQ ID NO:244.

DESCRIPTION OF THE INVENTION

Figure 6:
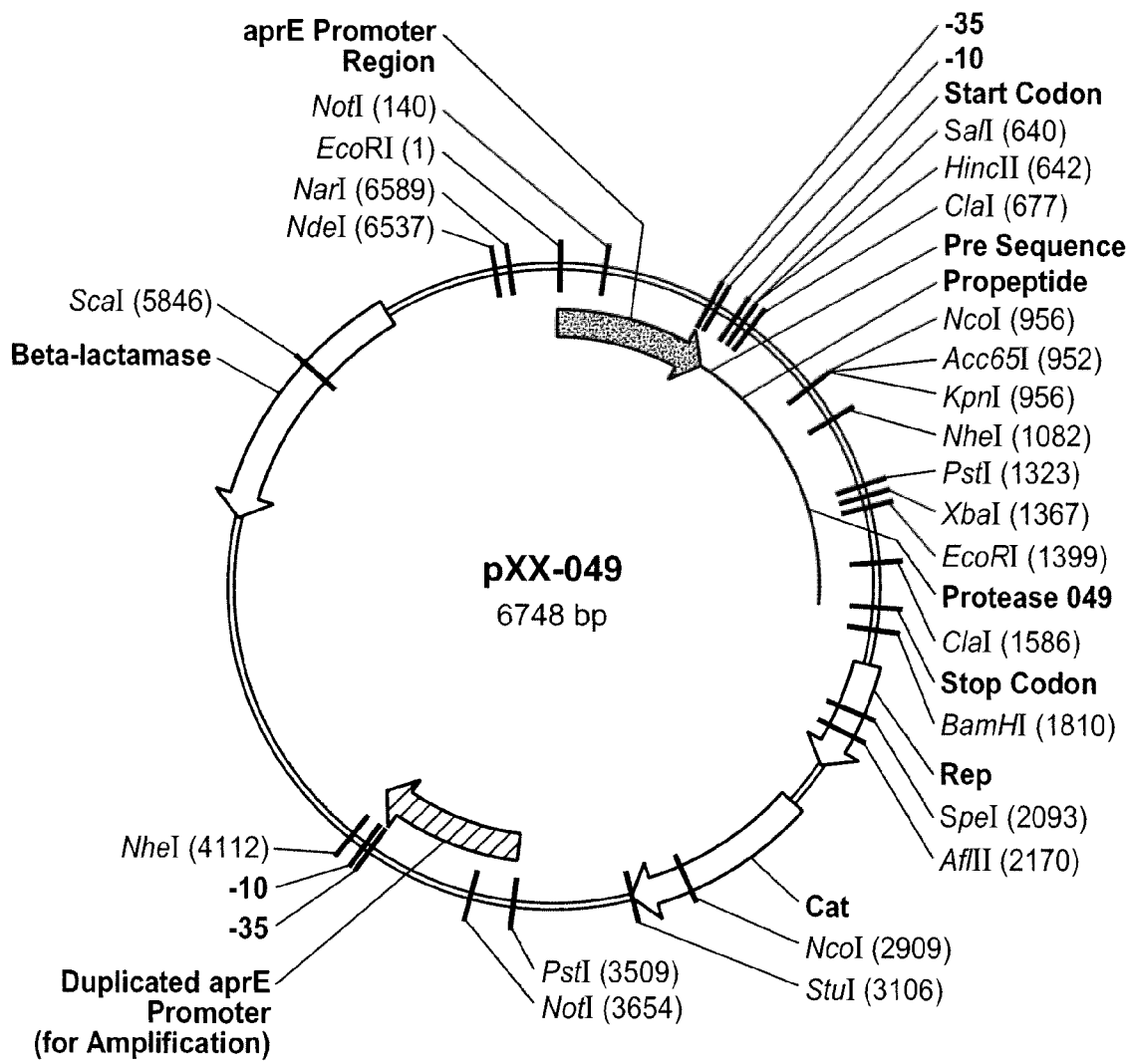
FIG. 6 provides the map of the pXX-049 plasmid vector comprising the variant serine protease of SEQ ID NO:9.

This invention relates to modified polynucleotides encoding modified proteases, and methods for altering the production of proteases in microorganisms. In particular, the present invention relates to methods for altering the production of proteases in microorganisms, such as *Bacillus* species. The invention discloses modified polynucleotides, vectors, modified polypeptides, and processes for enhancing the production of proteases.

The present invention provides modified polynucleotides encoding proteases having a mutated pro region, as well as the modified proteases encoded by the modified polynucleotides, and methods for producing the same. The modified protease polynucleotides are suitable for expressing the modified proteases in microorganisms, and processing the mature forms at levels greater than the corresponding precursor proteases. The produced proteases find use in the industrial production of enzymes, suitable for use in various industries, including but not limited to the cleaning, animal feed and textile processing industry. The present invention also provides means to produce these enzymes. In some preferred embodiments, the proteases of the present invention are in pure or relatively pure form.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Markham, The Harper Collins Dictionary of Biology, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

A "modified protease" is a full-length protease that has an amino acid sequence that is derived from the amino acid sequence of a full-length "precursor protease". The precursor protease may also be referred to as "unmodified protease". The modified protease differs from its precursor protease in the pro region. The precursor protease can be a naturally-occurring i.e. wild-type protease, or it can be a variant protease. It is the pro region of the wild-type or variant protease that is modified to generate a modified protease. The amino acid sequence of the modified protease is said to be "derived" from the precursor protease amino acid sequence by the substitution, deletion or insertion of one or more amino acids of the pro region of the precursor amino acid sequence. In preferred embodiments, one or more amino acids of the pro region of the precursor protease are substituted to generate the modified protease. Such modification is of the "precursor DNA sequence" which encodes the amino acid sequence of the precursor protease rather than manipulation of the precursor protease per se.

The modified proteases herein encompass the substitution of any of the nineteen naturally occurring amino acids at any one of the amino acid residues of the pro region of the precursor protease. In this context, both "modified" and "precursor" proteases are full-length proteases comprising a signal peptide, a pro region and a mature region. The polynucleotides that encode the modified sequence are referred to as "modified polynucleotides", and the polynucleotides that encode the precursor protease are referred to as "precursor polynucleotides". "Precursor polypeptides" and "precursor polynucleotides" can be interchangeably referred to as "unmodified precursor polypeptides" or "unmodified precursor polynucleotides", respectively.

"Naturally-occurring" or "wild-type" refers to a protease or a polynucleotide encoding a protease having the unmodified amino acid sequence identical to that found in nature. Naturally occurring enzymes include native enzymes, those enzymes naturally expressed or found in the particular microorganism. A sequence that is wild-type or naturally-occurring refers to a sequence from which a variant is derived. The wild-type sequence may encode either a homologous or heterologous protein.

As used herein, "variant" refers to a precursor protein which differs from its corresponding wild-type protein by the addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. A variant protein in the context of the present invention is exemplified by the B. clauisii protease V049 (SEQ ID NO:13), which is a variant of the naturally-occurring protein Maxacal (SEQ ID NO:5). The precursor protein of the variant can be a wild-type or variant protein.

As used herein, "equivalent to," refers to a residue at the enumerated position in a protein or peptide, or a residue that is analogous, homologous, or corresponding to an enumerated residue in a protein or peptide.

The term "production" with reference to a protease, encompasses the two processing steps of a full-length protease including: 1. the removal of the signal peptide, which is known to occur during protein secretion; and 2. the removal of the pro region, which creates the active mature form of the enzyme and which is known to occur during the maturation process (Wang et al., Biochemistry 37:3165-3171 (1998); Power et al., Proc Natl Acad Sci USA 83:3096-3100 (1986)).

The term "processed" with reference to a mature protease refers to the maturation process that a full-length protein e.g. a protease, undergoes to become an active mature enzyme.

The terms "activity ratio" and "ratio of production" are used interchangeably to refer to the ratio of the enzymatic activity of a mature protease that was processed from modified protease to the enzymatic activity of a mature protease that was processed from an unmodified protease.

The term "full-length protein" herein refers to a primary gene product of a gene and comprising a signal peptide, a pro sequence and a mature sequence.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein.

The term "pro sequence" or "pro region" is an amino acid sequence between the signal sequence and mature protease that is necessary for the secretion/production of the protease. Cleavage of the pro sequence will result in a mature active protease. To exemplify, a pro region of a protease of the present invention at least includes the amino acid sequence identical to residues 28-111 of SEQ ID NO:5, 13 or 244.

The terms "mature form" or "mature region" refer to the final functional portion of the protein. To exemplify, a mature form of the protease of the present invention at least includes the amino acid sequence identical to residues 112-380 of SEQ ID NO:5, 13 or 244. In this context, the "mature form" is "processed from" a full-length protease, wherein the processing of the full-length protease encompasses the removal of the signal peptide and the removal of the pro region.

As used herein, the term "heterologous protein" refers to a protein or polypeptide that does not naturally occur in the host cell. Similarly, a "heterologous polynucleotide" refers to a polynucleotide that does not naturally occur in the host cell.

As used herein, "homologous protein" refers to a protein or polypeptide native or naturally occurring in a cell. Similarly, a "homologous polynucleotide" refers to a polynucleotide that is native or naturally occurring in a cell.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology,* [1988]). For example, proteolytic activity may be ascertained by comparative assays which analyze the produced protease's ability to hydrolyze a commercial substrate. Exemplary substrates useful in such analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The AAPF assay (See e.g., Del Mar et al., Anal. Biochem., 99:316-320 [1979]) also finds use in determining the production of mature protease. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

The terms "polynucleotide" and "nucleic acid", used interchangeably herein, refer to a polymeric form of nucleotides of any length. These terms include, but are not limited to, a single-, double-stranded DNA, genomic DNA, cDNA, or a polymer comprising purine and pyrimidine bases, or other natural, chemically, biochemically modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., a modified sequence). In some embodiments, the sequence is operably linked to additional elements such as control elements (e.g., promoters, etc.). In some embodiments, the DNA construct comprises sequences homologous to the host cell chromosome. In other embodiments, the DNA construct comprises non-homologous sequences. Once the DNA construct is assembled in vitro it may be used to mutagenize a region of the host cell chromosome (i.e., replace an endogenous sequence with a heterologous sequence).

As used herein, the term "vector" refers to a polynucleotide construct designed to introduce nucleic acids into one or more cell types. Vectors include cloning vectors, expression vectors, shuttle vectors, and plasmids. In some embodiments, the polynucleotide construct comprises a DNA sequence encoding the full-length protease (e.g., modified protease or unmodified precursor protease).

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, [1989]).

As used herein, the terms "transformed" and "stably transformed" refers to a cell that has a non-native (heterologous)polynucleotide sequence integrated into its genome or as an episomal plasmid that is maintained for at least two generations.

The present invention provides isolated modified polynucleotides encoding amino acid sequences, encoding modified proteases. The modified proteases are obtained by mutating the polynucleotide sequence of precursor proteases. Specifically, one or more mutations of the polynucleotide sequence encoding the pro region of the precursor protease are made to provide the modified polynucleotides of the invention.

DETAILED DESCRIPTION OF THE INVENTION

This invention relates to modified polynucleotides encoding modified proteases, and methods for altering the production of proteases in microorganisms. In particular, the present invention relates to methods for altering the production of proteases in microorganisms, such as *Bacillus* species. The invention discloses modified polynucleotides, vectors, modified polypeptides, and processes for enhancing the production of proteases.

In some embodiments, the invention provides modified polynucleotides encoding modified proteases that are derived from wild-type or variant precursor proteases of animal, vegetable or microbial origin. Polynucleotides encoding precursor proteases that are derived from microorganisms are preferred, and comprise polynucleotides encoding wild-type precursor proteases and variant precursor proteases, which have been derived from the wild-type forms. In some embodiments, the modified polynucleotides of the invention are derived from polynucleotides encoding precursor proteases of microbial origin. The invention also encompasses polynucleotides encoding modified proteases that are derived from polynucleotides encoding protein engineered precursors. Polynucleotides encoding serine proteases are the preferred precursor protease polynucleotides, of which the alkaline microbial protease polynucleotides are particularly preferred. Serine proteases are enzymes which catalyze the hydrolysis of peptide bonds in which there is an essential serine residue at the active site. Serine proteases have molecular weights in the approximately 25,000 to 30,000 range (See, Priest, Bacteriol. Rev., 41:711-753 [1977]). In some preferred embodiments, polynucleotides encoding subtilisin and subtilisin variants are preferred precursor serine protease polynucleotides. In some embodiments, the invention encompasses polynucleotides encoding modified proteases that have been derived from polynucleotides of microorganisms such as *B. licheniformis, B. subtilis, B. amyloliquefaciens, B. clausii, B. lentus* and *B. halodurans*. A wide variety of *Bacillus* polynucleotides encoding subtilisins have been identified and sequenced, for example, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]; each of which is incorporated by reference in their entirety). In some embodiments of the present invention, mutant (e.g., variant) protease polynucleotides serve as precursor polynucleotides encoding proteins from which the modified proteases of the invention are derived. Numerous references provide examples of variant proteases (See e.g., WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165; each of which is incorporated by reference in its entirety). In other embodiments, polynucleotides encompassed by the invention include modified polynucleotides that are derived from polynucleotides encoding commercially available proteases. For example, commercially available proteases include, but are not limited to ALCALASE™, SAVINASE™, PRIMASE™, DURALASE™, ESPERASE™, and KANNASE™ (Novo Nordisk A/S), MAXATASE™, MAXACAL™, MAXAPEM™, PROPERASE™, PURAFECT™, and PURAFECT OXP™, (Genencor International Inc.). In some embodiments, the invention encompasses modified polynucleotides that are derived from polynucleotides encoding precursor proteases from *B. clausii*. In other embodiments, the invention encompasses modified polynucleotides that are derived from polynucleotides encoding precursor proteases from *B. lentus*.

In some embodiments, the modified full-length polynuclceotides of the invention comprise sequences that encode the pro region of precursor proteases that have been mutated. The polynucleotide sequence encoding the pro region of any suitable precursor protease finds use in the generation of one or more modified polynucleotides of the invention. In some preferred embodiments, the portion of a precursor polynucleotide sequence encoding a pro region is mutated to encode one or more amino acid substitutions at positions that are equivalent to positions 1-109 of the protease of SEQ ID NO:5, 13 or 244. In some embodiments, the modified precursor polynucleotides encode for at least one amino acid substitutions in the pro region at positions equivalent to E33, E43, A44, E47, V49, E57, A59, E63, E70, E74, E84, and E88 of SEQ ID NO:5, 13 or 244. In some embodiments, the polynucleotide sequence encoding the amino acid at position equivalent to E33 is mutated to encode at least one of substitutions E33D, E33I, E33S, E33N, E33K, E33H, E33Q, or E33R. In some other embodiments, the polynucleotide sequence encoding the amino acid at position equivalent to E57 is mutated to encode one of substitutions E57F, E57W, E57K, E57R, E57D, E57M, E57C, E57Q, E57S, E57H, and/or E57N.

In some embodiments, the precursor *B. clausii* protease polynucleotide (e.g., SEQ ID NO:1) encodes the wild-type protease (MAXACAL™; SEQ ID NO:5).

```
                                              (SEQ ID NO: 1)
ATGAAGAAACCGTTGGGGAAAATTGTCGCAAGCACCGCACTACTCA

TTTCTGTTGCTTTTAGTTCATCGATCGCATCGGCTGCTGAAGAAGC

AAAAGAAAAATATTTAATTGGCTTTAATGAGCAGGAAGCTGTCAGT

GAGTTTGTAGAACAAGTAGAGGCAAATGACGAGGTCGCCATTCTCT

CTGAGGAAGAGGAAGTCGAAATTGAATTGCTTCATGAATTTGAAAC

GATTCCTGTTTTATCCGTTGAGTTAAGCCCAGAAGATGTGGACGCG

CTTGAACTCGATCCAGCGATTTCTTATATTGAAGAGGATGCAGAAG

TAACGACAATGGCGCAATCAGTGCCATGGGGAATTAGCCGTGTGCA

AGCCCCAGCTGCCCATAACCGTGGATTGACAGGTTCTGGTGTAAAA

GTTGCTGTCCTCGATACAGGTATTTCCACTCATCCAGACTTAAATA

TTCGTGGTGGCGCTAGCTTTGTACCAGGGGAACCATCCACTCAAGA

TGGGAATGGGCATGGCACGCATGTGGCTGGGACGATTGCTGCTTTA

AACAATTCGATTGGCGTTCTTGGCGTAGCACCGAACGCGGAACTAT

ACGCTGTTAAAGTATTAGGGGCGAGCGGTTCAGGTTCGGTCAGCTC

GATTGCCCAAGGCAGGGAACAATGGCATGCACGTTGCTAATTTGAG

TTTAGGAAGCCCTTCGCCAAGTGCCACACTTGAGCAAGCTGTTAAT

AGCGCGACTTCTAGAGGCGTTCTTGTTGTAGCGGCATCTGGGAATT

CAGGTGCAGGCTCAATCAGCTATCCGGCCCGTTATGCGAACGCAAT

GGCAGTCGGAGCTACTGACCAAAACAACAACCGCGCCAGCTTTTCA

CAGTATGGCGCAGGGCTTGACATTGTCGCACCAGGTGTAAACGTGC

AGAGCACATACCCAGGTTCAACGTATGCCAGCTTAAACGGTACATC

GATGGCTACTCCTCATGTTGCAGGTGCAGCAGCCCTTGTTAAACAA

AAGAACCCATCTTGGTCCAATGTACAAATCCGCAATCATCTAAAGA

ATACGGCAACGAGCTTAGGAAGCACGAACTTGTATGGAAGCGGACT

TGTCAATGCAGAAGCGGCAACACGCTAA
                                              (SEQ ID NO: 5)
MKKPLGKIVASTALLISVAFSSSIASAAEEAKEKYLIGFNEQEAVSE

FVEQVEANDEVAILSEEEEVEIELLHEFETIPVLSVELSPEDVDALE

LDPAISYIEEDAEVTTMRVQAPAAHNRGLTGSGVKVAVLDTGISTHP

DLNIRGGASFVPGEPSTQDGNGHGTHVAGTIAALNNSIGVLGVAPNA

ELYAVKVLGASGSGSVSSIAQGLEWAGNNGMHVANLSLGSPSPSATL

EQAVNSATSRGVLVVAASGNSGAGSISYPARYANAMAVGATDQNNNR

ASFSQYGAGLDIVAPGVNVQSTYPGSTYASLNGTSMATPHVAGAAAL

VKQKNPSWSNVQIRNHLKNTATSLGSTNLYGSGLVNAEAATR
```

In other embodiments, the precursor *B. clausii* protease polynucleotide (e.g. SEQ ID NO:9) encodes a variant protease (e.g., SEQ ID NO:13)

```
                                              (SEQ ID NO: 13)
VRSKKLWIVASTALLISVAFSSSIASAAEEAKEKYLIGFNEQEAVS

EFVEQVEANDEVAILSEEEEVEIELLHEFETIPVLSVELSPEDVDA

LELDPAISYIEEDAEVTTMAQSVPWGISRVQAPAAHNRGLTGSGVKV

AVLDTGISTHPDLNIRGGASFVPGEPSTQDGNGHGTHVAGTIAALNN

SIGVLGVAPNAELYAVKVLGASGSGSVSSIAQGLEWAGNNVMHVANLS

LGLQAPSATLEQAVNSATSRGVLVVAASGNSGAGSISYPARYANAMAV

GATDQNNNRASFSQYGAGLDIVAPGVNVQSTYPGSTYASLNGTSMATPH
```

-continued

VAGAAALVKQKNPSWSNVQIRNHLKNTATSLGSTNLYGSGLVNAEA

ATR

In other embodiments, the precursor protease polynucleotide is a *B. lentus* polynucleotide (e.g. SEQ ID NO:240), which encodes a protease GG36 of SEQ ID NO:244.

(SEQ ID NO: 240)
GTGAGAAGCAAAAAATTGTGGATCGTCGCGTCGACCGCACTACTCA

TTTCTGTTGCTTTTAGTTCATCGATCGCATCGGCTGCTGAAGAAGC

AAAAGAAAAATATTTAATTGGCTTTAATGAGCAGGAAGCTGTCAGT

GAGTTTGTAGAACAAGTAGAGGCAAATGACGAGGTCGCCATTCTCT

CTGAGGAAGAGGAAGTCGAAATTGAATTGCTTCATGAATTTGAAAC

GATTCCTGTTTTATCCGTTGAGTTAAGCCCAGAAGATGTGGACGCG

CTTGAACTCGATCCAGCGATTTCTTATATTGAAGAGGATGCAGAAG

TAACGACAATGGCGCAATCAGTGCCATGGGGAATTAGCCGTGTGCA

AGCCCCAGCTGCCCATAACCGTGGATTGACAGGTTCTGGTGTAAAA

GTTGCTGTCCTCGATACAGGTATTTCCACTCATCCAGACTTAAATA

TTCGTGGTGGCGCTAGCTTTGTACCAGGGGAACCATCCACTCAAGA

TGGGAATGGGCATGGCACGCATGTGGCCGGGACGATTGCTGCTCTA

AACAATTCGATTGGCGTTCTTGGCGTAGCGCCGAGCGCGAACTATA

CGCTGTTAAAGTATTAGGGGCGAGCGGTTCAGGCTCGGTCAGCTCGA

TTGCCCAAGGATTGGAATGGGCAGGGAACAATGGCATGCACGTTGCT

AATTTGAGTTTAGGAAGCCCTTCGCCAAGTGCCACACTTGAGCAAGC

TGTTAATAGCGCGACTTCTAGAGGCGTTCTTGTTGTAGCGGCATCTG

GAAATTCAGGTGCAGGCTCAATCAGCTATCCGGCCCGTTATGCGAAC

GCAATGGCAGTCGGAGCTACTGACCAAAACAACAACCGCGCCAGCTT

TTCACAGTATGGCGCAGGGCTTGACATTGTCGCACCAGGTGTAAACG

TGCAGAGCACATACCCAGGTTCAACGTATGCCAGCTTAAACGGTACA

TCGATGGCTACTCCTCATGTTGCAGGTGCAGCAGCCCTTGTTAAACA

AAAGAACCCATCTTGGTCCAATGTACAAATCCGCAATCATCTAAAGA

ATACGGCAACGAGCTTAGGAAGCACGAACTTGTATGGAAGCGGACTTG

TCAATGCAGAAGCTGCAACTCGT (SEQ ID NO: 244)
MRSKKLWIVASTALLISVAFSSSIASAAEEEAKEKYLIGFNEQEAVSE

FVEQVEANDEVAILSEEEEVEIELLHEFETIPVLSVELSPEDVDALE

LDPAISYIEEDAEVTTMAQSVPWGISRVQAPAAHNRGLTGSGVKVAV

LDTGISTHPDLNIRGGASFVPGEPSTQDGNGHGTHVAGTIAALNNSI

GVLGVAPSAELYAVKVLGASGSGSVSSIAQGLEWAGNNGMHVANLSLG

SPSPSATLEQAVNSATSRGVLVVAASGNSGAGSISYPARYANAMAVGA

TDQNNNRASFSQYGAGLDIVAPGVNVQSTYPGSTYASLNGTSMATPHV

AGAAALVKQKNPSWSNVQIRNHLKNTATSLGSTNLYGSGLVNAEAATR

In some embodiments, the present invention provides modified full-length polynucleotides derived from the full-length precursor polynucleotide of SEQ ID NO:9.

(SEQ ID NO: 9)
GTGAGAAGCAAAAAATTGTGGATCGTCGCGTCGACCGCACTACTCATT

TCTGTTGCTTTTAGTTCATCGATCGCATCGGCTGCTGAAGAAGCAAAA

GAAAAATATTTAATTGGCTTTAATGAGCAGGAAGCTGTCAGTGAGTTT

GTAGAACAAGTAGAGGCAAATGACGAGGTCGCCATTCTCTCTGAGGAA

GAGGAAGTCGAAATTGAATTGCTTCATGAATTTGAAACGATTCCTGTT

TTATCCGTTGAGTTAAGCCCAGAAGATGTGGACGCGCTTGAACTCGAT

CCAGCGATTTCTTATATTGAAGAGGATGCAGAAGTAACGACAATGGCG

CAATCGGTACCATGGGGAATTAGCCGTGTGCAAGCCCCAGCTGCCCAT

AACCGTGGATTGACAGGTTCTGGTGTAAAAGTTGCTGTCCTCGATACA

GGTATTTCCACTCATCCAGACTTAAATATTCGTGGTGGCGCTAGCTTT

GTACCAGGGGAACCATCCACTCAAGATGGGAATGGGCATGGCACGCAT

GTGGCTGGGACGATTGCTGCTTTAAACAATTCGATTGGCGTTCTTGGC

GTAGCACCGAACGCGGAACTATACGCTGTTAAAGTATTAGGGGCGAGC

GGTTCAGGTTCGGTCAGCTCGATTGCCCAAGGATTGGAATGGGCAGGG

AACAATGTTATGCACGTTGCTAATTTGAGTTTAGGACTGCAGGCACCA

AGTGCCACACTTGAGCAAGCTGTTAATAGCGCGACTTCTAGAGGCGTT

CTTGTTGTAGCGGCATCTGGGAATTCAGGTGCAGGCTCAATCAGCTAT

CCGGCCCGTTATGCGAACGCAATGGCAGTCGGAGCTACTGACCAAAAC

AACAACCGCGCCAGCTTTTCACAGTATGGCGCAGGGCTTGACATTGTC

GCACCAGGTGTAAACGTGCAGAGCACATACCCAGGTTCAACGTATGCC

AGCTTAAACGGTACATCGATGGCTACTCCTCATGTTGCAGGTGCAGCA

GCCCTTGTTAAACAAAAGAACCCATCTTGGTCCAATGTACAAATCCGC

AATCATCTAAAGAATACGGCAACGAGCTTAGGAAGCACGAACTTGTAT

GGAAGCGGACTTGTCAATGCAGAAGCGGCAACACGTTAA

The polynucleotide sequence of SEQ ID NO:9 comprises a sequence (SEQ ID NO:10) that, when expressed, is contemplated to encode a signal sequence peptide (SEQ ID NO:14), which spans amino acids 1-27 of SEQ ID NO:13; an N-terminal pro sequence (SEQ ID NO:11) encoding a pro region sequence (SEQ ID NO:15), which spans amino acid residues 28-111 of SEQ ID NO:13; and a mature serine protease sequence (SEQ ID NO:12) encoding amino acid residues 112-380 of SEQ ID NO:13 (i.e., SEQ ID NO:16). The polynucleotide sequence encoding the first 8 amino acids of the signal peptide of the protease of SEQ ID NO: 13 is the sequence encoding the first 8 amino acids of the *B. subtilis* AprE protease.

(SEQ ID NO: 10)
GTGAGAAGCAAAAAATTGTGGATCGTCGCGTCGACCGCACTACTCATT

TCTGTTGCTTTTAGTTCATCGATCGCATCGGCT (SEQ ID NO: 15)
AEEAKEKYLIGFNEQEAVSEFVEQVEANDEVAILSEEEEVEIELLHEF

ETIPVLSVELSPEDVDALELDPAISYIEEDAEVTTM

-continued (SEQ ID NO: 14)
VRSKKLWIVASTALLISVAFSSSIASA (SEQ IS NO: 11)
GCTGAAGAAGCAAAAGAAAAATATTTAATTGGCTTTAATGAGCAGGA

AGCTGTCAGTGAGTTTGTAGAACAAGTAGAGGCAAATGACGAGGTCG

CCATTCTCTCTGAGGAAGAGGAAGTCGAAATTGAATTGCTTCATGAA

TTTGAAACGATTCCTGTTTTATCCGTTGAGTTAAGCCCAGAAGATGT

GGACGCGCTTGAACTCGATCCAGCGATTTCTTATATTGAAGAGGATG

CAGAAGTAACGACAATG (SEQ ID NO: 12)
GCGCAATCGGTACCATGGGGAATTAGCCGTGTGCAAGCCCCAGCTGC

CCATAACCGTGGATTGACAGGTTCTGGTGTAAAAGTTGCTGTCCTCG

ATACAGGTATTTCCACTCATCCAGACTTAAATATTCGTGGTGGCGCT

AGCTTTGTACCAGGGGAACCATCCACTCAAGATGGGAATGGGCATGG

CACGCATGTGGCTGGGACGATTGCTGCTTTAAACAATTCGATTGGCG

TTCTTGGCGTAGCACCGAACGCGGAACTATACGCTGTTAAAGTATTA

GGGGCGAGCGGTTCAGGTTCGGTCAGCTCGATTGCCCAAGGATTGGA

ATGGGCAGGGAACAATGTTATGCACGTTGCTAATTTGAGTTTAGGAC

TGCAGGCACCAAGTGCCACACTTGAGCAAGCTGTTAATAGCGCGACT

TCTAGAGGCGTTCTTGTTGTAGCGGCATCTGGGAATTCAGGTGCAGG

CTCAATCAGCTATCCGGCCCGTTATGCGAACGCAATGGCAGTCGGAG

CTACTGACCAAAACAACAACCGCGCCAGCTTTTCACAGTATGGCGCA

GGGCTTGACATTGTCGCACCAGGTGTAAACGTGCAGAGCACATACCC

AGGTTCAACGTATGCCAGCTTAAACGGTACATCGATGGCTACTCCTC

ATGTTGCAGGTGCAGCAGCCCTTGTTAAACAAAAGAACCCATCTTGG

TCCAATGTACAAATCCGCAATCATCTAAAGAATACGGCAACGAGCTT

AGGAAGCACGAACTTGTATGGAAGCGGACTTGTCAATGCAGAAGCGG

CAACACGTTAA (SEQ ID NO: 16)
AQSVPWGISRVQAPAAHNRGLTGSGVKVAVLDTGISTHPDLNIRGGA

SFVPGEPSTQDGNGHGTHVAGTIAALNNSIGVLGVAPNAELYAVKVL

GASGSGSVSSIAQGLEWAGNNVMHVANLSLGLQAPSATLEQAVNSAT

SRGVLVVAASGNSGAGSISYPARYANAMAVGATDQNNNRASFSQYGA

GLDIVAPGVNVQSTYPGSTYASLNGTSMATPHVAGAAALVKQKNPSW

SNVQIRNHLKNTATSLGSTNLYGSGLVNAEAATR

In other embodiments, the present invention provides modified full-length polynucleotides derived from the wild-type full-length precursor polynucleotide of SEQ ID NO:1. The polynucleotide of SEQ ID NO:1 comprises a sequence SEQ ID NO:2 that, when expressed, is contemplated to encode a signal sequence peptide (SEQ ID NO:6) which is amino acids 1-27 of SEQ ID NO:5; an N-terminal pro sequence (SEQ ID NO:3), encoding amino acid residues 28-111 of SEQ ID NO:5 (i.e. SEQ ID NO:7); and a wild-type mature serine protease sequence (SEQ ID NO:4) encoding amino acid residues 112-380 of SEQ ID NO:5 (i.e., SEQ ID NO:8)).

(SEQ ID NO: 2)
ATGAAGAAACCGTTGGGGAAAATTGTCGCAAGCACCGCACTACTCATTT

CTGTTGCTTTTAGTTCATCGATCGCATCGGCT (SEQ ID NO: 6)
MKKPLGKIVASTALLISVAFSSSIASA (SEQ ID NO: 3)
GCTGAAGAAGCAAAAGAAAAATATTTAATTGGCTTTAATGAGCAGGAAG

CTGTCAGTGAGTTTGTAGAACAAGTAGAGGCAAATGACGAGGTCGCCAT

TCTCTCTGAGGAAGAGGAAGTCGAAATTGAATTGCTTCATGAATTTGAA

ACGATTCCTGTTTTATCCGTTGAGTTAAGCCCAGAAGATGTGGACGCGC

TTGAACTCGATCCAGCGATTTCTTATATTGAAGAGGATGCAGAAGTAAC

GACAATG (SEQ ID NO: 7)
AEEAKEKYLIGFNEQEAVSEFVEQVEANDEVAILSEEEEVEIELLHEFE

TIPVLSVELSPEDVDALELDPAISYIEEDAEVTTM (SEQ ID NO: 4)
GCGCAATCAGTGCCATGGGGAATTAGCCGTGTGCAAGCCCCAGCTGCCC

ATAACCGTGGATTGACAGGTTCTGGTGTAAAAGTTGCTGTCCTCGATAC

AGGTATTTCCACTCATCCAGACTTAAATATTCGTGGTGGCGCTAGCTTT

GTACCAGGGGAACCATCCACTCAAGATGGGAATGGGCATGGCACGCATG

TGGCTGGGACGATTGCTGCTTTAAACAATTCGATTGGCGTTCTTGGCGT

AGCACCGAACGCGGAACTATACGCTGTTAAAGTATTAGGGGCGAGCGGT

TCAGGTTCGGTCAGCTCGATTGCCCAAGGATTGGAATGGGCAGGGAACA

ATGGCAACGTTGCTAATTTGAGTGCTTTAGGAAGCCCTTCGCCAAGTGC

CACACTTGAGCAAGCTGTTAATAGCGCGACTTCTAGAGGCGTTCTTGTT

GTAGCGGCATCTGGGAATTCAGGTGCAGGCTCAATCAGCTATCCGGCCC

GTTATGCGAACGCAATGGCAGTCGGAGCTACTGACCAAAACAACAACCG

CGCCAGCTTTTCACAGTATGGCGCAGGGCTTGACATTGTCGCACCAGGT

GTAAACGTGCAGAGCACATACCCAGGTTCAACGTATGCCAGCTTAAACG

GTACATCGATGGCTACTCCTCATGTTGCAGGTGCAGCAGCCCTTGTTAA

ACAAAAGAACCCATCTTGGTCCAATGTACAAATCCGCAATCATCTAAAG

AATACGGCAACGAGCTTAGGAAGCACGAACTTGTATGGAAGCGGACTTG

TCAATGCAGAAGCGGCAACACGCTAA (SEQ ID NO: 8)
RVQAPAAHNRGLTGSGVKVAVLDTGISTHPDLNIRGGASFVPGEPSTQD

GNGHGTHVAGTIAALNNSIGVLGVAPNAELYAVKVLGASGSGSVSSIAQ

GLEWAGNNGMHVANLSLGSPSPSATLEQAVNSATSRGVLVVAASGNSGA

GSISYPARYANAMAVGATDQNNNRASFSQYGAGLDIVAPGVNVQSTYPG

STYASLNGTSMATPHVAGAAALVKQKNPSWSNVQIRNHLKNTATSLGST

NLYGSGLVNAEAATR

In other embodiments, the present invention provides modified full-length polynucleotides derived from the variant full-length precursor polynucleotide of SEQ ID NO:240. The polynucleotide of SEQ ID NO:240 comprises a sequence SEQ ID NO:241 that, when expressed, is contemplated to encode a signal sequence peptide (SEQ ID NO:245) which is amino acids 1-27 of SEQ ID NO:244; an N-terminal pro sequence (SEQ ID NO:242), encoding amino acid residues 28-111 of SEQ ID NO:244 (i.e. SEQ ID NO:246); and a wild-type mature serine protease sequence (SEQ ID NO:243) encoding amino acid residues 112-380 of SEQ ID NO:244 (i.e., SEQ ID NO:247)). The polynucleotide sequence encoding the first 8 amino acids of the signal peptide of the precursor protease of SEQ ID NO: 244 is the sequence encoding the first 8 amino acids of the *B. subtilis* AprE protease. The pro portion and the mature portion of the precursor GG36 are encoded by the GG36 wild-type sequence.

```
                                            (SEQ ID NO: 241)
GTGAGAAGCAAAAAATTGTGGATCGTCGCGTCGACCGCACTACT

CATTTCTGTTGCTTTTAGTTCATCGATCGCATCGGCT (SEQ ID NO: 245)
MRSKKLWIVASTALLISVAFSSSIASA (SEQ ID NO: 242)
GCTGAAGAAGCAAAAGAAAAATATTTAATTGGCTTTAATGAGC

AGGAAGCTGTCAGTGAGTTTGTAGAACAAGTAGAGGCAAATGA

CGAGGTCGCCATTCTCTCTGAGGAAGAGGAAGTCGAAATTGAA

TTGCTTCATGAATTTGAAACGATTCCTGTTTTATCCGTTGAGT

TAAGCCCAGAAGATGTGGACGCGCTTGAACTCGATCCAGCGAT

TTCTTATATTGAAGAGGATGCAGAAGTAACGACAATG (SEQ ID NO: 246)
AEEAKEKYLIGFNEQEAVSEFVEQVEANDEVAILSEEEEVEIE

LLHEFETIPVLSVELSPEDVDALELDPAISYIEEDAEVTTM (SEQ ID NO: 243)
GCGCAATCAGTGCCATGGGGAATTAGCCGTGTGCAAGCCCCAG

CTGCCCATAACCGTGGATTGACAGGTTCTGGTGTAAAAGTTGC

TGTCCTCGATACAGGTATTTCCACTCATCCAGACTTAAATATT

CGTGGTGGCGCTAGCTTTGTACCAGGGGAACCATCCACTCAAGA

TGGGAATGGGCATGGCACGCATGTGGCCGGGACGATTGCTGCTC

TAAACAATTCGATTGGCGTTCTTGGCGTAGCGCCGAGCGCGGAA

CTATACGCTGTTAAAGTATTAGGGGCGAGCGGTTCAGGCTCGGT

CAGCTCGATTGCCCAAGGATTGGAATGGGCAGGGAACAATGGCA

TGCACGTTGCTAATTTGAGTTTAGGAAGCCCTTCGCCAAGTGCC

ACACTTGAGCAAGCTGTTAATAGCGCGACTTCTAGAGGCGTTCTT

GTTGTAGCGGCATCTGGAAATTCAGGTGCAGGCTCAATCAGCTATC

CGGCCCGTTATGCGAACGCAATGGCAGTCGGAGCTACTGACCAAA

ACAACAACCGCGCCAGCTTTTCACAGTATGGCGCAGGGCTTGACAT

TGTCGCACCAGGTGTAAACGTGCAGAGCACATACCCAGGTTCAACG

TATGCCAGCTTAAACGGTACATCGATGGCTACTCCTCATGTTGCAG

GTGCAGCAGCCCTTGTTAAACAAAAGAACCCATCTTGGTCCAATGT

ACAAATCCGCAATCATCTAAAGAATACGGCAACGAGCTTAGGAAGC

ACGAACTTGTATGGAAGCGGACTTGTCAATGCAGAAGCTGCAACTC

GTTA (SEQ ID NO: 247)
AQSVPWGISRVQAPAAHNRGLTGSGVKVAVLDTGISTHPDLNIRGG

ASFVPGEPSTQDGNGHGTHVAGTIAALNNSIGVLGVAPSAELYAVK

VLGASGSGSVSSIAQGLEWAGNNGMHVANLSLGSPSPSATLEQAVN

SATSRGVLVVAASGNSGAGSISYPARYANAMAVGATDQNNNRASFS

QYGAGLDIVAPGVNVQSTYPGSTYASLNGTSMATPHVAGAAALVKQ

KNPSWSNVQIRNHLKNTATSLGSTNLYGSGLVNAEAATR
```

In preferred embodiments, the modified full-length polynuculceotides of the invention comprise sequences that encode the pro region of precursor proteases that have been mutated. The polynucleotide sequence encoding the pro region of any suitable precursor protease finds use in the generation of one or more modified polynucleotides of the invention. In some preferred embodiments, the portion of a precursor polynucleotide sequence encoding a pro region is mutated to encode one or more amino acid substitutions at positions that are equivalent to positions 1-109 of the protease of SEQ ID NO:13. In other embodiments, the substitutions are made at positions that are equivalent to 1-109 of the protease of SEQ ID NO:5. In yet other embodiments, the substitutions are made at positions that are equivalent to positions 1-109 of the protease of SEQ ID NO:244. In some embodiments, the modified precursor polynucleotides encode for at least one amino acid substitutions at positions equivalent to E33, E43, A44, E47, V49, E57, A59, E63, E70, E74, E84, and E88 of SEQ ID NO:5, 13 or 244. In some embodiments, the polynucleotide sequence encoding the amino acid at position equivalent to E33 is mutated to encode at least one of substitutions E33D, E33I, E33S, E33N, E33K, E33H, E33Q, or E33R. In some other embodiments, the polynucleotide sequence encoding the amino acid at position equivalent to E57 is mutated to encode one of substitutions E57F, E57W, E57K, E57R, E57D, E57M, E57C, E57Q, E57S, E57H, and/or E57N.

As discussed above, in some embodiments, the polynucleotide encoding any precursor protease is mutated to generate at least one modified polynucleotide encoding at least one modified protease having a mutated pro region. In some particularly preferred embodiments, full-length polynucleotides encoding serine proteases find use in the generation of the modified polynucleotides of the invention. In some alternative particularly preferred embodiments, full-length polynucleotides encoding alkaline serine proteases find use. As discussed above, the polynucleotides encoding the precursor proteases are from microorganisms including but not limited to *B. licheniformis, B. subtilis, B. amyloliquefaciens, B. clausii, B. lentus* and *B. halodurans*. The invention provides for any one of the In some embodiments, the modified polynucleotides of the invention that encode full-length modified proteases comprise sequences that encode mature forms of the proteases that share at least about 65% amino acid sequence identity, preferably at least about 70% amino acid sequence identity, more preferably at least about 75% amino acid sequence identity, still more preferably at least about 80% amino acid sequence identity, more preferably at least about 85% amino acid sequence identity, even more preferably at least about 90% amino acid sequence identity, more preferably at least about 92% amino acid sequence identity, yet more preferably at least about 95% amino acid sequence identity, more preferably at least about 97% amino acid sequence identity, still more preferably at least about 98% amino acid sequence identity, and most preferably at least about 99% amino acid sequence identity with the amino acid sequence of the mature form of the precursor protease and have comparable or enhanced production activity as compared to the precursor polypeptide. In some embodiments, the modified polynucleotides of the invention that encode the full-length modified proteases comprise sequences that encode mature forms of the proteases that share at least about 65% amino acid sequence identity, preferably at least about 70% amino acid sequence identity, more preferably at least about 75% amino acid sequence identity, still more preferably at least about 80% amino acid sequence identity, more preferably at least about 85% amino acid sequence identity, even more preferably at least about 90% amino acid sequence identity, more preferably at least about 92% amino acid sequence identity, yet more preferably at least about 95% amino acid sequence identity, more preferably at least about 97% amino acid sequence identity, still more preferably at least about 98% amino acid sequence identity, and most preferably at least about 99% amino acid sequence identity with the amino acid sequence of SEQ ID NO:8, SEQ ID NO:16 or SEQ ID NO:247.

In some embodiments, the modified polynucleotides encode full-length amino acid sequences that share up to 65% amino acid sequence identity, preferably up to about 70% amino acid sequence identity, more preferably up to about 75% amino acid sequence identity, still more preferably up to about 80% amino acid sequence identity, more preferably up to about 85% amino acid sequence identity, even more preferably up to about 90% amino acid sequence identity, more preferably up to about 92% amino acid sequence identity, yet more preferably up to about 95% amino acid sequence identity, more preferably up to about 97% amino acid sequence identity, still more preferably up to about 98% amino acid sequence identity, and most preferably up to about 99% amino acid sequence identity with the amino acid sequence of the precursor protease and have comparable or enhanced production activity, as compared to the precursor polypeptide.

As will be understood by the skilled artisan, due to the degeneracy of the genetic code, a variety of modified polynucleotides encode modified proteases. In some other embodiments of the present invention, polynucleotides comprising a nucleotide sequence having at least about 70% sequence identity, at least about 75% sequence identity, at least about 80% sequence identity, at least about 85% sequence identity, at least about 90% sequence identity, at least about 92% sequence identity, at least about 95% sequence identity, at least about 97% sequence identity, at least about 98% sequence identity and at least about 99% sequence identity to the polynucleotide sequence of SEQ ID NOS:4, 12, or 243 are provided.

In some embodiments, the percent identity shared by polynucleotide sequences is determined by direct comparison of the sequence information between the molecules by aligning the sequences and determining the identity by methods known in the art. In some embodiments, the percent identity (e.g., amino acid sequence, nucleic acid sequence, and/or gene sequence) is determined by a direct comparison of the sequence information between two molecules by aligning the sequences, counting the exact number of matches between the two aligned sequences, dividing by the length of the shorter sequence, and multiplying the result by 100. Readily available computer programs find use in these analyses, including those described above. Programs for determining nucleotide sequence identity are available in the Wisconsin Sequence Analysis Package, Version 8 (Genetics Computer Group, Madison, Wis.) for example, the BEST-FIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., J. Mol. Biol., 215:403-410 (1990). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff & Henikoff, Proc. Natl. Acad. Sci. USA 89:10915 (1989)) alignments (B) of 50, expectation (E) of 10, M'5, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

In some embodiments of the present invention, sequences were analyzed by BLAST and protein translation sequence tools. In some experiments, the preferred version was BLAST (Basic BLAST version 2.0). The program chosen was "BlastX", and the database chosen was "nr." Standard/default parameter values were employed.

Several methods are known in the art that are suitable for generating modified polynucleotide sequences of the present invention, including but not limited to site-saturation mutagenesis, scanning mutagenesis, insertional mutagenesis, deletion mutagenesis, random mutagenesis, site-directed mutagenesis, and directed-evolution, as well as various other recombinatorial approaches.

In some embodiments, the modified polynucleotide sequences of the invention comprise modifications of the sequence encoding the pro region of the protease that are generated with site directed mutagenesis in at least one codon. In other preferred embodiments, site directed mutagenesis is performed for two or more codons. In some further embodiments, modified polynucleotide sequences that encode the pro region of the modified protease have up to about 40%, up to about 45%, up to about 50%, up to about 55%, up to about 60%, up to about 65%, up to about 70%, up to about 75%, up to about 80%, up to about 85%, up to about 90%, up to about 95%, up to about 98%, or up to about 99% homology with the polynucleotide that encodes the pro region of the precursor polypeptide e.g. SEQ ID NOS:3, 11 or 242. In some alternative embodiments, the modified polynucleotide is generated in vivo, using any known mutagenic procedure such as, for example, radiation, nitrosoguanidine and the like. The desired modified polynucleotide sequence is then isolated and used in the methods provided herein.

In some preferred embodiments, site saturation mutagenesis of the pro region of the precursor protease polynucleotides is accomplished by using a composition comprising mutagenic primers. Mutagenic primers do not precisely match the precursor polynucleotide, and the mismatch or mismatches in the primers are used to introduce the desired mutation into the template polynucleotide. Non-mutagenic primers, which match precisely the precursor polynucleotide are also included in the primer composition. By adding a mixture of mutagenic primers and non-mutagenic primers corresponding to at least one of the mutagenic primers, a nucleic acid library in which a variety of mutational patterns are presented is produced. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between about 10 to about 50 bases in length, more preferably about 15 to about 45 bases in length. With respect to corresponding mutagenic and non-mutagenic primers, it is not necessary that the corresponding oligonucleotides be of identical length, but only that there is overlap in the region corresponding to the mutation to be added.

In some embodiments, primers are added in a pre-defined ratio. For example, if it is desired that the resulting library have a significant level of a certain specific mutation and a lesser amount of a different mutation at the same or different site, by adjusting the amount of primer added, the desired biased library is produced. Alternatively, by adding lesser or greater amounts of non-mutagenic primers, the frequency with which the corresponding mutation(s) are produced in the mutant nucleic acid library is adjusted. Kits comprising compositions of primers for site—directed mutagenesis are commercially available and include the QuikChange® site-directed mutagenesis kit (Stratagene, San Diego, Calif.). In some embodiments, precursor polynucleotides are further modified to encode modified proteases that comprise two or more amino acid substitutions in the pro region. Kits for performing multi-site directed mutagenesis are also commercially available (e.g., QuikChange® Multisite, Stratagene, San Diego, Calif.).

In some embodiments, the modified polynucleotides of the invention are generated using site-saturation methods. In some other embodiments, each of the modified polynucleotides comprises at least one amino acid substitution in the pro region.

The present invention provides modified full-length precursor proteases that are encoded by any one of the modified polynucleotides of the invention. The invention provides for mature forms of proteases that when processed from modified precursor proteases, can be produced at levels that are greater than those levels attained by processing of the unmodified precursor proteases.

The invention encompasses full-length proteases that have been modified by mutating at least one amino acid of the pro region of a precursor protease. In some embodiments, the precursor protease is mutated at one or more amino acids of the pro region that are equivalent to amino acids 28-109 of the pro region (SEQ ID NO:15) of the full-length precursor protease of SEQ ID NO:13, the pro region (SEQ ID NO:7) of the full-length precursor protease of SEQ ID NO:5, or the pro region (SEQ ID NO:246) of the full-length precursor protease of SEQ ID NO:244. In some embodiments, the amino acid substitutions are made at positions equivalent to E33, E43, A44, E47, V49, E57, A59, E63, E70, E74, E84 and/or E88 of the *B. clausii* V049 precursor protease (SEQ ID NO:13), of the *B. clausii* wild-type protease (SEQ ID NO:5), or of the wild-type *B. lentus* protease (SEQ ID NO: 244).

In some embodiments, the substitution of amino acids at positions equivalent to E33, include, but are not limited to E33D, E33I, E33S, E33N, E33K, E33H, E33Q or E33R. In other embodiments, the substitution of E57, includes, but is not limited to E57F, E57W, E57K, E57R, E57D, E57M, E57C, E57Q, E57G, E57S, E57H or E57N. The present invention encompasses modified proteases wherein any one amino acid substitution at each of the amino acid positions equivalent to amino acid 28-109 of SEQ ID NO:5, 13 or 244 is made with any one of the nineteen naturally occurring L-amino acids to enhance the production/secretion of the modified protease in comparison to that of the precursor protease (See, Table 2 and Example 4). The amino acids are referred to herein by the commonly used and understood one letter code (See e.g., Dale, M. W. (1989), *Molecular Genetics of Bacteria*, John Wiley & Sons, Ltd.).

In some embodiments, the modified precursor protease polypeptides comprise mature regions that share at least about 65% amino acid sequence identity, preferably at least about 70% amino acid sequence identity, more preferably at least about 75% amino acid sequence identity, still more at least about 80% amino acid sequence identity, more preferably at least about 85% amino acid sequence identity, even more preferably at least about 90% amino acid sequence identity, more preferably at least about 92% amino acid sequence identity, yet more preferably at least about 95% amino acid sequence identity, more preferably at least about 97% amino acid sequence identity, still more preferably at least about 98% amino acid sequence identity, and most preferably at least about 99% to the amino acid sequence shown in SEQ ID NOS:8, 16 or 247, and have comparable or enhanced production activity to the precursor polypeptide.

As indicated above, in some embodiments, the present invention provides vectors comprising the aforementioned polynucleotides. In some preferred embodiments, the vector is an expression vector in which the DNA sequence encoding the protease of the invention is operably linked to additional segments required for transcription of the DNA. In some preferred embodiments, the expression vector is derived from plasmid or viral DNA, or in alternative embodiments, contains elements of both. Exemplary vectors include, but are not limited to pXX, pC194, pJH101, pE194, pHP13 (Harwood and Cutting (eds), *Molecular Biological*

*Methods for Bacillus*, John Wiley & Sons, [1990], in particular, chapter 3; suitable replicating plasmids for *B. subtilis* include those listed on page 92; Perego, M. (1993) Integrational Vectors for Genetic Manipulations in *Bacillus subtilis*, p. 615-624; A. L. Sonenshein, J. A. Hoch, and R. Losick (ed.), *Bacillus subtilis* and other Gram-positive bacteria: biochemistry, physiology and molecular genetics, American Society for Microbiology, Washington, D.C.).

In some preferred embodiments, the vector pXX finds use in the construction of vectors comprising the polynucleotides described herein (e.g., pXX-049; See, FIG. 6). It is intended that each of the vectors described herein will find use in the present invention. In some embodiments, the construct is present on a replicating plasmid (e.g., pHP13), while in other embodiments, it is integrated into the chromosome in one or more copies. Examples of sites for integration include, but are not limited to the aprE, the amyE, the veg or the pps regions. Indeed, it is contemplated that other sites known to those skilled in the art will find use in the present invention. In some embodiments, the promoter is the wild-type promoter for the selected precursor protease. In some other embodiments, the promoter is heterologous to the precursor protease, but is functional in the host cell. Specifically, examples of suitable promoters for use in bacterial host cells include but are not limited to the pSPAC, pAprE, pAmyE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilus* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

In some preferred embodiments, the expression vector contains a multiple cloning site cassette which preferably comprises at least one restriction endonuclease site unique to the vector, to facilitate ease of nucleic acid manipulation. In some further preferred embodiments, the vector also comprises one or more selectable markers (e.g., antimicrobial markers such as erythromycin, actinomycin, chloramphenicol, and/or tetracycline). In yet other embodiments, a multicopy replicating plasmid finds use for integration of the plasmid into the *Bacilllus* genomic DNA, using methods known in the art.

For expression and production of protein(s) of interest e.g. a protease, in a cell, at least one expression vector comprising at least one copy of a polynucleotide encoding the modified protease, and preferably comprising multiple copies, is transformed into the cell under conditions suitable for expression of the protein(s). In some particularly preferred embodiments, the sequences encoding the protein of interest e.g. proteases (as well as other sequences included in the vector) are integrated into the genome of the host cell, while in other embodiments, the plasmids remain as autonomous extra-chromosomal elements within the cell. Thus, the present invention provides both extrachromosomal elements as well as incoming sequences that are integrated into the host cell genome.

Precursor and modified proteases are produced in host cells of any suitable Gram-positive microorganism, including bacteria and fungi. For example, in some embodiments, the modified protease is produced in host cells of fungal and/or bacterial origin. In some embodiments, the host cells are *Bacillus* sp., *Streptomyces* sp., *Escherichia* sp. or *Aspergillus* sp. In some preferred embodiments, the modified proteases are produced by host cells of the genus *Bacillus*.

Examples of *Bacillus* host cells that find use in the production of the modified proteins of the present invention include, but are not limited to *B. licheniformis*, *B. lentus*, *B. subtilis*, *B. amyloliquefaciens*, *B. lentus*, *B. brevis*, *B. stearothermophilus*, *B. alkalophilus*, *B. coagulans*, *B. circulans*, *B. pumilus*, *B. thuringiensis*, *B. clausii*, and *B. megaterium*, as well as other organisms within the genus *Bacillus*. In some particularly preferred embodiments, *B. subtilis* host cells find use. U.S. Pat. Nos. 5,264,366 and 4,760,025 (RE 34,606) describe various *Bacillus* host strains that find use in the present invention, although other suitable strains find use in the present invention.

Industrial strains that find use in the present invention include non-recombinant (i.e., wild-type) *Bacillus* strains, as well as variants of naturally occurring strain and/or recombinant strains. In some preferred embodiments, the host strain is a recombinant strain, wherein a polynucleotide encoding a polypeptide of interest has been introduced into the host. In some preferred embodiments, the host strain is a *B. subtilis* host strain and particularly a recombinant *Bacillus subtilis* host strain. Numerous *B. subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics, 73:215-228 [1973]) (See also, U.S. Pat. No. 4,450,235; U.S. Pat. No. 4,302,544; and EP 0134048; each of which is incorporated by reference in its entirety). The use of *B. subtilis* as an expression host well known in the art (See e.g., See, Palva et al., Gene 19:81-87 [1982]; Fahnestock and Fischer, J. Bacteriol., 165:796-804 [1986]; and Wang et al., Gene 69:39-47 [1988]).

In some embodiments, a preferred *Bacillus* host is a *Bacillus* sp. that includes a mutation or deletion in at least one of the following genes, degU, degS, degR and degQ. Preferably the mutation is in a degU gene, and more preferably the mutation is degU(Hy)32. (See e.g., Msadek et al., J. Bacteriol., 172:824-834 [1990]; and Olmos et al., Mol. Gen. Genet., 253:562-567 [1997]). A more particularly preferred host strain is a *Bacillus subtilis* carrying a degU32 (Hy) mutation. In some further embodiments, the *Bacillus* host comprises a mutation or deletion in scoC4, (See, e.g., Caldwell et al., J. Bacteriol., 183:7329-7340 [2001]); spoIIE (See, Arigoni et al., Mol. Microbiol., 31:1407-1415 [1999]); and/or oppA or other genes of the opp operon (See e.g., Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* that can be used to produce the modified proteases of the invention is a *Bacillus* host strain that already includes a mutation in one or more of the above-mentioned genes (in some embodiments, mutations in other genes are also present). In some alternative embodiments, an altered *Bacillus* further engineered to include mutations of one or more of the above-mentioned genes finds use.

Host cells are transformed with modified polynucleotides encoding the modified proteases of the present invention using any suitable method known in the art. Whether the modified polynucleotide is incorporated into a vector or is used without the presence of plasmid DNA, it is introduced into a microorganism, in some embodiments, preferably an *E. coli* cell or a competent *Bacillus* cell. Methods for introducing DNA into *Bacillus* cells involving plasmid constructs and transformation of plasmids into *E. coli* are well known. In some embodiments, the plasmids are subsequently isolated from *E. coli* and transformed into *Bacillus*. However, it is not essential to use intervening microorganisms such as *E. coli*, and in some embodiments, a DNA construct or vector is directly introduced into a *Bacillus* host.

Those of skill in the art are well aware of suitable methods for introducing polynucleotide sequences into *Bacillus* cells (See e.g., Ferrari et al., "Genetics," in Harwood et al. (ed.), *Bacillus, Plenum Publishing Corp.* [1989], pages 57-72; Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; Chang et al., Mol. Gen. Genet., 168:11-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; and McDonald, J. Gen. Microbiol., 130:203 [1984]). Indeed, such methods as transformation, including protoplast transformation and congression, transduction, and protoplast fusion are known and suited for use in the present invention. Methods of transformation are particularly preferred to introduce a DNA construct provided by the present invention into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell without insertion into a plasmid or vector. Such methods include, but are not limited to calcium chloride precipitation, electroporation, naked DNA, liposomes and the like. In additional embodiments, DNA constructs are co-transformed with a plasmid, without being inserted into the plasmid. In further embodiments, a selective marker is deleted from the altered *Bacillus* strain by methods known in the art (See, Stahl et al., J. Bacteriol., 158:411-418 [1984]; and Palmeros et al., Gene 247:255-264 [2000]).

As indicated above, in some embodiments of the present invention, nucleic acid encoding at least one modified polypeptide of interest is introduced into a host cell via an expression vector capable of replicating within the host cell. Suitable replicating and integrating plasmids for *Bacillus* known in the art (See e.g., Harwood and Cutting (eds), *Molecular Biological Methods for Bacillus*, John Wiley & Sons, [1990], in particular, chapter 3; suitable replicating plasmids for *B. subtilis* include those listed on page 92). Although there are technical hurdles, those of skill in the art know that there are several strategies for the direct cloning of DNA in *Bacillus*.

Methods known in the art to transform *Bacillus*, include such methods as plasmid marker rescue transformation, which involves the uptake of a donor plasmid by competent cells carrying a partially homologous resident plasmid (Contente et al., Plasmid 2:555-571 [1979]; Haima et al., Mol. Gen. Genet., 223:185-191 [1990]; Weinrauch et al., J. Bacteriol., 154:1077-1087 [1983]; and Weinrauch et al., J. Bacteriol., 169:1205-1211 [1987]). In this method, the incoming donor plasmid recombines with the homologous region of the resident "helper" plasmid in a process that mimics chromosomal transformation.

Other methods involving transformation by protoplast transformation are known in the art (See e.g., Chang and Cohen, Mol. Gen. Genet., 168:111-115 [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; McDonald [1984] J. Gen. Microbiol., 130:203 [1984]; and Bakhiet et al., 49:577 [1985]). In addition, Mann et al., (Mann et al., Curr. Microbiol., 13:131-135 [1986]) describe transformation of *Bacillus* protoplasts, and Holubova (Holubova, Microbiol., 30:97 [1985]) describe methods for introducing DNA into protoplasts using DNA-containing liposomes. In some preferred embodiments, marker genes are used in order to indicate whether or not the gene of interest is present in the host cell.

In addition to these methods, in other embodiments, host cells are directly transformed. In "direct transformation," an intermediate cell is not used to amplify, or otherwise process, the modified polynucleotide prior to introduction into the host (i.e., *Bacillus*) cell. Introduction of the modified polynucleotide into the host cell includes those physical and chemical methods known in the art to introduce modified polynucleotide into a host cell without insertion into a plasmid or vector. Such methods include but are not limited to the use of competent cells, as well as the use of "artificial means" such as calcium chloride precipitation, electroporation, etc. to introduce DNA into cells. Thus, the present invention finds use with naked DNA, liposomes and the like. In yet other embodiments, the modified polynucleotides are co-transformed with a plasmid without being inserted into the plasmid.

More particularly, the present invention provides constructs, vectors comprising polynucleotides described herein, host cells transformed with such vectors, proteases expressed by such host cells, expression methods and systems for the production of homologous or heterologous serine protease enzymes derived from microorganisms (in particular, members of the genus *Bacillus*). In some embodiments, the modified polynucleotide(s) encoding modified serine protease(s) are used to produce recombinant host cells suitable for the expression of the modified serine protease(s). In some preferred embodiments, the expression hosts are capable of enhancing the secretion of the mature forms of the modified protease(s) thus increasing the commercial production of proteases.

In some embodiments, the host cells and transformed cells of the present invention are cultured in conventional nutrient media. The suitable specific culture conditions, such as temperature, pH and the like are known to those skilled in the art. In addition, some preferred culture conditions may be found in the scientific literature such as Hopwood (2000) *Practical Streptomyces Genetics*, John Innes Foundation, Norwich UK; Hardwood et al., (1990) *Molecular Biological Methods for Bacillus*, John Wiley and from the American Type Culture Collection (ATCC).

In some embodiments, host cells transformed with polynucleotide sequences encoding modified proteases are cultured under conditions suitable for the expression and recovery of the encoded protein from cell culture. The protein produced by a recombinant host cell comprising a modified protease of the present invention is secreted into the culture media. In some embodiments, other recombinant constructions join the heterologous or homologous polynucleotide sequences to nucleotide sequence encoding a protease polypeptide domain which facilitates purification of the soluble proteins (Kroll D J et al (1993) DNA Cell Biol 12:441-53).

Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

In some preferred embodiments, the cells transformed with polynucleotide sequences encoding heterologous or homologous protein or endogenously having said protein are cultured under conditions suitable for the expression and recovery of the encoded protein from the cell culture medium. In some embodiments, other recombinant constructions include heterologous or homologous polynucleotide sequences to nucleotide sequence encoding a polypeptide domain which facilitates purification of soluble protein (e.g., tags of various sorts) (Kroll et al., DNA Cell. Biol., 12:441-53 [1993]).

Such purification facilitating domains include, but are not limited to, metal chelating peptides such as histidine-tryptophan modules that allow purification on immobilized metals (Porath, Prot. Expr. Purif., 3:263-281 [1992]), protein A domains that allow purification on immobilized immunoglobulin, and the domain utilized in the FLAGS extension/ affinity purification system (Immunex Corp, Seattle Wash.). The inclusion of a cleavable linker sequence such as Factor XA or enterokinase (Invitrogen, San Diego, Calif.) between the purification domain and the heterologous protein finds use in facilitating purification.

In some preferred embodiments, the transformed host cells of the present invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the protease produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

As indicated above, the polypeptides of the invention are produced as mature enzymes at levels greater than the mature enzymes processes from their corresponding unmodified precursor polypeptides. In preferred embodiments of the present invention, the mutations within the pro region of a precursor polypeptide enhance the secretion/ expression of the mature polypeptide when compared to a corresponding mature protease that has been processed from a precursor protease when produced by a *Bacillus* strain under the same conditions.

One measure of enhancement can be determined as an activity ratio, which can be expressed as the ratio of the enzymatic activity of the mature form processed from the modified protease to the enzymatic activity of the mature form processed from the precursor protease. A ratio equal or greater than 1 indicates that the mature form of modified protease is produced at levels equal or greater than those at which the mature form of precursor protease is produced. For example, an activity ratio of 1.5 indicates that the mature protease that has been processed from a modified protease is produced at 1.5 times the level at which the mature protease that is processed from the precursor protease i.e. the modified protease yields 50% more mature protease than the unmodified precursor protease. In some embodiments, the activity ratio is at least 1, at least about 1.05, about at least about 1.1, at least about 1.2, at least about 1.3, at least about 1.4, at least about 1.5, at least about 1.6, at least about 1.7, at least about 1.8. at least about 1.9, and at least about 2. In other embodiments, the activity ratio is at least about 2.1, at least about 2.2, at least about 2.3, at least about 2.4, at least about 2.5, at least about 2.6, at least about 2.7, at least about 2.8, at least about 2.9 and at least about 3. In yet other embodiments, the activity ratio is at least about 3.5, at least about 4.0, and at least about 5. Thus, in some embodiments, production of the mature protease processed from the modified protease is enhanced by at least about 0.5%, about 1.0%, about 1.5%, about 2.0%, about 2.5%, about 3.0%, about 4.0%, about 5.0%, about 8.0%, about 10%, about 15%, about 20%, about 25%, about 30%, about 40%, about 50%, at least about 60%, at least about 70%, at least about 80%, at least about 90%, at least about 100% or more, compared to the corresponding mature protease processed from the unmodified precursor protease. In other embodiments, production of the mature form of the protease that is processed from the modified protease is enhanced by at least about 110%, 120%, 130%, 140%, 150%, 160%, 170%, 180%, 190%, and up to at least about 200%, or more compared to the corresponding production of the mature form of the protease that was processed from the unmodified precursor protease. In some embodiments, the enhanced production of the modified protease is determined based on the ratio of the proteolytic activity of the mature form processed from the modified protease compared to the proteolytic activity of the mature form of the corresponding unmodified precursor protease.

Other means for determining the levels of secretion of a heterologous or homologous protein in a host cell and detecting secreted proteins include, but are not limited to methods that use either polyclonal or monoclonal antibodies specific for the protein. Examples include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med., 158:1211 [1983]). In some preferred embodiments of the present invention, secretion is higher using the methods and compositions provided herein than when using the same methods or compositions, but where a peptide transport protein or gene product of a peptide transport operon has not been introduced.

There are various assays known to those of ordinary skill in the art for detecting and measuring activity of polypeptides of the invention. In particular, assays are available for measuring protease activity that are based on the release of acid-soluble peptides from casein or hemoglobin, measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Some other assays involve the solubilization of chromogenic substrates (See e.g., Ward, "Proteinases," in Fogarty (ed.)., *Microbial Enzymes and Biotechnology*, Applied Science, London, [1983], pp 251-317). Other exemplary assays include, but are not limited to succinyl-Ala-Ala-Pro-Phe-para nitroanilide assay (SAAPFpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem., 223:119-129 [1994]; and Hsia et al., Anal Biochem., 242:221-227 [1999]). It is not intended that the present invention be limited to any particular assay method(s).

In some embodiments, the production of the modified protease by a microorganism is determined by using a ratio of the activity of a mature protease processed from a modified precursor protease compared to the activity of the mature protease processed from an unmodified precursor protease. In some particularly preferred embodiments, ratio of 1 or greater is desired.

Other means for determining the levels of production of a protein of interest e.g. a protease, in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). In some preferred embodiments, secretion of a protein of interest is higher in the altered strain obtained using the present invention than in a corresponding unaltered host. As known in the art, the altered *Bacillus* cells produced using the present invention are maintained and grown under conditions suitable for the expression and recovery of a polypeptide of interest from cell culture (See e.g., Hardwood and Cutting (eds.) *Molecular Biological Methods for Bacillus*, John Wiley & Sons [1990]). It is not intended that the present invention be limited to any particular assay method(s).

All publications and patents mentioned herein are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as should not be unduly limited to such specific embodiments. Indeed, various modifications of the described modes for carrying out the invention that are obvious to those skilled in the art and/or related fields are intended to be within the scope of the present invention.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ppm (parts per million); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); $OD_{280}$ (optical density at 280 nm); $OD_{600}$ (optical density at 600 nm); $A_{405}$ (absorbance at 405 nm); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); SDS (sodium dodecyl sulfate); Tris(tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); bME, BME and βME (beta-mercaptoethanol or 2-mercaptoethanol); Tris-HCl (tris[Hydroxymethyl] aminomethane-hydrochloride); Tricine (N-[tris-(hydroxymethyl)-methyl]-glycine); DMSO (dimethyl sulfoxide); Taq (*Thermus aquaticus* DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); DNA2.0 (DNA2.0, Menlo Park, Calif.); OXOID (Oxoid, Basingstoke, Hampshire, UK); Corning (Corning Life Sciences, Corning, N.Y.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Operon Technologies (Operon Technologies, Inc., Alameda, Calif.); Bachem (Bachem Bioscience, Inc., King of Prussia, Pa.); Difco (Difco Laboratories, Detroit, Mich.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); and Microsoft (Microsoft, Inc., Redmond, Wash.).

Example 1

Site-Scanning Mutagenesis of the SigP and Pro Sequence of the *Bacillus clausii* Alkaline Protease V049

Site-saturation mutagenesis of the pro sequence of the *Bacillus* clausii alkaline protease V049 precursor protease was performed using the QuikChange® site-directed mutagenesis kit (QC; Stratagene) according to the directions provided by the manufacturer. Site-saturation libraries were created to include modified polynucleotides sequences of the precursor polynucleotide encoding the *B. clausii* protease variant V049. The sequence encoding the pro region of the V049 polynucleotide contained in the pXX-V049 plasmid (FIGS. 5 and 6; SEQ ID NO:17) was mutated to produce a library of polynucleotides each comprising a mutation of one codon of the pro region of the precursor protease. Each codon of the pro region of V049 exemplified by NNG/C was mutated to be substituted by the 32 possible nucleotide triplets that encode the 20 naturally occurring amino acids. Complementary overlapping primers were designed for each codon of interest with 18 bases flanking the NNS codon, and the sequences of the primers (SEQ ID NO: 18-239) are given in Table 1.

TABLE 1

| Primer* | Primer Sequence | Bases left** | Bases right*** | SEQ ID NO |
|---|---|---|---|---|
| V049-1F | TTAAAAGGAGAGGGTAAAGANNSAGAAGCAAAAAATTGTG | 20 | 17 | 18 |
| V049-2F | GGAGAGGGTAAAGAGTGNNSAGCAAAAAATTGTGGATC | 17 | 18 | 19 |
| V049-3F | GAGGGTAAAGAGTGAGANNSAAAAAATTGTGGATCGTC | 17 | 18 | 20 |
| V049-4F | GGTAAAGAGTGAGAAGCNNSAAATTGTGGATCGTCGC | 17 | 17 | 21 |
| V049-5F | GTAAAGAGTGAGAAGCAAANNSTTGTGGATCGTCGCGTC | 19 | 17 | 22 |
| V049-6F | GAGTGAGAAGCAAAAAANNSTGGATCGTCGCGTCGAC | 17 | 17 | 23 |
| V049-7F | GTGAGAAGCAAAAAATTGNNSATCGTCGCGTCGACCGC | 18 | 17 | 24 |
| V049-8F | GAAGCAAAAAATTGTGGNNSGTCGCGTCGACCGCACTAC | 17 | 19 | 25 |
| V049-9F | GCAAAAAATTGTGGATCNNSGCGTCGACCGCACTACTC | 17 | 18 | 26 |
| V049-10F | CAAAAAATTGTGGATCGTCNNSTCGACCGCACTACTCATTTC | 19 | 20 | 27 |
| V049-11F | AAAAATTGTGGATCGTCGCGNNSACCGCACTACTCATTTC | 20 | 17 | 28 |
| V049-12F | AATTGTGGATCGTCGCGTCGNNSGCACTACTCATTTCTGTTG | 20 | 19 | 29 |
| V049-13F | GGATCGTCGCGTCGACCNNSCTACTCATTTCTGTTGC | 17 | 17 | 30 |
| V049-14F | GATCGTCGCGTCGACCGCANNSCTCATTTCTGTTGCTTTTAG | 19 | 20 | 31 |
| V049-15F | GTCGCGTCGACCGCACTANNSATTTCTGTTGCTTTTAG | 18 | 17 | 32 |
| V049-16F | CGTCGACCGCACTACTCNNSTCTGTTGCTTTTAGTTC | 17 | 17 | 33 |
| V049-17F | CGACCGCACTACTCATTNNSGTTGCTTTTAGTTCATC | 17 | 17 | 34 |
| V049-18F | CCGCACTACTCATTTCTNNSGCTTTTAGTTCATCGATC | 17 | 18 | 35 |
| V049-19F | CACTACTCATTTCTGTTNNSTTTAGTTCATCGATCGC | 17 | 17 | 36 |
| V049-20F | CTACTCATTTCTGTTGCTNNSAGTTCATCGATCGCATC | 18 | 17 | 37 |
| V049-21F | CTCATTTCTGTTGCTTTTNNSTCATCGATCGCATCGGC | 18 | 17 | 38 |
| V049-22F | CATTTCTGTTGCTTTTAGTNNSTCGATCGCATCGGCTGC | 19 | 17 | 39 |
| V049-23F | CTGTTGCTTTTAGTTCANNSATCGCATCGGCTGCTGAAG | 17 | 19 | 40 |
| V049-24F | GTTGCTTTTAGTTCATCGNNSGCATCGGCTGCTGAAGAAG | 18 | 19 | 41 |
| V049-25F | CTTTTAGTTCATCGATCNNSTCGGCTGCTGAAGAAGC | 17 | 17 | 42 |
| V049-26F | CTTTTAGTTCATCGATCGCANNSGCTGCTGAAGAAGCAAAAG | 20 | 19 | 43 |
| V049-27F | GTTCATCGATCGCATCGNNSGCTGAAGAAGCAAAAGAAAA | 17 | 20 | 44 |
| V049-28F | CATCGATCGCATCGGCTNNSGAAGAAGCAAAAGAAAAATA | 17 | 20 | 45 |
| V049-29F | CGATCGCATCGGCTGCTNNSGAAGCAAAAGAAAAATATTT | 17 | 20 | 46 |
| V049-30F | GATCGCATCGGCTGCTGAANNSGCAAAAGAAAAATATTTAAT | 19 | 20 | 47 |
| V049-31F | CATCGGCTGCTGAAGAANNSAAAGAAAAATATTTAATTG | 17 | 19 | 48 |
| V049-32F | CGGCTGCTGAAGAAGCANNSGAAAAATATTTAATTGG | 17 | 17 | 49 |
| V049-33F | CTGCTGAAGAAGCAAAANNSAAATATTTAATTGGCTTTAA | 17 | 20 | 50 |
| V049-34F | CTGAAGAAGCAAAAGAANNSTATTTAATTGGCTTTAATG | 17 | 19 | 51 |

TABLE 1-continued

| Primer* | Primer Sequence | Bases left** | Bases right*** | SEQ ID NO |
|---|---|---|---|---|
| V049-35F | GAAGAAGCAAAAGAAAAANNSTTAATTGGCTTTAATGAG | 18 | 18 | 52 |
| V049-36F | GAAGCAAAAGAAAAATATNNSATTGGCTTTAATGAGCAG | 18 | 18 | 53 |
| V049-37F | CAAAAGAAAAATATTTANNSGGCTTTAATGAGCAGGAAG | 17 | 19 | 54 |
| V049-38F | CAAAAGAAAAATATTTAATTNNSTTTAATGAGCAGGAAGC | 20 | 17 | 55 |
| V049-39F | GAAAAATATTTAATTGGCNNSAATGAGCAGGAAGCTGTC | 18 | 18 | 56 |
| V049-40F | AAAAATATTTAATTGGCTTTNNSGAGCAGGAAGCTGTCAG | 20 | 17 | 57 |
| V049-41F | AATATTTAATTGGCTTTAATNNSCAGGAAGCTGTCAGTGAG | 20 | 18 | 58 |
| V049-42F | ATTTAATTGGCTTTAATGAGNNSAAGCTGTCAGTGAGTTTG | 20 | 19 | 59 |
| V049-43F | TAATTGGCTTTAATGAGCAGNNSGCTGTCAGTGAGTTTGTAG | 20 | 19 | 60 |
| V049-44F | GCTTTAATGAGCAGGAANNSGTCAGTGAGTTTGTAGAAC | 17 | 19 | 61 |
| V049-45F | CTTTAATGAGCAGGAAGCTNNSAGTGAGTTTGTAGAACAAG | 19 | 19 | 62 |
| V049-46F | TTAATGAGCAGGAAGCTGTCNNSGAGTTTGTAGAACAAGTAG | 20 | 19 | 63 |
| V049-47F | GAGCAGGAAGCTGTCAGTNNSTTTGTAGAACAAGTAGAG | 18 | 18 | 64 |
| V049-48F | CAGGAAGCTGTCAGTGAGNNSGTAGAACAAGTAGAGGC | 18 | 17 | 65 |
| V049-49F | GAAGCTGTCAGTGAGTTTNNSGAACAAGTAGAGGCAAATG | 18 | 19 | 66 |
| V049-50F | CTGTCAGTGAGTTTGTANNSCAAGTAGAGGCAAATGAC | 17 | 18 | 67 |
| V049-51F | GTCAGTGAGTTTGTAGAANNSGTAGAGGCAAATGACGAG | 18 | 18 | 68 |
| V049-52F | GTGAGTTTGTAGAACAANNSGAGGCAAATGACGAGGTC | 17 | 18 | 69 |
| V049-53F | GAGTTTGTAGAACAAGTANNSGCAAATGACGAGGTCGC | 18 | 17 | 70 |
| V049-54F | GTTTGTAGAACAAGTAGAGNNSAATGACGAGGTCGCCATTC | 19 | 19 | 71 |
| V049-55F | GTAGAACAAGTAGAGGCANNSGACGAGGTCGCCATTCTC | 18 | 18 | 72 |
| V049-56F | GAACAAGTAGAGGCAAATNNSGAGGTCGCCATTCTCTC | 18 | 17 | 73 |
| V049-57F | CAAGTAGAGGCAAATGACNNSGTCGCCATTCTCTCTGAG | 18 | 18 | 74 |
| V049-58F | GTAGAGGCAAATGACGAGNNSGCAATTCTCTCTGAGGAAG | 18 | 19 | 75 |
| V049-59F | GAGGCAAATGACGAGGTCNNSATTCTCTCTGAGGAAGAG | 18 | 18 | 76 |
| V049-60F | CAAATGACGAGGTCGCCNNSCTCTCTGAGGAAGAGGAAG | 17 | 19 | 77 |
| V049-61F | CAAATGACGAGGTCGCCATTNNSTCTGAGGAAGAGGAAGTC | 20 | 18 | 78 |
| V049-62F | GACGAGGTCGCCATTCTCNNSGAGGAAGAGGAAGTCGAAAT | 18 | 20 | 79 |
| V049-63F | GAGGTCGCCATTCTCTCTNNSGAAGAGGAAGTCGAAATTG | 18 | 19 | 80 |
| V049-64F | GTCGCCATTCTCTCTGAGNNSGAGGAAGTCGAAATTGAATT | 18 | 20 | 81 |
| V049-65F | CCATTCTCTCTGAGGAANNSGAAGTCGAAATTGAATTG | 17 | 18 | 82 |
| V049-66F | CATTCTCTCTGAGGAAGAGNNSGTCGAAATTGAATTGCTTC | 19 | 19 | 83 |
| V049-67F | CTCTCTGAGGAAGAGGAANNSGAAATTGAATTGCTTCATG | 18 | 19 | 84 |
| V049-68F | CTGAGGAAGAGGAAGTCNNSATTGAATTGCTTCATGAATT | 17 | 20 | 85 |
| V049-69F | GAGGAAGAGGAAGTCGAANNSGAATTGCTTCATGAATTTG | 18 | 19 | 86 |
| V049-70F | GAAGAGGAAGTCGAAATTNNSTTGCTTCATGAATTTGAAAC | 18 | 20 | 87 |
| V049-71F | GAGGAAGTCGAAATTGAANNSCTTCATGAATTTGAAAC | 18 | 17 | 88 |
| V049-72F | GAAGTCGAAATTGAATTGNNSCATGAATTTGAAACGATTC | 18 | 19 | 89 |

TABLE 1-continued

| Primer* | Primer Sequence | Bases left** | Bases right*** | SEQ ID NO |
|---|---|---|---|---|
| V049-73F | GTCGAAATTGAATTGCTTNNSGAATTTGAAACGATTCC | 18 | 17 | 90 |
| V049-74F | GAAATTGAATTGCTTCATNNSTTTGAAACGATTCCTGTTTT | 18 | 20 | 91 |
| V049-75F | AAATTGAATTGCTTCATGAANNSGAAACGATTCCTGTTTTATC | 20 | 20 | 92 |
| V049-76F | GAATTGCTTCATGAATTTNNSACGATTCCTGTTTTATC | 18 | 17 | 93 |
| V049-77F | AATTGCTTCATGAATTTGAANNSATTCCTGTTTTATCCGTTG | 20 | 19 | 94 |
| V049-78F | CTTCATGAATTTGAAACGNNSCCTGTTTTATCCGTTGAG | 18 | 18 | 95 |
| V049-79F | CATGAATTTGAAACGATTNNSGTTTTATCCGTTGAGTTAAG | 18 | 20 | 96 |
| V049-80F | GAATTTGAAACGATTCCTNNSTTATCCGTTGAGTTAAG | 18 | 17 | 97 |
| V049-81F | AATTTGAAACGATTCCTGTTNNSTCCGTTGAGTTAAGCCC | 20 | 17 | 98 |
| V049-82F | GAAACGATTCCTGTTTTANNSGTTGAGTTAAGCCCAGAAG | 18 | 19 | 99 |
| V049-83F | CGATTCCTGTTTTATCCNNSGAGTTAAGCCCAGAAGATG | 17 | 19 | 100 |
| V049-84F | GATTCCTGTTTTATCCGTTNNSTTAAGCCCAGAAGATGTG | 19 | 18 | 101 |
| V049-85F | CTGTTTTATCCGTTGAGNNSAGCCCAGAAGATGTGGAC | 17 | 18 | 102 |
| V049-86F | GTTTTATCCGTTGAGTTANNSCCAGAAGATGTGGACGC | 18 | 17 | 103 |
| V049-87F | TTTTATCCGTTGAGTTAAGCNNSGAAGATGTGGACGCGCTTG | 20 | 19 | 104 |
| V049-88F | CCGTTGAGTTAAGCCCANNSGATGTGGACGCGCTTGAAC | 17 | 19 | 105 |
| V049-89F | GTTGAGTTAAGCCCAGAANNSGTGGACGCGCTTGAACTC | 18 | 18 | 106 |
| V049-90F | GAGTTAAGCCCAGAAGATNNSGACGCGCTTGAACTCGATC | 18 | 19 | 107 |
| V049-91F | GTTAAGCCCAGAAGATGTGNNSGCGCTTGAACTCGATCC | 19 | 17 | 108 |
| V049-92F | GCCCAGAAGATGTGGACNNSCTTGAACTCGATCCAGC | 17 | 17 | 109 |
| V049-93F | CAGAAGATGTGGACGCGNNSGAACTCGATCCAGCGATTTC | 17 | 20 | 110 |
| V049-94F | GAAGATGTGGACGCGCTTNNSCTCGATCCAGCGATTTC | 18 | 17 | 111 |
| V049-95F | GATGTGGACGCGCTTGAANNSGATCCAGCGATTTCTTATAT | 18 | 20 | 112 |
| V049-96F | GTGGACGCGCTTGAACTCNNSCCAGCGATTTCTTATATTG | 18 | 19 | 113 |
| V049-97F | GACGCGCTTGAACTCGATNNSGCGATTTCTTATATTGAAG | 18 | 19 | 114 |
| V049-98F | CGCTTGAACTCGATCCANNSATTTCTTATATTGAAGAG | 17 | 18 | 115 |
| V049-99F | CTTGAACTCGATCCAGCGNNSTCTTATATTGAAGAGGATG | 18 | 19 | 116 |
| V049-100F | GAACTCGATCCAGCGATTNNSTATATTGAAGAGGATGC | 18 | 17 | 117 |
| V049-101F | CTCGATCCAGCGATTTCTNNSATTGAAGAGGATGCAGAAG | 18 | 19 | 118 |
| V049-102F | GATCCAGCGATTTCTTATNNSGAAGAGGATGCAGAAGTAAC | 18 | 20 | 119 |
| V049-103F | CAGCGATTTCTTATATTNNSGAGGATGCAGAAGTAAC | 17 | 17 | 120 |
| V049-104F | CGATTTCTTATATTGAANNSGATGCAGAAGTAACGAC | 17 | 17 | 121 |
| V049-105F | GATTTCTTATATTGAAGAGNNSGCAGAAGTAACGACAATG | 19 | 18 | 122 |
| V049-106F | CTTATATTGAAGAGGATNNSGAAGTAACGACAATGGC | 17 | 17 | 123 |
| V049-107F | CTTATATTGAAGAGGATGCANNSGTAACGACAATGGCGCAATC | 20 | 20 | 124 |
| V049-108F | ATATTGAAGAGGATGCAGAANNSACGACAATGGCGCAATC | 20 | 17 | 125 |
| V049-109F | GAAGAGGATGCAGAAGTANNSACAATGGCGCAATCGGTAC | 18 | 19 | 126 |
| V049-110F | GAGGATGCAGAAGTAACGNNSATGGCGCAATCGGTACC | 18 | 17 | 127 |
| V049-111F | GATGCAGAAGTAACGACANNSGCGCAATCGGTACCATG | 18 | 17 | 128 |

TABLE 1-continued

| Primer* | Primer Sequence | Bases left** | Bases right*** | SEQ ID NO |
|---|---|---|---|---|
| V049-1R | CACAATTTTTTGCTTCTSNNTCTTTACCCTCTCCTTTTAA | 17 | 20 | 129 |
| V049-2R | GATCCACAATTTTTTGCTSNNCACTCTTTACCCTCTCC | 18 | 17 | 130 |
| V049-3R | GACGATCCACAATTTTTTSNNTCTCACTCTTTACCCTC | 18 | 17 | 131 |
| V049-4R | GCGACGATCCACAATTTSNNGCTTCTCACTCTTTACC | 17 | 17 | 132 |
| V049-5R | GACGCGACGATCCACAASNNTTTGCTTCTCACTCTTTAC | 17 | 19 | 133 |
| V049-6R | GTCGACGCGACGATCCASNNTTTTTTGCTTCTCACTC | 17 | 17 | 134 |
| V049-7R | GCGGTCGACGCGACGATSNNCAATTTTTTGCTTCTCAC | 17 | 18 | 135 |
| V049-8R | GTAGTGCGGTCGACGCGACSNNCCACAATTTTTTGCTTC | 19 | 17 | 136 |
| V049-9R | GAGTAGTGCGGTCGACGCSNNGATCCACAATTTTTTGC | 18 | 17 | 137 |
| V049-10R | GAAATGAGTAGTGCGGTCGASNNGACGATCCACAATTTTTTG | 20 | 19 | 138 |
| V049-11R | GAAATGAGTAGTGCGGTSNNCGCGACGATCCACAATTTTT | 17 | 20 | 139 |
| V049-12R | CAACAGAAATGAGTAGTGCSNNCGACGCGACGATCCACAATT | 19 | 20 | 140 |
| V049-13R | GCAACAGAAATGAGTAGSNNGGTCGACGCGACGATCC | 17 | 17 | 141 |
| V049-14R | CTAAAAGCAACAGAAATGAGSNNTGCGGTCGACGCGACGATC | 20 | 19 | 142 |
| V049-15R | CTAAAAGCAACAGAAATSNNTAGTGCGGTCGACGCGAC | 17 | 18 | 143 |
| V049-16R | GAACTAAAAGCAACAGASNNGAGTAGTGCGGTCGACG | 17 | 17 | 144 |
| V049-17R | GATGAACTAAAAGCAACSNNAATGAGTAGTGCGGTCG | 17 | 17 | 145 |
| V049-18R | GATCGATGAACTAAAAGCSNNAGAAATGAGTAGTGCGG | 18 | 17 | 146 |
| V049-19R | GCGATCGATGAACTAAAASNNAACAGAAATGAGTAGTG | 17 | 17 | 147 |
| V049-20R | GATGCGATCGATGAACTSNNAGCAACAGAAATGAGTAG | 17 | 18 | 148 |
| V049-21R | GCCGATGCGATCGATGASNNAAAAGCAACAGAAATGAG | 17 | 18 | 149 |
| V049-22R | GCAGCCGATGCGATCGASNNACTAAAAGCAACAGAAATG | 17 | 19 | 150 |
| V049-23R | CTTCAGCAGCCGATGCGATSNNTGAACTAAAAGCAACAG | 19 | 17 | 151 |
| V049-24R | CTTCTTCAGCAGCCGATGCSNNCGATGAACTAAAAGCAAC | 19 | 18 | 152 |
| V049-25R | GCTTCTTCAGCAGCCGASNNGATCGATGAACTAAAAG | 17 | 17 | 153 |
| V049-26R | CTTTTGCTTCTTCAGCAGCSNNTGCGATCGATGAACTAAAAG | 19 | 20 | 154 |
| V049-27R | TTTTCTTTTGCTTCTTCAGCSNNCGATGCGATCGATGAAC | 20 | 17 | 155 |
| V049-28R | TATTTTTCTTTTGCTTCTTCSNNAGCCGATGCGATCGATG | 20 | 17 | 156 |
| V049-29R | AAATATTTTCTTTTGCTTCSNNAGCAGCCGATGCGATCG | 20 | 17 | 157 |
| V049-30R | ATTAAATATTTTTCTTTTGCSNNTTCAGCAGCCGATGCGATC | 20 | 19 | 158 |
| V049-31R | CAATTAAATATTTTTCTTTSNNTTCTTCAGCAGCCGATG | 19 | 17 | 159 |
| V049-32R | CCAATTAAATATTTTTCSNNTGCTTCTTCAGCAGCCG | 17 | 17 | 160 |
| V049-33R | TTAAAGCCAATTAAATATTTSNNTTTTGCTTCTTCAGCAG | 20 | 17 | 161 |
| V049-34R | CATTAAAGCCAATTAAATASNNTTCTTTTGCTTCTTCAG | 19 | 17 | 162 |
| V049-35R | CTCATTAAAGCCAATTAASNNTTTTTCTTTTGCTTCTTC | 18 | 18 | 163 |
| V049-36R | CTGCTCATTAAAGCCAATSNNATATTTTTCTTTTGCTTC | 18 | 18 | 164 |
| V049-37R | CTTCCTGCTCATTAAAGCCSNNTAAATATTTTTCTTTTG | 19 | 17 | 165 |
| V049-38R | GCTTCCTGCTCATTAAAASNNAATTAAATATTTTTCTTTTG | 17 | 20 | 166 |

TABLE 1-continued

| Primer* | Primer Sequence | Bases left** | Bases right*** | SEQ ID NO |
|---|---|---|---|---|
| V049-39R | GACAGCTTCCTGCTCATTSNNGCCAATTAAATATTTTC | 18 | 18 | 167 |
| V049-40R | CTGACAGCTTCCTGCTCSNNAAAGCCAATTAAATATTTT | 17 | 20 | 168 |
| V049-41R | CTCACTGACAGCTTCCTGSNNATTAAAGCCAATTAAATATT | 18 | 20 | 169 |
| V049-42R | CAAACTCACTGACAGCTTCSNNCTCATTAAAGCCAATTAAAT | 19 | 20 | 170 |
| V049-43R | CTACAAACTCACTGACAGCSNNCTGCTCATTAAAGCCAATTA | 19 | 20 | 171 |
| V049-44R | GTTCTACAAACTCACTGACSNNTTCCTGCTCATTAAAGC | 19 | 17 | 172 |
| V049-45R | CTTGTTCTACAAACTCACTSNNAGCTTCCTGCTCATTAAAG | 19 | 19 | 173 |
| V049-46R | CTACTTGTTCTACAAACTCSNNGACAGCTTCCTGCTCATTAA | 19 | 20 | 174 |
| V049-47R | CTCTACTTGTTCTACAAASNNACTGACAGCTTCCTGCTC | 18 | 18 | 175 |
| V049-48R | GCCTCTACTTGTTCTACSNNCTCACTGACAGCTTCCTG | 17 | 18 | 176 |
| V049-49R | CATTTGCCTCTACTTGTTCSNNAAACTCACTGACAGCTTC | 19 | 18 | 177 |
| V049-50R | GTCATTTGCCTCTACTTGSNNTACAAACTCACTGACAG | 18 | 17 | 178 |
| V049-51R | CTCGTCATTTGCCTCTACSNNTTCTACAAACTCACTGAC | 18 | 18 | 179 |
| V049-52R | GACCTCGTCATTTGCCTCSNNTTGTTCTACAAACTCAC | 18 | 17 | 180 |
| V049-53R | GCGACCTCGTCATTTGCSNNTACTTGTTCTACAAACTC | 17 | 18 | 181 |
| V049-54R | GAATGGCGACCTCGTCATTSNNCTCTACTTGTTCTACAAAC | 19 | 19 | 182 |
| V049-55R | GAGAATGGCGACCTCGTCSNNTGCCTCTACTTGTTCTAC | 18 | 18 | 183 |
| V049-56R | GAGAGAATGGCGACCTCSNNATTTGCCTCTACTTGTTC | 17 | 18 | 184 |
| V049-57R | CTCAGAGAGAATGGCGACSNNGTCATTTGCCTCTACTTG | 18 | 18 | 185 |
| V049-58R | CTTCCTCAGAGAGAATGGCSNNCTCGTCATTTGCCTCTAC | 19 | 18 | 186 |
| V049-59R | CTCTTCCTCAGAGAGAATSNNGACCTCGTCATTTGCCTC | 18 | 18 | 187 |
| V049-60R | CTTCCTCTTCCTCAGAGAGSNNGGCGACCTCGTCATTTG | 19 | 17 | 188 |
| V049-61R | GACTTCCTCTTCCTCAGASNNAATGGCGACCTCGTCATTTG | 18 | 20 | 189 |
| V049-62R | ATTTCGACTTCCTCTTCCTCSNNGAGAATGGCGACCTCGTC | 20 | 18 | 190 |
| V049-63R | CAATTTCGACTTCCTCTTCSNNAGAGAGAATGGCGACCTC | 19 | 18 | 191 |
| V049-64R | AATTCAATTTCGACTTCCTCSNNCTCAGAGAGAATGGCGAC | 20 | 18 | 192 |
| V049-65R | CAATTCAATTTCGACTTCSNNTTCCTCAGAGAGAATGG | 18 | 17 | 193 |
| V049-66R | GAAGCAATTCAATTTCGACSNNCTCTTCCTCAGAGAGAATG | 19 | 19 | 194 |
| V049-67R | CATGAAGCAATTCAATTTCSNNTTCCTCTTCCTCAGAGAG | 19 | 18 | 195 |
| V049-68R | AATTCATGAAGCAATTCAATSNNGACTTCCTCTTCCTCAG | 20 | 17 | 196 |
| V049-69R | CAAATTCATGAAGCAATTCSNNTTCGACTTCCTCTTCCTC | 19 | 18 | 197 |
| V049-70R | GTTTCAAATTCATGAAGCAASNNAATTTCGACTTCCTCTTC | 20 | 18 | 198 |
| V049-71R | GTTTCAAATTCATGAAGSNNTTCAATTTCGACTTCCTC | 17 | 18 | 199 |
| V049-72R | GAATCGTTTCAAATTCATGSNNCAATTCAATTTCGACTTC | 19 | 18 | 200 |
| V049-73R | GGAATCGTTTCAAATTCSNNAAGCAATTCAATTTCGAC | 17 | 18 | 201 |
| V049-74R | AAAACAGGAATCGTTTCAAASNNATGAAGCAATTCAATTTC | 20 | 18 | 202 |
| V049-75R | GATAAAACAGGAATCGTTTCSNNTTCATGAAGCAATTCAATTT | 20 | 20 | 203 |
| V049-76R | GATAAAACAGGAATCGTSNNAAATTCATGAAGCAATTC | 17 | 18 | 204 |
| V049-77R | CAACGGATAAAACAGGAATSNNTTCAAATTCATGAAGCAATT | 19 | 20 | 205 |

TABLE 1-continued

| Primer* | Primer Sequence | Bases left** | Bases right*** | SEQ ID NO |
|---|---|---|---|---|
| V049-78R | CTCAACGGATAAAACAGGSNNCGTTTCAAATTCATGAAG | 18 | 18 | 206 |
| V049-79R | CTTAACTCAACGGATAAAACSNNAATCGTTTCAAATTCATG | 20 | 18 | 207 |
| V049-80R | CTTAACTCAACGGATAASNNAGGAATCGTTTCAAATTC | 17 | 18 | 208 |
| V049-81R | GGGCTTAACTCAACGGASNNACAGGAATCGTTTCAAATT | 17 | 20 | 209 |
| V049-82R | CTTCTGGGCTTAACTCAACSNNTAAAACAGGAATCGTTTC | 19 | 18 | 210 |
| V049-83R | CATCTTCTGGGCTTAACTCSNNGGATAAAACAGGAATCG | 19 | 17 | 211 |
| V049-84R | CACATCTTCTGGGCTTAASNNACGGATAAAACAGGAATC | 18 | 19 | 212 |
| V049-85R | GTCCACATCTTCTGGGCTSNNCTCAACGGATAAAACAG | 18 | 17 | 213 |
| V049-86R | GCGTCCACATCTTCTGGSNNTAACTCAACGGATAAAAC | 17 | 18 | 214 |
| V049-87R | CAAGCGCGTCCACATCTTCSNNGCTTAACTCAACGGATAAAA | 19 | 20 | 215 |
| V049-88R | GTTCAAGCGCGTCCACATCSNNTGGGCTTAACTCAACGG | 19 | 17 | 216 |
| V049-89R | GAGTTCAAGCGCGTCCACSNNTTCTGGGCTTAACTCAAC | 18 | 18 | 217 |
| V049-90R | GATCGAGTTCAAGCGCGTCSNNATCTTCTGGGCTTAACTC | 19 | 18 | 218 |
| V049-91R | GGATCGAGTTCAAGCGCSNNCACATCTTCTGGGCTTAAC | 17 | 19 | 219 |
| V049-92R | GCTGGATCGAGTTCAAGSNNGTCCACATCTTCTGGGC | 17 | 17 | 220 |
| V049-93R | GAAATCGCTGGATCGAGTTCSNNCGCGTCCACATCTTCTG | 20 | 17 | 221 |
| V049-94R | GAAATCGCTGGATCGAGSNNAAGCGCGTCCACATCTTC | 17 | 18 | 222 |
| V049-95R | ATATAAGAAATCGCTGGATCSNNTCAAGCGCGTCCACATC | 20 | 18 | 223 |
| V049-96R | CAATATAAGAAATCGCTGGSNNGAGTTCAAGCGCGTCCAC | 19 | 18 | 224 |
| V049-97R | CTTCAATATAAGAAATCGCSNNATCGAGTTCAAGCGCGTC | 19 | 18 | 225 |
| V049-98R | CTCTTCAATATAAGAAATSNNTGGATCGAGTTCAAGCG | 18 | 17 | 226 |
| V049-99R | CATCCTCTTCAATATAAGASNNCGCTGGATCGAGTTCAAG | 19 | 18 | 227 |
| V049-100R | GCATCCTCTTCAATATASNNAATCGCTGGATCGAGTTC | 17 | 18 | 228 |
| V049-101R | CTTCTGCATCCTCTTCAATSNNAGAAATCGCTGGATCGAG | 19 | 18 | 229 |
| V049-102R | GTTACTTCTGCATCCTCTTCSNNATAAGAAATCGCTGGATC | 20 | 18 | 230 |
| V049-103R | GTTACTTCTGCATCCTCSNNAATATAAGAAATCGCTG | 17 | 17 | 231 |
| V049-104R | GTCGTTACTTCTGCATCSNNTTCAATATAAGAAATCG | 17 | 17 | 232 |
| V049-105R | CATTGTCGTTACTTCTGCSNNCTCTTCAATATAAGAAATC | 18 | 19 | 233 |
| V049-106R | GCCATTGTCGTTACTTCSNNATCCTCTTCAATATAAG | 17 | 17 | 234 |
| V049-107R | GATTGCGCCATTGTCGTTACSNNTGCATCCTCTTCAATATAAG | 20 | 20 | 235 |
| V049-108R | GATTGCGCCATTGTCGTSNNTTCTGCATCCTCTTCAATAT | 17 | 20 | 236 |
| V049-109R | GTACCGATTGCGCCATTGTSNNTACTTCTGCATCCTCTTC | 19 | 18 | 237 |
| V049-110R | GGTACCGATTGCGCCATSNNCGTTACTTCTGCATCCTC | 17 | 18 | 238 |
| V049-111R | CATGGTACCGATTGCGCSNNTGTCGTTACTTCTGCATC | 17 | 18 | 239 |

*The primer names provided reflect the amino acid position of the substitution; "R" indicates that the primer is the reverse primer and "F" indicates that the primer is a forward primer. For example, V049-108F is the forward primer that was used in the substitution of amino acid at position 108 of the V049 precursor protease.

"Bases left" and *"Bases Right" indicate the number of bases to the left and to the right of the mutating codon that are present in the primer. These bases are complementary to the bases of the template precursor polynucleotide bases (i.e. V049).

```
Polynucleotide sequence of vector pXX-049
                                       SEQ ID NO: 17
AATTCCTCCATTTTCTTCTGCTATCAAAATAACAGACTCGTGATTTTC

CAAACGAGCTTTCAAAAAAGCCTCTGCCCCTTGCAAATCGGATGCCTG

TCTATAAAATTCCCGATATTGGCTTAAACAGCGGCGCAATGGCGGCCG

CATCTGATGTCTTTGCTTGGCGAATGTTCATCTTATTTCTTCCTCCCT

CTCAATAATTTTTTCATTCTATCCCTTTTCTGTAAAGTTTATTTTTCA

GAATACTTTTATCATCATGCTTTGAAAAAATATCACGATAATATCCAT

TGTTCTCACGGAAGCACACGCAGGTCATTTGAACGAATTTTTTCGACA

GGAATTTGCCGGGACTCAGGAGCATTTAACCTAAAAAGCATGACATT

TCAGCATAATGAACATTTACTCATGTCTATTTTCGTTCTTTTCTGTAT

GAAAATAGTTATTTCGAGTCTCTACGGAAATAGCGAGAGATGATATAC

CTAAATAGAGATAAAATCATCTCAAAAAAATGGGTCTACTAAAATATT

ATTCCATCTATTACAATAAATTCACAGAATAGTCTTTTAAGTAAGTCT

ACTCTGAATTTTTTAAAAGGAGAGGGTAAAGAGTGAGAAGCAAAAAA

TTGTGGATCGTCGCGTCGACCGCACTACTCATTTCTGTTGCTTTTAGT

TCATCGATCGCATCGGCTGCTGAAGAAGCAAAAGAAAAATATTTAATT

GGCTTTAATGAGCAGGAAGCTGTCAGTGAGTTTGTAGAACAAGTAGAG

GCAAATGACGAGGTCGCCATTCTCTCTGAGGAAGAGGAAGTCGAAATT

GAATTGCTTCATGAATTTGAAACGATTCCTGTTTTATCCGTTGAGTTA

AGCCCAGAAGATGTGGACGCGCTTGAACTCGATCCAGCGATTTCTTAT

ATTGAAGAGGATGCAGAAGTAACGACAATGGCGCAATCGGTACCATGG

GGAATTAGCCGTGTGCAAGCCCCAGCTGCCCATAACCGTGGATTGACA

GGTTCTGGTGTAAAAGTTGCTGTCCTCGATACAGGTATTTCCACTCAT

CCAGACTTAAATATTCGTGGTGGCGCTAGCTTTGTACCAGGGGAACCA

TCCACTCAAGATGGGAATGGGCATGGCACGCATGTGGCTGGGACGATT

GCTGCTTTAAACAATTCGATTGGCGTTCTTGGCGTAGCACCGAACGCG

GAACTATACGCTGTTAAAGTATTAGGGGCGAGCGGTTCAGGTTCGGTC

AGCTCGATTGCCCAAGGATTGGAATGGGCAGGGAACAATGTTATGCAC

GTTGCTAATTTGAGTTTAGGACTGCAGGCACCAAGTGCCACACTTGAG

CAAGCTGTTAATAGCGCGACTTCTAGAGGCGTTCTTGTTGTAGCGGCA

TCTGGGAATTCAGGTGCAGGCTCAATCAGCTATCCGGCCCGTTATGCG

AACGCAATGGCAGTCGGAGCTACTGACCAAAACAACAACCGCGCCAGC

TTTTCACAGTATGGCGCAGGGCTTGACATTGTCGCACCAGGTGTAAAC

GTGCAGAGCACATACCCAGGTTCAACGTATGCCAGCTTAAACGGTACA

TCGATGGCTACTCCTCATGTTGCAGGTGCAGCAGCCCTTGTTAAACAA

AAGAACCCATCTTGGTCCAATGTACAAATCCGCAATCATCTAAAGAAT

ACGGCAACGAGCTTAGGAAGCACGAACTTGTATGGAAGCGGACTTGTC

AATGCAGAAGCGGCAACACGTTAATCAATAAAAAAACGCTGTGCGGTT

AAAGGGCACAGCGTTTTTTTGTGTATGAATCGGGATCCTCGATCGAGA

CTAGAGTCGATTTTTACAAGAATTAGCTTTATATAATTTCTGTTTTTC

TAAAGTTTTATCAGCTACAAAAGACAGAAATGTATTGCAATCTTCAAC

TAAATCCATTTGATTCTCTCCAATATGACGTTTAATAAATTTCTGAAA

TACTTGATTTCTTTGTTTTTTCTCAGTATACTTTTCCATGTTATAACA

CATAAAAACAACTTAGTTTTCACAAACTATGACAATAAAAAAAGTTGC

TTTTTCCCCTTTCTATGTATGTTTTTTACTAGTCATTTAAAACGATAC

ATTAATAGGTACGAAAAAGCAACTTTTTTTGCGCTTAAAACCAGTCAT

ACCAATAACTTAAGGGTAACTAGCCTCGCCGGCAATAGTTACCCTTAT

TATCAAGATAAGAAAGAAAAGGATTTTTCGCTACGCTCAAATCCTTTA

AAAAAACACAAAAGACCACATTTTTTAATGTGGTCTTTATTCTTCAAC

TAAAGCACCCATTAGTTCAACAAACGAAAATTGGATAAAGTGGGATAT

TTTTAAAATATATATTTATGTTACAGTAATATTGACTTTTAAAAAAGG

ATTGATTCTAATGAAGAAAGCAGACAAGTAAGCCTCCTAAATTCACTTT

AGATAAAAATTTAGGAGGCATATCAAATGAACTTTAATAAAATTGATT

TAGACAATTGGAAGAGAAAAGAGATATTTAATCATTATTTGAACCAAC

AAACGACTTTTAGTATAACCACAGAAATTGATATTAGTGTTTTATACC

GAAACATAAAACAAGAAGGATATAAATTTTACCCTGCATTTATTTTCT

TAGTGACAAGGGTGATAAACTCAAATACAGCTTTTAGAACTGGTTACA

ATAGCGACGGAGAGTTAGGTTATTGGGATAAGTTAGAGCCACTTTATA

CAATTTTTGATGGTGTATCTAAAACATTCTCTGGTATTTGGACTCCTG

TAAAGAATGACTTCAAAGAGTTTTATGATTTATACCTTTCTGATGTAG

AGAAATATAATGGTTCGGGGAAATTGTTTCCCAAAACACCTATACCTG

AAAATGCTTTTTCTCTTTCTATTATTCCATGGACTTCATTTACTGGGT

TTAACTTAAATATCAATAATAATAGTAATTACCTtCTACCCATTATTA

CAGCAGGAAAATTCATTAATAAAGGTAATTCAATATATTTACCGCTAT

CTTTACAGGTACATCATTCTGTTTGTGATGGTTATCATGCAGGATTGT

TTATGAACTCTATTCAGGAATTGTCAGATAGGCCTAATGACTGGCTTT

TATAATATGAGATAATGCCGACTGTACTTTTTACAGTCGGTTTTCTAA

TGTCACTAACCTGCCCCGTTAGTTGAAGAAGGTTTTTATATTACAGCT

CCAGATCCATATCCTTCTTTTTCTGAACCGACTTCTCCTTTTTCGCTT

CTTTATTCCAATTGCTTTATTGACGTTGAGCCTCGGAACCCTTAACAA

TCCCAAACTTGTCGAATGGTCGGCTTAATAGCTCACGCTATGCCGAC

ATTCGTCTGCAAGTTTAGTTAAGGGTTCTTCTCAACGCACAATAAATTT

TCTCGGCATAAATGCGTGGTCTAATTTTTATTTTTAATAACCTTGATAG
```

```
CAAAAAATGCCATTCCAATACAAAACCACATACCTATAATCGACCTGCA
GGAATTAATTCCTCCATTTTCTTCTGCTATCAAAATAACAGACTCGTGA
TTTTCCAAACGAGCTTTCAAAAAAGCCTCTGCCCCTTGCAAATCGGATG
CCTGTCTATAAAATTCCCGATATTGGCTTAAACAGCGGCGCAATGGCGG
CCGCATCTGATGTCTTTGCTTGGCGAATGTTCATCTTATTTCTTCCTCC
CTCTCAATAATTTTTTCATTCTATCCCTTTTCTGTAAAGTTTATTTTTC
AGAATACTTTTATCATCATGCTTTGAAAAAATATCACGATAATATCCAT
TGTTCTCACGGAAGCACACGCAGGTCATTTGAACGAATTTTTTCGACAG
GAATTTGCCGGGACTCAGGAGCATTTAACCTAAAAAAGCATGACATTTC
AGCATAATGAACATTTACTCATGTCTATTTTCGTTCTTTTCTGTATGAA
AATAGTTATTTCGAGTCTCTACGGAAATAGCGAGAGATGATATACCTAA
ATAGAGATAAAATCATCTCAAAAAAATGGGTCTACTAAAATATTATTCC
ATCTATTACAATAAATTCACAGAATAGTCTTTTAAGTAAGTCTACTCTG
AATTTTTTTATCAAGCTAGCTTGGCGTAATCATGGTCATAGCTGTTTCC
TGTGTGAAATTGTTATCCGCTCACAATTCCACACAACATACGAGCCGGA
AGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTG
CCAGCTGCATTAATGAATCGGCCAACGCGCGGGAGAGGCGGTTTGCGG
GTATTGCGCTCTTCCGCTTCCTCGCTCACTGACTCGCTGCGCTCGGTCG
TTCGGGCGAGCGGTATCAGCTCACTCAAAGGCGGTAATACGGTTATCT
GCCCACAGAATCAGGGGATAACGCAGGAAAGAACATGTGAGCAAAAGGC
CAGCAAAAGGCCAGGAACCGTAAAAAGGCCGCGTTGCTGGCGTTTTTCC
ATAGGCTCCGCCCCCTGACGAGCATCACAAAAATCGACGCTCAAGTCA
GAGGTGGCGAAACCCGACAGGACTATAAAGATACCAGGCGTTTCCCCCT
GGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTA
ACTATCGTCTTGAGTCCAACCCGGTAAGACACGACTTATCGCCACTGGC
AGCAGCCACTGGTAACAGGATTAGCAGAGCGAGGTATGTAGGCGGTGCT
ACAGAGTTCTTGAAGCTAACTACGGCTACACTAGAAGGTGGTGGGACAG
TATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCA
CGTTAAGGGATTTTGGTCATGAGATTATCAAAAAGGATCTTCACCTAGAT
CCTTTTAAATTAAAAATGAAGTTTTAAATCAATCTAAAGTATATATGAGT
AAACTTGGTCTGACAGTTACCAATGCTTAATCAGTGAGGCACCTATCTC
AGCGATCTGTCTATTTCGTTCATCCATAGTTGCCTGACTCCCCGTCGTGT
AGATAACTACGATACGGGAGGGCTTACCATCTGGCCCCAGTGCTGCAAT
GATACCGCGAGACCCACGCTCACCGGCTCCAGATTTATCAGCAATAAACCA
GCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACG
CTCGTCGTTTGGTATGGCTTCATTCAGCTCCGGTTCCCAACGATCAAGGCG
AGTTACATGATCCCCCATGTTGTGCAAAAAAGCGGTTAGCTCCTTCGGTCC
TCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTC
TGTGACTGGTGAGTACTCAACCAAGTCATTCTGAGAATAGTGTATGCGGCG
ACCGAGTTGCTCTTGCCCGGCGTCAATACGGGATAATACCGCGCCACATAG
CAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGC
ACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGA
AATGTTGAATACTCATACTCTTCCTTTTTCAATATTATTGAAGCATTTATC
AGGGTTATTGTCTCATGAGCGGATACATATTTGAATGTATTTAGAAAAATA
AACAAATAGGGGTTCCGCGCACATTTCCCCGAAACTGACGTCTAAGAAAC
CATTATTATCATGACATTAACCTATAAAAATAGGCGTAGTGCCACATCAC
GAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGC
TGGCTTAACTATGCGGCATCAGAGCAGATTGTACTGAGAGTGCACCATAT
GCGGTGTGAAATACCGCACAGATGCGTAAGGAGAAAATACCGCATCAGGCG
CCATTCGCCTTCAAGGCTGCGCAACTGTTGGGAAGGGCGATCGGTGCGGGC
CTCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGGC
CAGTG
```

The QC reaction consisted of 40.25 μL of sterile distilled H$_2$O, 5 μL of PfuTurbo 10× buffer from the kit, 1 μL dNTPs from the kit, 1.25 μL of forward primer (100 ng/μL), 1.25 μL reverse primer (100 ng/μL), 0.25 μL of pMSAT-NcoI miniprep DNA as template (~50 ng), and 1 μL of PfuTurbo from the kit, for a total of 50 μL. The cycling conditions were 95° C. for 1 min, once, followed by 19-20 cycles of 95° C. for 1 min., 55° C. for 1 min, and 68° C. for 12 min. To analyze the reaction, 5 μL of the reaction was run on a 1.2% E-gel (Invitrogen) upon completion. Next, DpnI digestion was carried out twice sequentially, with 1 μL and 1 μL of enzyme at 37° C. for 2 to 8 hours. A negative control was carried out under similar conditions, but without any primers. Then, 1 μL of the DpnI-digested reaction product was transformed into 50 μL of one-shot TOP10 electrocompetent cells (Invitrogen) using a BioRad electroporator. Then, 1 ml of SOC provided with the TOP10 cells (Invitrogen) were added to the electroporated cells and incubated with shaking for 1 hour before plating on LA plates containing 5 ppm chloramphenicol. The plates were incubated at 37° C. overnight. After this incubation, 96 colonies from each of the libraries (i.e., each site) were inoculated in 200 μL of LB containing 10-50 ppm of Chloramphenicol in 96-well microtiter plates and grow overnight at 37° C. The plates were frozen at −80° C. after addition of glycerol to 20% final concentration the next day, and they were used for high throughput sequencing with the V049SEQ-R2 primers.

Similarly, mutations of codons encoding two or more amino acids of the pro region of the precursor protease V049 are performed using the QuikChange® Multi Site-Directed mutagenesis (QCMS; Stratagene). The QCMS reaction is performed using 19.25 µL of sterile distilled H2O, 2.5 µL of 10× buffer from the kit, 1 µL dNTPs from the kit, 1 µL of 5' phosphorylated forward primer (100 ng/µL), 0.25 µL of pMSAT-NcoI miniprep DNA as template (~50 ng), and 1 µL of the enzyme blend from the kit for a total of 25 µL. The cycling conditions are 95° C. for 1 min once, followed by 30 cycles of 95° C. for 1 min, 55° C. for 1 min, and 65° C. for 12 min. To analyze the reaction product, 2.5 µL of the reaction are run on a 1.2% E-gel (Invitrogen) upon completion. Next, DpnI digestion is carried out twice sequentially, with 1 ul and then 0.5 µL of enzyme at 37° C. for 2 to 8 hours. The controls, transformation, and sequencing are performed as for the QC method described above.

Example 2

Host Cell Transformation and Expression of Modified Proteases

Plasmids pXX-049 containing polynucleotides encoding the modified proteins of interest were digested twice with DpnI for 3-5 hours at 37 C.

Transformation and Screening in *E. coli*

1 ul of DpnI digested plasmid DNA was used to transform *E. coli* Top10 cells by electroporation. The transformed cells were plated onto LB agar plates containing 5 ppm CMP (chloramphenicol), and colonies were allowed to grow overnight. 96 individual colonies were picked and transferred to corresponding wells of a 96-well micro-titer plate containing LB+5 ppm CMP+50 ppm carbenicillin. Cultures were grown overnight at 37° C. while shaking at 250 rpm. Glycerol stock was added in the culture to a final concentration of 10%. Plasmid DNA was prepared from the 96 *E. coli* cultures, and a portion of the plasmid DNA preparation was sequenced (Cogenics, Morrisville, N.C.). Automated sequence analysis was performed using Phrep, Phrap, Consed, Custal W software.

Transformation into *Bacillus subtilis*

A second portion of the plasmid DNA was used to transform *B. subtilis* host cells. Two microliters of plasmid DNA from each of the 96 *E. coli* cultures carrying the appropriate mutations were used to transform 100 ul of *B. subtilis* ComK competent cells. The cells were incubated at 37° C. for 45 minutes while shaking at 250 rpm. Cells from the 96 transformation mixture were plated onto LA containing 1.6% skim milk and 5 ppm CMP and incubated overnight in at 37° C. incubator.

Four colonies, from each of the 96 transformations, were picked and individually transferred to a micro-titer plate containing 150 ul of LB and 5 ppm CMP per well. A number of wells of the micro-titer plate contained the appropriate controls. The micro-titer plates were then incubated for four hours at 37° C. while rotating at 250 rpm. 10 ul of each of the cultures were transferred to a new micro-titer plate containing 140 ul of Grant II media+5 ppm CMP, pH 7.3. GrantII media was prepared as follows: Solution I: 10 g of Soytone were dissolved in 500 ml water and autoclaved for 20-25 minutes; Solution II: 3 ml of 1M K2HPO4, 75 g glucose, 3.6 g urea, 100 ml Grant's 10× MOPS were diluted into 400 ml water. Solutions I and II were mixed and the pH adjusted to pH7.3 with HCl/NaOH. The final volume was adjusted to 1 L, and the final solution was sterilized through 0.22-um PES filter.

The micro-titer plate cultures were incubated in shaker at 37° C., 250 rpm. Samples were taken at regular intervals (up to 40 hours) for assay analysis.

Example 3

Measurement of Modified Protease Production: AAPF Assay of Protease Activity

Each of the *B. subtilis* cultures obtained as described in Example 2, was assayed for the production of the modified proteases. The enzymes produced were assayed for activity against the substrate, succinyl -L-Ala-L-Ala-L-Pro-L-Phe-p-nitroanalide (AAPF). The assay measured the production of modified protease as the increase in absorbance at 405 nm/min resulting from the hydrolysis and release of p-nitroanaline (Estell et al., J Biol. Chem., 260:6518-6521 (1985)). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds. Ten microliters of each of the *B. subtilis* cultures were diluted 100 ul of Tris Buffer, containing 10 mM Tris+ 0.005% TWEEN®-80, pH 8.6; and 25 ul of 100 mg/ml AAPF. The relative activity of each of the modified proteases was calculated, and the effect of each amino acid substitution on the production of the corresponding modified protease was determined as a ratio of the activity of the mature protease processed from each modified protease to the activity of the mature protease processed from the unmodified V049 precursor protease. The results are given in Table 2.

Once the DNA construct was stably integrated into a competent *Bacillus subtilis* strain, the activity of the modified proteases was measured in microtiter assays and the activity was compared to the activity of the corresponding precursor protease.

Ten microliters of overnight Grant II Media cell cultures were diluted to 100 ul of Tris Buffer, containing 10 mM Tris+0.005% TWEEN®-80 pH 8.6; and 25 ul of 100 mg/ml AAPF substrate were used to assay for protease activity. Assays were done in microtiter plates and the Softmax Pro Software was used.

The results showed that amino acid substitution of most of the amino acids of the precursor V049 protease lead to an enhanced production of the mature form of the protease. In addition, site saturation of each of the substituted amino acids showed that each amino acid can be substituted by two or more amino acids at the same position to increase the production of the mature form relative to that obtained from the precursor protease having unmodified pro region.

TABLE 2

| POSITION* | VARIANT CODE | VARIANT AMINO ACID | PROTEIN CONCENTRATION | ACTIVITY RATIO# |
|---|---|---|---|---|
| 1 | V001D | D | 102.37 | 1.02 |
| 1 | V001Q | Q | 98.52 | 0.99 |
| 1 | V001F | F | 96.85 | 0.97 |
| 1 | V001L | L | 58.70 | 0.59 |
| 1 | V001A | A | 58.67 | 0.59 |

TABLE 2-continued

| POSITION* | VARIANT CODE | VARIANT AMINO ACID | PROTEIN CONCENTRATION | ACTIVITY RATIO# |
|---|---|---|---|---|
| 1 | V001H | H | 36.54 | 0.37 |
| 1 | V001I | I | 35.67 | 0.36 |
| 1 | V001G | G | 29.93 | 0.30 |
| 1 | V001Y | Y | 14.97 | 0.15 |
| 1 | V001E | E | 9.30 | 0.09 |
| 1 | V001T | T | 6.99 | 0.07 |
| 1 | V001C | C | 6.75 | 0.07 |
| 1 | V001W | W | 6.61 | 0.07 |
| 1 | V001S | S | 5.54 | 0.06 |
| 1 | V001R | R | 5.19 | 0.05 |
| 2 | R002M | M | 122.01 | 1.22 |
| 2 | R002W | W | 104.55 | 1.05 |
| 2 | R002K | K | 103.46 | 1.03 |
| 2 | R002C | C | 101.20 | 1.01 |
| 2 | R002S | S | 101.19 | 1.01 |
| 2 | R002L | L | 98.36 | 0.98 |
| 2 | R002F | F | 93.71 | 0.94 |
| 2 | R002H | H | 93.65 | 0.94 |
| 2 | R002N | N | 89.23 | 0.89 |
| 2 | R002A | A | 82.16 | 0.82 |
| 2 | R002G | G | 73.95 | 0.74 |
| 2 | R002D | D | 60.97 | 0.61 |
| 2 | R002V | V | 53.99 | 0.54 |
| 2 | R002T | T | 40.33 | 0.40 |
| 2 | R002Y | Y | 13.66 | 0.14 |
| 3 | S003F | F | 133.20 | 1.33 |
| 3 | S003M | M | 127.94 | 1.28 |
| 3 | S003R | R | 121.00 | 1.21 |
| 3 | S003T | T | 116.45 | 1.16 |
| 3 | S003Q | Q | 114.41 | 1.14 |
| 3 | S003N | N | 105.57 | 1.06 |
| 3 | S003I | I | 104.04 | 1.04 |
| 3 | S003V | V | 101.09 | 1.01 |
| 3 | S003W | W | 99.63 | 1.00 |
| 3 | S003G | G | 99.50 | 0.99 |
| 3 | S003D | D | 98.94 | 0.99 |
| 3 | S003H | H | 98.52 | 0.99 |
| 3 | S003A | A | 97.60 | 0.98 |
| 3 | S003P | P | 93.74 | 0.94 |
| 3 | S003Y | Y | 65.38 | 0.65 |
| 3 | S003L | L | 48.58 | 0.49 |
| 3 | S003C | C | 10.43 | 0.10 |
| 4 | K004T | T | 121.17 | 1.21 |
| 4 | K004V | V | 116.61 | 1.17 |
| 4 | K004Y | Y | 111.33 | 1.11 |
| 4 | K004I | I | 109.36 | 1.09 |
| 4 | K004C | C | 109.34 | 1.09 |
| 4 | K004R | R | 107.32 | 1.07 |
| 4 | K004F | F | 103.89 | 1.04 |
| 4 | K004H | H | 96.72 | 0.97 |
| 4 | K004A | A | 95.03 | 0.95 |
| 4 | K004Q | Q | 92.30 | 0.92 |
| 4 | K004P | P | 91.49 | 0.91 |
| 4 | K004N | N | 86.73 | 0.87 |
| 4 | K004S | S | 78.31 | 0.78 |
| 4 | K004G | G | 53.68 | 0.54 |
| 4 | K004E | E | 29.18 | 0.29 |
| 4 | K004L | L | 7.86 | 0.08 |
| 5 | K005W | W | 123.75 | 1.24 |
| 5 | K005N | N | 118.59 | 1.19 |
| 5 | K005Q | Q | 114.87 | 1.15 |
| 5 | K005Y | Y | 112.41 | 1.12 |
| 5 | K005V | V | 112.29 | 1.12 |
| 5 | K005H | H | 111.16 | 1.11 |
| 5 | K005G | G | 110.84 | 1.11 |
| 5 | K005S | S | 109.37 | 1.09 |
| 5 | K005D | D | 108.39 | 1.08 |
| 5 | K005C | C | 103.96 | 1.04 |
| 5 | K005R | R | 100.76 | 1.01 |
| 5 | K005T | T | 99.54 | 1.00 |
| 5 | K005A | A | 91.66 | 0.92 |
| 5 | K005L | L | 90.96 | 0.91 |
| 5 | K005P | P | 49.40 | 0.49 |
| 5 | K005F | F | 6.26 | 0.06 |
| 5 | K005M | M | 5.65 | 0.06 |
| 6 | L006M | M | 122.55 | 1.23 |
| 6 | L006S | S | 118.01 | 1.18 |
| 6 | L006G | G | 116.94 | 1.17 |
| 6 | L006N | N | 115.98 | 1.16 |
| 6 | L006V | V | 115.39 | 1.15 |
| 6 | L006P | P | 115.11 | 1.15 |
| 6 | L006H | H | 114.99 | 1.15 |
| 6 | L006D | D | 114.30 | 1.14 |
| 6 | L006K | K | 111.33 | 1.11 |
| 6 | L006E | E | 109.38 | 1.09 |
| 6 | L006A | A | 109.11 | 1.09 |
| 6 | L006T | T | 105.11 | 1.05 |
| 6 | L006I | I | 105.10 | 1.05 |
| 6 | L006R | R | 103.58 | 1.04 |
| 6 | L006F | F | 101.84 | 1.02 |
| 6 | L006C | C | 101.69 | 1.02 |
| 6 | L006W | W | 77.03 | 0.77 |
| 6 | L006Y | Y | 7.99 | 0.08 |
| 7 | W007V | V | 125.70 | 1.26 |
| 7 | W007M | M | 121.99 | 1.22 |
| 7 | W007S | S | 121.49 | 1.21 |
| 7 | W007R | R | 121.42 | 1.21 |
| 7 | W007P | P | 113.12 | 1.13 |
| 7 | W007T | T | 112.42 | 1.12 |
| 7 | W007N | N | 111.62 | 1.12 |
| 7 | W007Q | Q | 110.40 | 1.10 |
| 7 | W007F | F | 109.54 | 1.10 |
| 7 | W007K | K | 99.28 | 0.99 |
| 7 | W007C | C | 99.28 | 0.99 |
| 7 | W007G | G | 98.93 | 0.99 |
| 7 | W007H | H | 95.65 | 0.96 |
| 7 | W007A | A | 92.24 | 0.92 |
| 7 | W007L | L | 80.60 | 0.81 |
| 7 | W007Y | Y | 61.72 | 0.62 |
| 7 | W007I | I | 6.21 | 0.06 |
| 8 | I008F | F | 114.74 | 1.15 |
| 8 | I008S | S | 111.06 | 1.11 |
| 8 | I008P | P | 107.32 | 1.07 |
| 8 | I008L | L | 106.57 | 1.07 |
| 8 | I008V | V | 105.39 | 1.05 |
| 8 | I008T | T | 105.22 | 1.05 |
| 8 | I008Y | Y | 103.53 | 1.04 |
| 8 | I008M | M | 100.20 | 1.00 |
| 8 | I008E | E | 99.53 | 1.00 |
| 8 | I008A | A | 95.64 | 0.96 |
| 8 | I008D | D | 75.18 | 0.75 |
| 8 | I008R | R | 4.60 | 0.05 |
| 9 | V009R | R | 130.14 | 1.30 |
| 9 | V009P | P | 122.65 | 1.23 |
| 9 | V009M | M | 114.91 | 1.15 |
| 9 | V009I | I | 114.34 | 1.14 |
| 9 | V009Y | Y | 111.23 | 1.11 |
| 9 | V009S | S | 107.52 | 1.08 |
| 9 | V009C | C | 105.80 | 1.06 |
| 9 | V009T | T | 105.04 | 1.05 |
| 9 | V009E | E | 100.29 | 1.00 |
| 9 | V009W | W | 98.90 | 0.99 |
| 9 | V009L | L | 97.67 | 0.98 |
| 9 | V009A | A | 93.84 | 0.94 |
| 9 | V009H | H | 86.35 | 0.86 |
| 9 | V009N | N | 85.33 | 0.85 |
| 9 | V009K | K | 6.32 | 0.06 |
| 10 | A010M | M | 127.85 | 1.28 |
| 10 | A010R | R | 106.71 | 1.07 |
| 10 | A010I | I | 106.36 | 1.06 |
| 10 | A010S | S | 106.34 | 1.06 |
| 10 | A010Q | Q | 106.33 | 1.06 |
| 10 | A010P | P | 105.05 | 1.05 |
| 10 | A010C | C | 104.29 | 1.04 |
| 10 | A010H | H | 103.11 | 1.03 |
| 10 | A010N | N | 101.39 | 1.01 |
| 10 | A010G | G | 100.93 | 1.01 |
| 10 | A010W | W | 97.00 | 0.97 |
| 10 | A010T | T | 96.44 | 0.96 |
| 10 | A010K | K | 59.66 | 0.60 |
| 10 | A010D | D | 45.09 | 0.45 |
| 10 | A010L | L | 30.80 | 0.31 |

TABLE 2-continued

| POSITION* | VARIANT CODE | VARIANT AMINO ACID | PROTEIN CON-CENTRATION | ACTIVITY RATIO# |
|---|---|---|---|---|
| 10 | A010F | F | 8.41 | 0.08 |
| 11 | S011G | G | 124.00 | 1.24 |
| 11 | S011M | M | 114.00 | 1.14 |
| 11 | S011P | P | 113.00 | 1.13 |
| 11 | S011C | C | 112.00 | 1.12 |
| 11 | S011F | F | 112.00 | 1.12 |
| 11 | S011V | V | 104.16 | 1.04 |
| 11 | S011N | N | 104.00 | 1.04 |
| 11 | S011A | A | 100.00 | 1.00 |
| 11 | S011Y | Y | 96.00 | 0.96 |
| 11 | S011D | D | 95.00 | 0.95 |
| 11 | S011T | T | 95.00 | 0.95 |
| 11 | S011L | L | 92.00 | 0.92 |
| 11 | S011Q | Q | 92.00 | 0.92 |
| 11 | S011I | I | 90.00 | 0.90 |
| 11 | S011W | W | 88.00 | 0.88 |
| 11 | S011K | K | 66.00 | 0.66 |
| 11 | S011R | R | 43.00 | 0.43 |
| 12 | T012A | A | 142.37 | 1.42 |
| 12 | T012G | G | 134.84 | 1.35 |
| 12 | T012H | H | 131.21 | 1.31 |
| 12 | T012C | C | 131.00 | 1.31 |
| 12 | T012W | W | 127.05 | 1.27 |
| 12 | T012S | S | 126.74 | 1.27 |
| 12 | T012V | V | 125.13 | 1.25 |
| 12 | T012M | M | 123.79 | 1.24 |
| 12 | T012P | P | 120.33 | 1.20 |
| 12 | T012I | I | 117.21 | 1.17 |
| 12 | T012Q | Q | 111.02 | 1.11 |
| 12 | T012F | F | 105.34 | 1.05 |
| 12 | T012N | N | 97.46 | 0.97 |
| 12 | T012E | E | 82.85 | 0.83 |
| 12 | T012K | K | 76.37 | 0.76 |
| 12 | T012R | R | 51.07 | 0.51 |
| 12 | T012D | D | 50.05 | 0.50 |
| 12 | T012L | L | 7.07 | 0.07 |
| 13 | A013G | G | 127.43 | 1.27 |
| 13 | A013V | V | 119.50 | 1.20 |
| 13 | A013S | S | 106.50 | 1.07 |
| 13 | A013Q | Q | 105.87 | 1.06 |
| 13 | A013F | F | 101.75 | 1.02 |
| 13 | A013C | C | 100.86 | 1.01 |
| 13 | A013T | T | 95.70 | 0.96 |
| 13 | A013M | M | 91.53 | 0.92 |
| 13 | A013N | N | 86.10 | 0.86 |
| 13 | A013W | W | 85.59 | 0.86 |
| 13 | A013E | E | 83.94 | 0.84 |
| 13 | A013P | P | 72.98 | 0.73 |
| 13 | A013D | D | 50.95 | 0.51 |
| 13 | A013R | R | 27.55 | 0.28 |
| 13 | A013H | H | 7.61 | 0.08 |
| 13 | A013L | L | 7.22 | 0.07 |
| 14 | L014S | S | 150.94 | 1.51 |
| 14 | L014V | V | 144.29 | 1.44 |
| 14 | L014A | A | 141.26 | 1.41 |
| 14 | L014F | F | 129.64 | 1.30 |
| 14 | L014W | W | 125.51 | 1.26 |
| 14 | L014M | M | 117.13 | 1.17 |
| 14 | L014G | G | 107.37 | 1.07 |
| 14 | L014I | I | 95.68 | 0.96 |
| 14 | L014H | H | 89.97 | 0.90 |
| 14 | L014N | N | 78.82 | 0.79 |
| 14 | L014Q | Q | 67.18 | 0.67 |
| 14 | L014Y | Y | 62.88 | 0.63 |
| 14 | L014K | K | 41.53 | 0.42 |
| 14 | L014E | E | 40.85 | 0.41 |
| 14 | L014R | R | 32.05 | 0.32 |
| 14 | L014P | P | 8.63 | 0.09 |
| 15 | L015G | G | 144.04 | 1.44 |
| 15 | L015T | T | 134.29 | 1.34 |
| 15 | L015M | M | 128.01 | 1.28 |
| 15 | L015C | C | 125.90 | 1.26 |
| 15 | L015V | V | 119.25 | 1.19 |
| 15 | L015Y | Y | 118.30 | 1.18 |
| 15 | L015W | W | 116.98 | 1.17 |
| 15 | L015A | A | 109.90 | 1.10 |
| 15 | L015F | F | 102.58 | 1.03 |
| 15 | L015S | S | 98.62 | 0.99 |
| 15 | L015P | P | 84.79 | 0.85 |
| 15 | L015Q | Q | 53.19 | 0.53 |
| 15 | L015K | K | 49.84 | 0.50 |
| 15 | L015N | N | 43.69 | 0.44 |
| 15 | L015H | H | 41.81 | 0.42 |
| 15 | L015E | E | 41.21 | 0.41 |
| 15 | L015R | R | 10.80 | 0.11 |
| 16 | I016W | W | 153.84 | 1.54 |
| 16 | I016S | S | 129.21 | 1.29 |
| 16 | I016G | G | 122.70 | 1.23 |
| 16 | I016A | A | 116.84 | 1.17 |
| 16 | I016C | C | 109.27 | 1.09 |
| 16 | I016V | V | 103.40 | 1.03 |
| 16 | I016Y | Y | 101.35 | 1.01 |
| 16 | I016T | T | 88.85 | 0.89 |
| 16 | I016H | H | 75.02 | 0.75 |
| 16 | I016N | N | 71.58 | 0.72 |
| 16 | I016F | F | 57.93 | 0.58 |
| 16 | I016E | E | 38.94 | 0.39 |
| 16 | I016P | P | 23.34 | 0.23 |
| 16 | I016R | R | 18.70 | 0.19 |
| 16 | I016L | L | 11.62 | 0.12 |
| 17 | S017M | M | 129.94 | 1.30 |
| 17 | S017A | A | 129.04 | 1.29 |
| 17 | S017R | R | 126.92 | 1.27 |
| 17 | S017L | L | 118.09 | 1.18 |
| 17 | S017H | H | 116.37 | 1.16 |
| 17 | S017K | K | 114.85 | 1.15 |
| 17 | S017V | V | 112.73 | 1.13 |
| 17 | S017D | D | 112.49 | 1.12 |
| 17 | S017C | C | 110.18 | 1.10 |
| 17 | S017G | G | 108.87 | 1.09 |
| 17 | S017E | E | 108.53 | 1.09 |
| 17 | S017Y | Y | 104.68 | 1.05 |
| 17 | S017I | I | 91.72 | 0.92 |
| 17 | S017T | T | 88.65 | 0.89 |
| 17 | S017F | F | 86.66 | 0.87 |
| 17 | S017P | P | 83.37 | 0.83 |
| 18 | V018M | M | 141.00 | 1.41 |
| 18 | V018T | T | 118.00 | 1.18 |
| 18 | V018A | A | 117.48 | 1.17 |
| 18 | V018W | W | 112.69 | 1.13 |
| 18 | V018E | E | 110.30 | 1.10 |
| 18 | V018S | S | 104.38 | 1.04 |
| 18 | V018R | R | 102.00 | 1.02 |
| 18 | V018C | C | 99.00 | 0.99 |
| 18 | V018D | D | 92.82 | 0.93 |
| 18 | V018F | F | 90.00 | 0.90 |
| 18 | V018 | 8 | 86.00 | 0.86 |
| 18 | V018P | P | 80.92 | 0.81 |
| 18 | V018H | H | 76.00 | 0.76 |
| 18 | V018L | L | 53.62 | 0.54 |
| 18 | V018I | I | 50.32 | 0.50 |
| 18 | V018G | G | 49.92 | 0.50 |
| 18 | V018Y | Y | 42.71 | 0.43 |
| 19 | A019E | E | 142.51 | 1.43 |
| 19 | A019M | M | 121.02 | 1.21 |
| 19 | A019C | C | 114.96 | 1.15 |
| 19 | A019S | S | 113.37 | 1.13 |
| 19 | A019L | L | 112.60 | 1.13 |
| 19 | A019W | W | 109.73 | 1.10 |
| 19 | A019V | V | 109.69 | 1.10 |
| 19 | A019G | G | 108.40 | 1.08 |
| 19 | A019T | T | 103.33 | 1.03 |
| 19 | A019I | I | 91.94 | 0.92 |
| 19 | A019K | K | 91.82 | 0.92 |
| 19 | A019F | F | 84.12 | 0.84 |
| 19 | A019R | R | 81.36 | 0.81 |
| 19 | A019P | P | 80.92 | 0.81 |
| 20 | F020N | N | 123.06 | 1.23 |
| 20 | F020Q | Q | 118.20 | 1.18 |
| 20 | F020M | M | 115.31 | 1.15 |
| 20 | F020V | V | 107.59 | 1.08 |
| 20 | F020S | S | 107.24 | 1.07 |

TABLE 2-continued

| POSITION* | VARIANT CODE | VARIANT AMINO ACID | PROTEIN CONCENTRATION | ACTIVITY RATIO# |
|---|---|---|---|---|
| 20 | F020T | T | 104.65 | 1.05 |
| 20 | F020L | L | 100.66 | 1.01 |
| 20 | F020G | G | 99.06 | 0.99 |
| 20 | F020D | D | 94.64 | 0.95 |
| 20 | F020I | I | 93.21 | 0.93 |
| 20 | F020E | E | 89.45 | 0.89 |
| 20 | F020K | K | 89.03 | 0.89 |
| 20 | F020R | R | 71.76 | 0.72 |
| 20 | F020A | A | 6.86 | 0.07 |
| 21 | S021T | T | 98.31 | 0.98 |
| 21 | S021E | E | 90.76 | 0.91 |
| 21 | S021Q | Q | 86.03 | 0.86 |
| 21 | S021M | M | 82.73 | 0.83 |
| 21 | S021G | G | 81.75 | 0.82 |
| 21 | S021A | A | 81.13 | 0.81 |
| 21 | S021W | W | 80.36 | 0.80 |
| 21 | S021V | V | 79.71 | 0.80 |
| 21 | S021R | R | 79.66 | 0.80 |
| 21 | S021K | K | 77.77 | 0.78 |
| 21 | S021L | L | 72.62 | 0.73 |
| 21 | S021N | N | 71.73 | 0.72 |
| 21 | S021I | I | 66.14 | 0.66 |
| 21 | S021C | C | 39.26 | 0.39 |
| 21 | S021Y | Y | 39.16 | 0.39 |
| 21 | S021P | P | 30.33 | 0.30 |
| 21 | S021F | F | 8.13 | 0.08 |
| 21 | S021H | H | 7.67 | 0.08 |
| 22 | S022M | M | 154.51 | 1.55 |
| 22 | S022V | V | 121.71 | 1.22 |
| 22 | S022D | D | 119.67 | 1.20 |
| 22 | S022W | W | 116.41 | 1.16 |
| 22 | S022G | G | 115.06 | 1.15 |
| 22 | S022T | T | 109.16 | 1.09 |
| 22 | S022R | R | 108.79 | 1.09 |
| 22 | S022P | P | 108.47 | 1.08 |
| 22 | S022Y | Y | 106.89 | 1.07 |
| 22 | S022A | A | 102.30 | 1.02 |
| 22 | S022L | L | 97.24 | 0.97 |
| 22 | S022F | F | 95.17 | 0.95 |
| 22 | S022E | E | 93.31 | 0.93 |
| 22 | S022H | H | 92.95 | 0.93 |
| 22 | S022C | C | 89.96 | 0.90 |
| 23 | S023K | K | 128.31 | 1.28 |
| 23 | S023G | G | 119.02 | 1.19 |
| 23 | S023E | E | 114.55 | 1.15 |
| 23 | S023H | H | 113.30 | 1.13 |
| 23 | S023R | R | 113.12 | 1.13 |
| 23 | S023T | T | 112.61 | 1.13 |
| 23 | S023A | A | 91.93 | 0.92 |
| 23 | S023M | M | 91.58 | 0.92 |
| 23 | S023P | P | 91.42 | 0.91 |
| 23 | S023V | V | 88.72 | 0.89 |
| 23 | S023C | C | 86.61 | 0.87 |
| 23 | S023Q | Q | 83.15 | 0.83 |
| 23 | S023L | L | 77.16 | 0.77 |
| 23 | S023I | I | 74.48 | 0.74 |
| 23 | S023W | W | 36.43 | 0.36 |
| 23 | S023D | D | 7.46 | 0.07 |
| 24 | I024T | T | 140.91 | 1.41 |
| 24 | I024V | V | 128.01 | 1.28 |
| 24 | I024N | N | 110.91 | 1.11 |
| 24 | I024R | R | 110.89 | 1.11 |
| 24 | I024L | L | 105.32 | 1.05 |
| 24 | I024H | H | 102.41 | 1.02 |
| 24 | I024P | P | 101.05 | 1.01 |
| 24 | I024S | S | 100.69 | 1.01 |
| 24 | I024C | C | 98.49 | 0.98 |
| 24 | I024A | A | 95.72 | 0.96 |
| 24 | I024W | W | 94.63 | 0.95 |
| 24 | I024K | K | 94.07 | 0.94 |
| 24 | I024M | M | 93.64 | 0.94 |
| 24 | I024Y | Y | 8.75 | 0.09 |
| 24 | I024E | E | 6.70 | 0.07 |
| 25 | A025V | V | 88.01 | 0.88 |
| 25 | A025T | T | 63.92 | 0.64 |
| 25 | A025G | G | 63.07 | 0.63 |
| 25 | A025S | S | 57.55 | 0.58 |
| 25 | A025I | I | 51.29 | 0.51 |
| 25 | A025L | L | 43.81 | 0.44 |
| 25 | A025E | E | 32.21 | 0.32 |
| 25 | A025M | M | 31.37 | 0.31 |
| 25 | A025P | P | 29.29 | 0.29 |
| 25 | A025K | K | 27.25 | 0.27 |
| 25 | A025N | N | 25.98 | 0.26 |
| 25 | A025H | H | 23.74 | 0.24 |
| 25 | A025D | D | 19.49 | 0.19 |
| 25 | A025F | F | 16.89 | 0.17 |
| 25 | A025W | W | 11.14 | 0.11 |
| 26 | S026Y | Y | 129.81 | 1.30 |
| 26 | S026L | L | 120.14 | 1.20 |
| 26 | S026A | A | 112.01 | 1.12 |
| 26 | S026R | R | 111.71 | 1.12 |
| 26 | S026T | T | 107.06 | 1.07 |
| 26 | S026N | N | 101.40 | 1.01 |
| 26 | S026K | K | 99.57 | 1.00 |
| 26 | S026M | M | 94.81 | 0.95 |
| 26 | S026D | D | 93.37 | 0.93 |
| 26 | S026G | G | 90.33 | 0.90 |
| 26 | S026W | W | 87.38 | 0.87 |
| 26 | S026V | V | 82.41 | 0.82 |
| 26 | S026H | H | 81.00 | 0.81 |
| 26 | S026I | I | 76.78 | 0.77 |
| 26 | S026P | P | 47.45 | 0.47 |
| 27 | A027G | G | 67.18 | 0.67 |
| 27 | A027S | S | 44.42 | 0.44 |
| 27 | A027K | K | 40.64 | 0.41 |
| 27 | A027C | C | 39.47 | 0.39 |
| 27 | A027P | P | 39.46 | 0.39 |
| 27 | A027R | R | 37.92 | 0.38 |
| 27 | A027H | H | 36.42 | 0.36 |
| 27 | A027E | E | 31.42 | 0.31 |
| 27 | A027F | F | 30.21 | 0.30 |
| 27 | A027T | T | 21.37 | 0.21 |
| 27 | A027V | V | 20.42 | 0.20 |
| 27 | A027W | W | 11.82 | 0.12 |
| 27 | A027Q | Q | 11.60 | 0.12 |
| 27 | A027L | L | 4.86 | 0.05 |
| 28 | A028Q | Q | 109.07 | 1.09 |
| 28 | A028T | T | 107.38 | 1.07 |
| 28 | A028S | S | 83.96 | 0.84 |
| 28 | A028R | R | 80.35 | 0.80 |
| 28 | A028M | M | 79.43 | 0.79 |
| 28 | A028E | E | 71.65 | 0.72 |
| 28 | A028G | G | 68.05 | 0.68 |
| 28 | A028D | D | 61.77 | 0.62 |
| 28 | A028N | N | 57.89 | 0.58 |
| 28 | A028L | L | 55.70 | 0.56 |
| 28 | A028V | V | 51.81 | 0.52 |
| 28 | A028F | F | 31.30 | 0.31 |
| 28 | A028P | P | 27.66 | 0.28 |
| 28 | A028W | W | 24.87 | 0.25 |
| 29 | E029T | T | 133.40 | 1.33 |
| 29 | E029Y | Y | 124.28 | 1.24 |
| 29 | E029V | V | 117.64 | 1.18 |
| 29 | E029Q | Q | 115.48 | 1.15 |
| 29 | E029K | K | 114.06 | 1.14 |
| 29 | E029M | M | 113.42 | 1.13 |
| 29 | E029P | P | 111.96 | 1.12 |
| 29 | E029N | N | 111.04 | 1.11 |
| 29 | E029S | S | 107.45 | 1.07 |
| 29 | E029G | G | 107.33 | 1.07 |
| 29 | E029A | A | 107.09 | 1.07 |
| 29 | E029C | C | 87.77 | 0.88 |
| 29 | E029L | L | 85.82 | 0.86 |
| 29 | E029I | I | 80.97 | 0.81 |
| 29 | E029H | H | 72.39 | 0.72 |
| 29 | E029W | W | 65.30 | 0.65 |
| 29 | E029F | F | 58.62 | 0.59 |
| 30 | E030Q | Q | 125.96 | 1.26 |
| 30 | E030K | K | 120.69 | 1.21 |
| 30 | E030M | M | 117.64 | 1.18 |
| 30 | E030A | A | 112.55 | 1.13 |

TABLE 2-continued

| POSITION* | VARIANT CODE | VARIANT AMINO ACID | PROTEIN CONCENTRATION | ACTIVITY RATIO# |
|---|---|---|---|---|
| 30 | E030G | G | 104.25 | 1.04 |
| 30 | E030R | R | 103.70 | 1.04 |
| 30 | E030S | S | 103.37 | 1.03 |
| 30 | E030H | H | 103.05 | 1.03 |
| 30 | E030N | N | 100.98 | 1.01 |
| 30 | E030T | T | 100.94 | 1.01 |
| 30 | E030V | V | 99.31 | 0.99 |
| 30 | E030L | L | 97.86 | 0.98 |
| 30 | E030F | F | 87.10 | 0.87 |
| 30 | E030C | C | 71.99 | 0.72 |
| 30 | E030W | W | 69.05 | 0.69 |
| 30 | E030P | P | 6.54 | 0.07 |
| 31 | A031R | R | 123.14 | 1.23 |
| 31 | A031G | G | 118.11 | 1.18 |
| 31 | A031S | S | 110.90 | 1.11 |
| 31 | A031K | K | 108.32 | 1.08 |
| 31 | A031P | P | 105.73 | 1.06 |
| 31 | A031T | T | 99.73 | 1.00 |
| 31 | A031M | M | 96.10 | 0.96 |
| 31 | A031V | V | 95.95 | 0.96 |
| 31 | A031L | L | 75.13 | 0.75 |
| 31 | A031N | N | 67.25 | 0.67 |
| 31 | A031W | W | 64.44 | 0.64 |
| 31 | A031H | H | 10.14 | 0.10 |
| 32 | K032C | C | 67.52 | 0.68 |
| 32 | K032H | H | 55.09 | 0.55 |
| 32 | K032T | T | 54.10 | 0.54 |
| 32 | K032W | W | 50.65 | 0.51 |
| 32 | K032N | N | 47.14 | 0.47 |
| 32 | K032L | L | 44.25 | 0.44 |
| 32 | K032R | R | 37.80 | 0.38 |
| 32 | K032F | F | 37.58 | 0.38 |
| 32 | K032V | V | 33.13 | 0.33 |
| 32 | K032S | S | 30.77 | 0.31 |
| 32 | K032P | P | 27.44 | 0.27 |
| 32 | K032I | I | 15.39 | 0.15 |
| 32 | K032G | G | 12.63 | 0.13 |
| 32 | K032Y | Y | 10.28 | 0.10 |
| 33 | E033R | R | 197.92 | 1.98 |
| 33 | E033Q | Q | 194.17 | 1.94 |
| 33 | E033G | G | 146.63 | 1.47 |
| 33 | E033H | H | 132.79 | 1.33 |
| 33 | E033N | N | 129.84 | 1.30 |
| 33 | E033S | S | 128.25 | 1.28 |
| 33 | E033D | D | 125.01 | 1.25 |
| 33 | E033I | I | 124.33 | 1.24 |
| 33 | E033K | K | 116.99 | 1.17 |
| 33 | E033M | M | 105.94 | 1.06 |
| 33 | E033L | L | 94.42 | 0.94 |
| 33 | E033T | T | 89.95 | 0.90 |
| 33 | E033Y | Y | 72.82 | 0.73 |
| 33 | E033F | F | 71.77 | 0.72 |
| 33 | E033P | P | 38.46 | 0.38 |
| 34 | K034R | R | 111.00 | 1.11 |
| 34 | K034H | H | 86.37 | 0.86 |
| 34 | K034Q | Q | 64.00 | 0.64 |
| 34 | K034N | N | 56.38 | 0.56 |
| 34 | K034P | P | 55.00 | 0.55 |
| 34 | K034T | T | 55.00 | 0.55 |
| 34 | K034M | M | 52.00 | 0.52 |
| 34 | K034C | C | 48.00 | 0.48 |
| 34 | K034V | V | 46.00 | 0.46 |
| 34 | K034L | L | 35.00 | 0.35 |
| 34 | K034G | G | 34.00 | 0.34 |
| 34 | K034D | D | 27.00 | 0.27 |
| 34 | K034F | F | 25.00 | 0.25 |
| 34 | K034Y | Y | 24.00 | 0.24 |
| 34 | K034S | S | 5.00 | 0.05 |
| 35 | Y035F | F | 92.05 | 0.92 |
| 35 | Y035W | W | 29.00 | 0.29 |
| 35 | Y035V | V | 23.00 | 0.23 |
| 35 | Y035L | L | 11.96 | 0.12 |
| 35 | Y035C | C | 11.74 | 0.12 |
| 35 | Y035A | A | 9.31 | 0.09 |
| 35 | Y035R | R | 8.51 | 0.09 |
| 35 | Y035K | K | 8.00 | 0.08 |
| 35 | Y035S | S | 7.60 | 0.08 |
| 35 | Y035Q | Q | 7.00 | 0.07 |
| 35 | Y035P | P | 6.25 | 0.06 |
| 35 | Y035D | D | 6.15 | 0.06 |
| 35 | Y035E | E | 6.10 | 0.06 |
| 35 | Y035N | N | 6.00 | 0.06 |
| 35 | Y035T | T | 6.00 | 0.06 |
| 35 | Y035G | G | 5.85 | 0.06 |
| 36 | L036M | M | 97.00 | 0.97 |
| 36 | L036G | G | 33.00 | 0.33 |
| 36 | L036T | T | 33.00 | 0.33 |
| 36 | L036Y | Y | 25.04 | 0.25 |
| 36 | L036C | C | 24.00 | 0.24 |
| 36 | L036N | N | 20.00 | 0.20 |
| 36 | L036F | F | 19.00 | 0.19 |
| 36 | L036V | V | 17.00 | 0.17 |
| 36 | L036W | W | 9.00 | 0.09 |
| 36 | L036R | R | 8.00 | 0.08 |
| 36 | L036A | A | 7.00 | 0.07 |
| 36 | L036S | S | 7.00 | 0.07 |
| 36 | L036Q | Q | 6.21 | 0.06 |
| 36 | L036H | H | 6.08 | 0.06 |
| 36 | L036P | P | 5.71 | 0.06 |
| 36 | L036D | D | 3.67 | 0.04 |
| 37 | I037V | V | 59.70 | 0.60 |
| 37 | I037H | H | 22.95 | 0.23 |
| 37 | I037C | C | 9.56 | 0.10 |
| 37 | I037S | S | 9.48 | 0.09 |
| 37 | I037N | N | 8.54 | 0.09 |
| 37 | I037A | A | 8.15 | 0.08 |
| 37 | I037F | F | 7.80 | 0.08 |
| 37 | I037P | P | 7.57 | 0.08 |
| 37 | I037L | L | 7.27 | 0.07 |
| 37 | I037Y | Y | 7.00 | 0.07 |
| 37 | I037T | T | 6.86 | 0.07 |
| 37 | I037G | G | 6.86 | 0.07 |
| 37 | I037W | W | 6.53 | 0.07 |
| 37 | I037D | D | 6.46 | 0.06 |
| 37 | I037Q | Q | 6.45 | 0.06 |
| 37 | I037R | R | 5.83 | 0.06 |
| 38 | G038A | A | 56.00 | 0.56 |
| 38 | G038H | H | 34.76 | 0.35 |
| 38 | G038I | I | 32.00 | 0.32 |
| 38 | G038S | S | 31.00 | 0.31 |
| 38 | G038V | V | 31.00 | 0.31 |
| 38 | G038T | T | 24.00 | 0.24 |
| 38 | G038M | M | 21.00 | 0.21 |
| 38 | G038L | L | 15.10 | 0.15 |
| 38 | G038N | N | 15.00 | 0.15 |
| 38 | G038R | R | 13.00 | 0.13 |
| 38 | G038K | K | 12.55 | 0.13 |
| 38 | G038C | C | 12.00 | 0.12 |
| 38 | G038P | P | 10.00 | 0.10 |
| 38 | G038W | W | 9.87 | 0.10 |
| 38 | G038D | D | 8.00 | 0.08 |
| 38 | G038E | E | 8.00 | 0.08 |
| 38 | G038Y | Y | 7.09 | 0.07 |
| 39 | F039L | L | 14.25 | 0.14 |
| 39 | F039M | M | 14.10 | 0.14 |
| 39 | F039W | W | 10.45 | 0.10 |
| 39 | F039Y | Y | 9.72 | 0.10 |
| 39 | F039S | S | 8.78 | 0.09 |
| 39 | F039R | R | 8.71 | 0.09 |
| 39 | F039P | P | 8.06 | 0.08 |
| 39 | F039D | D | 7.82 | 0.08 |
| 39 | F039E | E | 7.79 | 0.08 |
| 39 | F039V | V | 7.59 | 0.08 |
| 39 | F039C | C | 7.51 | 0.08 |
| 39 | F039A | A | 6.77 | 0.07 |
| 39 | F039K | K | 6.00 | 0.06 |
| 39 | F039H | H | 5.90 | 0.06 |
| 39 | F039G | G | 5.87 | 0.06 |
| 39 | F039N | N | 5.76 | 0.06 |
| 39 | F039Q | Q | 5.54 | 0.06 |
| 39 | F039T | T | 5.39 | 0.05 |
| 40 | N040V | V | 126.00 | 1.26 |

TABLE 2-continued

| POSITION* | VARIANT CODE | VARIANT AMINO ACID | PROTEIN CONCENTRATION | ACTIVITY RATIO# |
|---|---|---|---|---|
| 40 | N040K | K | 118.87 | 1.19 |
| 40 | N040E | E | 110.47 | 1.10 |
| 40 | N040Q | Q | 109.00 | 1.09 |
| 40 | N040H | H | 107.23 | 1.07 |
| 40 | N040Y | Y | 106.81 | 1.07 |
| 40 | N040T | T | 106.00 | 1.06 |
| 40 | N040A | A | 104.00 | 1.04 |
| 40 | N040L | L | 104.00 | 1.04 |
| 40 | N040W | W | 102.81 | 1.03 |
| 40 | N040F | F | 102.53 | 1.03 |
| 40 | N040R | R | 102.00 | 1.02 |
| 40 | N040C | C | 98.00 | 0.98 |
| 40 | N040P | P | 98.00 | 0.98 |
| 40 | N040I | I | 88.00 | 0.88 |
| 40 | N040G | G | 82.00 | 0.82 |
| 40 | N040D | D | 72.46 | 0.72 |
| 40 | N040M | M | 70.39 | 0.70 |
| 40 | N040S | S | 19.00 | 0.19 |
| 41 | E041A | A | 142.97 | 1.43 |
| 41 | E041S | S | 125.74 | 1.26 |
| 41 | E041N | N | 113.99 | 1.14 |
| 41 | E041T | T | 113.64 | 1.14 |
| 41 | E041H | H | 108.25 | 1.08 |
| 41 | E041R | R | 104.86 | 1.05 |
| 41 | E041G | G | 97.74 | 0.98 |
| 41 | E041Y | Y | 95.99 | 0.96 |
| 41 | E041Q | Q | 92.70 | 0.93 |
| 41 | E041F | F | 63.24 | 0.63 |
| 41 | E041L | L | 60.52 | 0.61 |
| 41 | E041I | I | 52.81 | 0.53 |
| 41 | E041V | V | 45.47 | 0.45 |
| 41 | E041W | W | 32.22 | 0.32 |
| 41 | E041P | P | 9.27 | 0.09 |
| 42 | Q042M | M | 148.09 | 1.48 |
| 42 | Q042R | R | 130.84 | 1.31 |
| 42 | Q042P | P | 121.40 | 1.21 |
| 42 | Q042W | W | 113.30 | 1.13 |
| 42 | Q042S | S | 95.75 | 0.96 |
| 42 | Q042Y | Y | 86.74 | 0.87 |
| 42 | Q042K | K | 83.66 | 0.84 |
| 42 | Q042F | F | 75.21 | 0.75 |
| 42 | Q042H | H | 74.84 | 0.75 |
| 42 | Q042L | L | 73.83 | 0.74 |
| 42 | Q042A | A | 73.23 | 0.73 |
| 42 | Q042I | I | 67.65 | 0.68 |
| 42 | Q042E | E | 58.12 | 0.58 |
| 42 | Q042D | D | 57.23 | 0.57 |
| 42 | Q042T | T | 57.19 | 0.57 |
| 42 | Q042V | V | 42.92 | 0.43 |
| 42 | Q042C | C | 42.91 | 0.43 |
| 42 | Q042N | N | 27.71 | 0.28 |
| 43 | E043S | S | 163.96 | 1.64 |
| 43 | E043R | R | 124.40 | 1.24 |
| 43 | E043D | D | 120.22 | 1.20 |
| 43 | E043H | H | 105.43 | 1.05 |
| 43 | E043A | A | 104.90 | 1.05 |
| 43 | E043L | L | 95.08 | 0.95 |
| 43 | E043N | N | 91.28 | 0.91 |
| 43 | E043G | G | 90.19 | 0.90 |
| 43 | E043F | F | 69.79 | 0.70 |
| 43 | E043Y | Y | 66.91 | 0.67 |
| 43 | E043C | C | 66.68 | 0.67 |
| 43 | E043W | W | 64.35 | 0.64 |
| 43 | E043V | V | 53.37 | 0.53 |
| 43 | E043P | P | 42.96 | 0.43 |
| 43 | E043M | M | 8.82 | 0.09 |
| 43 | E043T | T | 5.27 | 0.05 |
| 44 | A044D | D | 136.49 | 1.36 |
| 44 | A044Q | Q | 113.72 | 1.14 |
| 44 | A044E | E | 108.45 | 1.08 |
| 44 | A044S | S | 102.67 | 1.03 |
| 44 | A044N | N | 90.51 | 0.91 |
| 44 | A044R | R | 82.63 | 0.83 |
| 44 | A044G | G | 82.29 | 0.82 |
| 44 | A044C | C | 80.18 | 0.80 |
| 44 | A044L | L | 79.49 | 0.79 |
| 44 | A044H | H | 69.28 | 0.69 |
| 44 | A044V | V | 50.75 | 0.51 |
| 44 | A044Y | Y | 44.57 | 0.45 |
| 44 | A044T | T | 42.35 | 0.42 |
| 44 | A044I | I | 29.22 | 0.29 |
| 44 | A044P | P | 16.75 | 0.17 |
| 44 | A044F | F | 8.08 | 0.08 |
| 45 | V045L | L | 128.46 | 1.28 |
| 45 | V045A | A | 122.17 | 1.22 |
| 45 | V045C | C | 117.75 | 1.18 |
| 45 | V045R | R | 89.35 | 0.89 |
| 45 | V045T | T | 83.00 | 0.83 |
| 45 | V045I | I | 81.29 | 0.81 |
| 45 | V045Q | Q | 69.47 | 0.69 |
| 45 | V045F | F | 42.91 | 0.43 |
| 45 | V045Y | Y | 38.60 | 0.39 |
| 45 | V045S | S | 31.46 | 0.31 |
| 45 | V045D | D | 30.61 | 0.31 |
| 45 | V045H | H | 15.52 | 0.16 |
| 45 | V045P | P | 13.16 | 0.13 |
| 45 | V045N | N | 8.45 | 0.08 |
| 46 | S046H | H | 180.17 | 1.80 |
| 46 | S046R | R | 163.56 | 1.64 |
| 46 | S046T | T | 145.04 | 1.45 |
| 46 | S046A | A | 134.77 | 1.35 |
| 46 | S046Q | Q | 133.68 | 1.34 |
| 46 | S046Y | Y | 126.03 | 1.26 |
| 46 | S046W | W | 108.60 | 1.09 |
| 46 | S046V | V | 99.68 | 1.00 |
| 46 | S046L | L | 95.29 | 0.95 |
| 46 | S046G | G | 94.57 | 0.95 |
| 46 | S046D | D | 94.34 | 0.94 |
| 46 | S046E | E | 80.44 | 0.80 |
| 46 | S046F | F | 68.99 | 0.69 |
| 46 | S046P | P | 46.63 | 0.47 |
| 47 | E047D | D | 161.68 | 1.62 |
| 47 | E047R | R | 127.01 | 1.27 |
| 47 | E047K | K | 105.12 | 1.05 |
| 47 | E047Q | Q | 103.73 | 1.04 |
| 47 | E047H | H | 102.20 | 1.02 |
| 47 | E047A | A | 99.30 | 0.99 |
| 47 | E047Y | Y | 93.27 | 0.93 |
| 47 | E047N | N | 88.69 | 0.89 |
| 47 | E047S | S | 82.06 | 0.82 |
| 47 | E047T | T | 81.19 | 0.81 |
| 47 | E047V | V | 78.37 | 0.78 |
| 47 | E047L | L | 68.89 | 0.69 |
| 47 | E047G | G | 55.86 | 0.56 |
| 47 | E047F | F | 50.48 | 0.50 |
| 47 | E047C | C | 49.85 | 0.50 |
| 47 | E047W | W | 41.91 | 0.42 |
| 47 | E047P | P | 22.22 | 0.22 |
| 48 | F048W | W | 100.77 | 1.01 |
| 48 | F048M | M | 20.43 | 0.20 |
| 48 | F048L | L | 16.60 | 0.17 |
| 48 | F048I | I | 11.37 | 0.11 |
| 48 | F048V | V | 10.65 | 0.11 |
| 48 | F048R | R | 9.36 | 0.09 |
| 48 | F048C | C | 9.30 | 0.09 |
| 48 | F048P | P | 8.69 | 0.09 |
| 48 | F048S | S | 8.60 | 0.09 |
| 48 | F048K | K | 8.47 | 0.08 |
| 48 | F048H | H | 8.40 | 0.08 |
| 48 | F048N | N | 8.39 | 0.08 |
| 48 | F048E | E | 8.29 | 0.08 |
| 48 | F048D | D | 7.97 | 0.08 |
| 48 | F048G | G | 7.50 | 0.07 |
| 49 | V049G | G | 135.00 | 1.35 |
| 49 | V049C | C | 95.00 | 0.95 |
| 49 | V049R | R | 87.00 | 0.87 |
| 49 | V049K | K | 58.91 | 0.59 |
| 49 | V049M | M | 58.41 | 0.58 |
| 49 | V049A | A | 54.56 | 0.55 |
| 49 | V049W | W | 46.00 | 0.46 |
| 49 | V049T | T | 38.00 | 0.38 |
| 49 | V049S | S | 25.00 | 0.25 |

TABLE 2-continued

| POSITION* | VARIANT CODE | VARIANT AMINO ACID | PROTEIN CONCENTRATION | ACTIVITY RATIO# |
|---|---|---|---|---|
| 49 | V049Y | Y | 20.00 | 0.20 |
| 49 | V049Q | Q | 17.26 | 0.17 |
| 49 | V049P | P | 15.00 | 0.15 |
| 49 | V049L | L | 14.00 | 0.14 |
| 49 | V049F | F | 13.93 | 0.14 |
| 49 | V049E | E | 10.00 | 0.10 |
| 49 | V049N | N | 9.00 | 0.09 |
| 49 | V049D | D | 8.00 | 0.08 |
| 49 | V049H | H | 8.00 | 0.08 |
| 49 | V049I | I | 8.00 | 0.08 |
| 50 | E050H | H | 112.00 | 1.12 |
| 50 | E050A | A | 96.00 | 0.96 |
| 50 | E050S | S | 83.00 | 0.83 |
| 50 | E050D | D | 82.58 | 0.83 |
| 50 | E050Q | Q | 77.00 | 0.77 |
| 50 | E050R | R | 77.00 | 0.77 |
| 50 | E050K | K | 73.00 | 0.73 |
| 50 | E050M | M | 71.98 | 0.72 |
| 50 | E050T | T | 64.00 | 0.64 |
| 50 | E050G | G | 61.95 | 0.62 |
| 50 | E050Y | Y | 52.00 | 0.52 |
| 50 | E050L | L | 49.00 | 0.49 |
| 50 | E050F | F | 47.00 | 0.47 |
| 50 | E050I | I | 46.83 | 0.47 |
| 50 | E050W | W | 42.01 | 0.42 |
| 50 | E050N | N | 32.42 | 0.32 |
| 50 | E050V | V | 29.83 | 0.30 |
| 50 | E050P | P | 6.00 | 0.06 |
| 51 | Q051M | M | 119.81 | 1.20 |
| 51 | Q051R | R | 108.69 | 1.09 |
| 51 | Q051K | K | 97.54 | 0.98 |
| 51 | Q051A | A | 84.10 | 0.84 |
| 51 | Q051T | T | 83.15 | 0.83 |
| 51 | Q051E | E | 75.80 | 0.76 |
| 51 | Q051N | N | 75.33 | 0.75 |
| 51 | Q051H | H | 69.22 | 0.69 |
| 51 | Q051S | S | 68.17 | 0.68 |
| 51 | Q051G | G | 66.07 | 0.66 |
| 51 | Q051L | L | 65.45 | 0.65 |
| 51 | Q051D | D | 52.77 | 0.53 |
| 51 | Q051I | I | 45.84 | 0.46 |
| 51 | Q051F | F | 44.57 | 0.45 |
| 51 | Q051C | C | 43.93 | 0.44 |
| 51 | Q051V | V | 43.56 | 0.44 |
| 51 | Q051P | P | 5.94 | 0.06 |
| 52 | V052L | L | 108.19 | 1.08 |
| 52 | V052W | W | 104.92 | 1.05 |
| 52 | V052M | M | 88.46 | 0.88 |
| 52 | V052I | I | 79.27 | 0.79 |
| 52 | V052A | A | 72.78 | 0.73 |
| 52 | V052H | H | 52.94 | 0.53 |
| 52 | V052F | F | 52.32 | 0.52 |
| 52 | V052C | C | 46.72 | 0.47 |
| 52 | V052T | T | 39.52 | 0.40 |
| 52 | V052G | G | 39.28 | 0.39 |
| 52 | V052Q | Q | 34.36 | 0.34 |
| 52 | V052R | R | 18.76 | 0.19 |
| 52 | V052N | N | 15.55 | 0.16 |
| 52 | V052S | S | 15.02 | 0.15 |
| 52 | V052E | E | 7.54 | 0.08 |
| 52 | V052P | P | 6.39 | 0.06 |
| 52 | V052D | D | 5.86 | 0.06 |
| 53 | E053A | A | 140.37 | 1.40 |
| 53 | E053K | K | 127.20 | 1.27 |
| 53 | E053R | R | 119.65 | 1.20 |
| 53 | E053H | H | 109.57 | 1.10 |
| 53 | E053N | N | 98.87 | 0.99 |
| 53 | E053L | L | 98.50 | 0.98 |
| 53 | E053P | P | 97.72 | 0.98 |
| 53 | E053V | V | 94.43 | 0.94 |
| 53 | E053F | F | 94.05 | 0.94 |
| 53 | E053S | S | 89.81 | 0.90 |
| 53 | E053Y | Y | 86.04 | 0.86 |
| 53 | E053T | T | 83.88 | 0.84 |
| 53 | E053C | C | 81.12 | 0.81 |
| 53 | E053W | W | 77.76 | 0.78 |
| 53 | E053D | D | 68.39 | 0.68 |
| 53 | E053G | G | 67.56 | 0.68 |
| 53 | E053Q | Q | 13.97 | 0.14 |
| 54 | A054L | L | 137.74 | 1.38 |
| 54 | A054S | S | 136.79 | 1.37 |
| 54 | A054R | R | 97.90 | 0.98 |
| 54 | A054D | D | 97.17 | 0.97 |
| 54 | A054G | G | 90.30 | 0.90 |
| 54 | A054T | T | 88.68 | 0.89 |
| 54 | A054C | C | 83.34 | 0.83 |
| 54 | A054N | N | 83.10 | 0.83 |
| 54 | A054I | I | 81.67 | 0.82 |
| 54 | A054K | K | 81.00 | 0.81 |
| 54 | A054H | H | 77.17 | 0.77 |
| 54 | A054Y | Y | 74.93 | 0.75 |
| 54 | A054F | F | 60.70 | 0.61 |
| 54 | A054V | V | 60.08 | 0.60 |
| 54 | A054P | P | 23.50 | 0.24 |
| 55 | N055H | H | 85.10 | 0.85 |
| 55 | N055A | A | 72.93 | 0.73 |
| 55 | N055M | M | 69.99 | 0.70 |
| 55 | N055Q | Q | 63.43 | 0.63 |
| 55 | N055E | E | 59.81 | 0.60 |
| 55 | N055R | R | 53.48 | 0.53 |
| 55 | N055G | G | 46.03 | 0.46 |
| 55 | N055K | K | 45.82 | 0.46 |
| 55 | N055S | S | 41.16 | 0.41 |
| 55 | N055Y | Y | 38.86 | 0.39 |
| 55 | N055I | I | 35.72 | 0.36 |
| 55 | N055V | V | 29.77 | 0.30 |
| 55 | N055F | F | 28.77 | 0.29 |
| 55 | N055L | L | 26.96 | 0.27 |
| 55 | N055P | P | 22.56 | 0.23 |
| 56 | D056G | G | 124.69 | 1.25 |
| 56 | D056S | S | 116.41 | 1.16 |
| 56 | D056K | K | 112.18 | 1.12 |
| 56 | D056R | R | 101.95 | 1.02 |
| 56 | D056N | N | 100.33 | 1.00 |
| 56 | D056H | H | 98.12 | 0.98 |
| 56 | D056A | A | 86.03 | 0.86 |
| 56 | D056T | T | 68.54 | 0.69 |
| 56 | D056Y | Y | 56.65 | 0.57 |
| 56 | D056F | F | 49.98 | 0.50 |
| 56 | D056P | P | 47.08 | 0.47 |
| 56 | D056V | V | 46.58 | 0.47 |
| 56 | D056L | L | 38.46 | 0.38 |
| 56 | D056I | I | 31.73 | 0.32 |
| 56 | D056W | W | 30.14 | 0.30 |
| 57 | E057N | N | 252.24 | 2.52 |
| 57 | E057H | H | 157.45 | 1.57 |
| 57 | E057S | S | 145.56 | 1.46 |
| 57 | E057G | G | 145.37 | 1.45 |
| 57 | E057Q | Q | 143.17 | 1.43 |
| 57 | E057C | C | 139.04 | 1.39 |
| 57 | E057M | M | 128.97 | 1.29 |
| 57 | E057D | D | 128.47 | 1.28 |
| 57 | E057R | R | 120.64 | 1.21 |
| 57 | E057K | K | 118.25 | 1.18 |
| 57 | E057W | W | 116.28 | 1.16 |
| 57 | E057F | F | 107.79 | 1.08 |
| 57 | E057V | V | 100.08 | 1.00 |
| 57 | E057L | L | 99.38 | 0.99 |
| 57 | E057P | P | 65.08 | 0.65 |
| 57 | E057I | I | 61.84 | 0.62 |
| 57 | E057T | T | 26.62 | 0.27 |
| 58 | V058R | R | 129.15 | 1.29 |
| 58 | V058Y | Y | 123.00 | 1.23 |
| 58 | V058H | H | 123.00 | 1.23 |
| 58 | V058M | M | 112.92 | 1.13 |
| 58 | V058K | K | 110.16 | 1.10 |
| 58 | V058C | C | 109.43 | 1.09 |
| 58 | V058L | L | 106.58 | 1.07 |
| 58 | V058A | A | 104.97 | 1.05 |
| 58 | V058F | F | 102.77 | 1.03 |
| 58 | V058N | N | 95.69 | 0.96 |
| 58 | V058S | S | 93.83 | 0.94 |

TABLE 2-continued

| POSITION* | VARIANT CODE | VARIANT AMINO ACID | PROTEIN CON-CENTRATION | ACTIVITY RATIO# |
|---|---|---|---|---|
| 58 | V058I | I | 93.50 | 0.94 |
| 58 | V058T | T | 91.46 | 0.91 |
| 58 | V058G | G | 87.22 | 0.87 |
| 58 | V058D | D | 74.09 | 0.74 |
| 58 | V058E | E | 67.17 | 0.67 |
| 58 | V058P | P | 61.56 | 0.62 |
| 58 | V058Q | Q | 6.39 | 0.06 |
| 59 | A059R | R | 187.27 | 1.87 |
| 59 | A059Y | Y | 172.73 | 1.73 |
| 59 | A059V | V | 159.93 | 1.60 |
| 59 | A059I | I | 136.28 | 1.36 |
| 59 | A059F | F | 135.64 | 1.36 |
| 59 | A059W | W | 125.18 | 1.25 |
| 59 | A059M | M | 123.19 | 1.23 |
| 59 | A059L | L | 121.10 | 1.21 |
| 59 | A059H | H | 110.74 | 1.11 |
| 59 | A059S | S | 91.95 | 0.92 |
| 59 | A059T | T | 87.06 | 0.87 |
| 59 | A059Q | Q | 73.05 | 0.73 |
| 59 | A059G | G | 71.74 | 0.72 |
| 59 | A059D | D | 69.29 | 0.69 |
| 59 | A059N | N | 66.70 | 0.67 |
| 59 | A059E | E | 64.01 | 0.64 |
| 59 | A059P | P | 59.36 | 0.59 |
| 59 | A059K | K | 33.09 | 0.33 |
| 60 | I060L | L | 103.80 | 1.04 |
| 60 | I060V | V | 97.35 | 0.97 |
| 60 | I060R | R | 96.55 | 0.97 |
| 60 | I060M | M | 90.48 | 0.90 |
| 60 | I060K | K | 75.87 | 0.76 |
| 60 | I060Y | Y | 73.84 | 0.74 |
| 60 | I060Q | Q | 72.24 | 0.72 |
| 60 | I060N | N | 67.92 | 0.68 |
| 60 | I060E | E | 65.70 | 0.66 |
| 60 | I060D | D | 65.27 | 0.65 |
| 60 | I060A | A | 61.85 | 0.62 |
| 60 | I060G | G | 61.08 | 0.61 |
| 60 | I060S | S | 51.51 | 0.52 |
| 60 | I060T | T | 46.40 | 0.46 |
| 60 | I060H | H | 36.92 | 0.37 |
| 60 | I060P | P | 19.01 | 0.19 |
| 60 | I060W | W | 5.42 | 0.05 |
| 61 | L061M | M | 129.95 | 1.30 |
| 61 | L061T | T | 124.71 | 1.25 |
| 61 | L061A | A | 123.36 | 1.23 |
| 61 | L061I | I | 110.37 | 1.10 |
| 61 | L061V | V | 108.74 | 1.09 |
| 61 | L061G | G | 108.57 | 1.09 |
| 61 | L061P | P | 102.67 | 1.03 |
| 61 | L061D | D | 102.28 | 1.02 |
| 61 | L061S | S | 97.83 | 0.98 |
| 61 | L061K | K | 95.81 | 0.96 |
| 61 | L061Q | Q | 95.57 | 0.96 |
| 61 | L061E | E | 91.81 | 0.92 |
| 61 | L061R | R | 85.77 | 0.86 |
| 61 | L061H | H | 66.88 | 0.67 |
| 61 | L061N | N | 35.28 | 0.35 |
| 62 | S062V | V | 161.32 | 1.61 |
| 62 | S062W | W | 157.12 | 1.57 |
| 62 | S062M | M | 150.12 | 1.50 |
| 62 | S062P | P | 139.57 | 1.40 |
| 62 | S062N | N | 134.16 | 1.34 |
| 62 | S062H | H | 133.29 | 1.33 |
| 62 | S062Q | Q | 124.88 | 1.25 |
| 62 | S062D | D | 120.10 | 1.20 |
| 62 | S062G | G | 118.35 | 1.18 |
| 62 | S062I | I | 116.17 | 1.16 |
| 62 | S062A | A | 115.62 | 1.16 |
| 62 | S062L | L | 107.95 | 1.08 |
| 62 | S062C | C | 107.34 | 1.07 |
| 62 | S062R | R | 107.31 | 1.07 |
| 62 | S062T | T | 105.80 | 1.06 |
| 62 | S062K | K | 96.88 | 0.97 |
| 62 | S062F | F | 77.46 | 0.77 |
| 63 | E063A | A | 151.93 | 1.52 |
| 63 | E063G | G | 151.54 | 1.52 |
| 63 | E063D | D | 143.23 | 1.43 |
| 63 | E063R | R | 138.35 | 1.38 |
| 63 | E063T | T | 133.00 | 1.33 |
| 63 | E063Q | Q | 126.78 | 1.27 |
| 63 | E063C | C | 122.66 | 1.23 |
| 63 | E063K | K | 114.56 | 1.15 |
| 63 | E063H | H | 107.55 | 1.08 |
| 63 | E063I | I | 103.97 | 1.04 |
| 63 | E063S | S | 101.87 | 1.02 |
| 63 | E063Y | Y | 96.83 | 0.97 |
| 63 | E063L | L | 94.72 | 0.95 |
| 63 | E063W | W | 72.62 | 0.73 |
| 63 | E063V | V | 68.49 | 0.68 |
| 63 | E063F | F | 54.52 | 0.55 |
| 64 | E064T | T | 118.91 | 1.19 |
| 64 | E064R | R | 110.53 | 1.11 |
| 64 | E064S | S | 109.23 | 1.09 |
| 64 | E064A | A | 102.92 | 1.03 |
| 64 | E064H | H | 93.59 | 0.94 |
| 64 | E064Q | Q | 91.03 | 0.91 |
| 64 | E064C | C | 90.99 | 0.91 |
| 64 | E064Y | Y | 88.33 | 0.88 |
| 64 | E064G | G | 79.36 | 0.79 |
| 64 | E064F | F | 67.32 | 0.67 |
| 64 | E064V | V | 66.57 | 0.67 |
| 64 | E064L | L | 62.47 | 0.62 |
| 64 | E064W | W | 60.29 | 0.60 |
| 64 | E064P | P | 44.81 | 0.45 |
| 64 | E064K | K | 6.18 | 0.06 |
| 64 | E064I | I | 5.10 | 0.05 |
| 65 | E065M | M | 123.46 | 1.23 |
| 65 | E065R | R | 116.00 | 1.16 |
| 65 | E065Q | Q | 109.80 | 1.10 |
| 65 | E065A | A | 107.63 | 1.08 |
| 65 | E065V | V | 104.79 | 1.05 |
| 65 | E065Y | Y | 104.29 | 1.04 |
| 65 | E065K | K | 100.28 | 1.00 |
| 65 | E065C | C | 94.55 | 0.95 |
| 65 | E065S | S | 93.73 | 0.94 |
| 65 | E065T | T | 89.80 | 0.90 |
| 65 | E065L | L | 89.07 | 0.89 |
| 65 | E065I | I | 87.89 | 0.88 |
| 65 | E065G | G | 80.18 | 0.80 |
| 65 | E065D | D | 71.30 | 0.71 |
| 65 | E065W | W | 70.97 | 0.71 |
| 65 | E065P | P | 56.54 | 0.57 |
| 66 | E066S | S | 135.22 | 1.35 |
| 66 | E066A | A | 128.91 | 1.29 |
| 66 | E066T | T | 127.73 | 1.28 |
| 66 | E066P | P | 123.84 | 1.24 |
| 66 | E066R | R | 121.88 | 1.22 |
| 66 | E066Y | Y | 115.52 | 1.16 |
| 66 | E066K | K | 108.25 | 1.08 |
| 66 | E066G | G | 105.02 | 1.05 |
| 66 | E066V | V | 104.05 | 1.04 |
| 66 | E066M | M | 103.51 | 1.04 |
| 66 | E066Q | Q | 100.84 | 1.01 |
| 66 | E066W | W | 99.26 | 0.99 |
| 66 | E066L | L | 93.75 | 0.94 |
| 66 | E066F | F | 91.41 | 0.91 |
| 66 | E066N | N | 87.34 | 0.87 |
| 66 | E066D | D | 71.95 | 0.72 |
| 66 | E066H | H | 36.85 | 0.37 |
| 67 | V067I | I | 113.21 | 1.13 |
| 67 | V067M | M | 73.82 | 0.74 |
| 67 | V067L | L | 72.32 | 0.72 |
| 67 | V067Y | Y | 70.71 | 0.71 |
| 67 | V067F | F | 58.59 | 0.59 |
| 67 | V067C | C | 56.98 | 0.57 |
| 67 | V067R | R | 55.35 | 0.55 |
| 67 | V067A | A | 54.90 | 0.55 |
| 67 | V067T | T | 41.46 | 0.41 |
| 67 | V067P | P | 34.73 | 0.35 |
| 67 | V067S | S | 28.45 | 0.28 |
| 67 | V067E | E | 20.66 | 0.21 |
| 67 | V067K | K | 20.54 | 0.21 |

TABLE 2-continued

| POSITION* | VARIANT CODE | VARIANT AMINO ACID | PROTEIN CON-CENTRATION | ACTIVITY RATIO# |
|---|---|---|---|---|
| 67 | V067N | N | 17.25 | 0.17 |
| 67 | V067G | G | 15.25 | 0.15 |
| 67 | V067D | D | 13.59 | 0.14 |
| 67 | V067H | H | 6.18 | 0.06 |
| 68 | E068K | K | 102.16 | 1.02 |
| 68 | E068Q | Q | 101.87 | 1.02 |
| 68 | E068S | S | 85.61 | 0.86 |
| 68 | E068D | D | 83.72 | 0.84 |
| 68 | E068R | R | 80.31 | 0.80 |
| 68 | E068N | N | 80.22 | 0.80 |
| 68 | E068P | P | 74.49 | 0.74 |
| 68 | E068T | T | 71.78 | 0.72 |
| 68 | E068G | G | 68.18 | 0.68 |
| 68 | E068A | A | 68.12 | 0.68 |
| 68 | E068C | C | 67.44 | 0.67 |
| 68 | E068Y | Y | 58.18 | 0.58 |
| 68 | E068M | M | 48.30 | 0.48 |
| 68 | E068V | V | 46.31 | 0.46 |
| 68 | E068I | I | 25.39 | 0.25 |
| 68 | E068L | L | 20.98 | 0.21 |
| 69 | I069V | V | 123.93 | 1.24 |
| 69 | I069L | L | 79.94 | 0.80 |
| 69 | I069N | N | 42.27 | 0.42 |
| 69 | I069S | S | 27.06 | 0.27 |
| 69 | I069F | F | 22.49 | 0.22 |
| 69 | I069A | A | 19.56 | 0.20 |
| 69 | I069T | T | 10.74 | 0.11 |
| 69 | I069Y | Y | 9.65 | 0.10 |
| 69 | I069W | W | 9.01 | 0.09 |
| 69 | I069P | P | 7.84 | 0.08 |
| 69 | I069R | R | 7.15 | 0.07 |
| 69 | I069Q | Q | 7.13 | 0.07 |
| 69 | I069G | G | 6.86 | 0.07 |
| 69 | I069D | D | 6.38 | 0.06 |
| 70 | E070T | T | 135.22 | 1.35 |
| 70 | E070R | R | 127.41 | 1.27 |
| 70 | E070N | N | 119.02 | 1.19 |
| 70 | E070S | S | 118.79 | 1.19 |
| 70 | E070V | V | 102.83 | 1.03 |
| 70 | E070G | G | 92.33 | 0.92 |
| 70 | E070D | D | 89.84 | 0.90 |
| 70 | E070C | C | 87.77 | 0.88 |
| 70 | E070A | A | 80.65 | 0.81 |
| 70 | E070I | I | 77.03 | 0.77 |
| 70 | E070Y | Y | 73.97 | 0.74 |
| 70 | E070L | L | 73.91 | 0.74 |
| 70 | E070P | P | 64.34 | 0.64 |
| 70 | E070F | F | 60.29 | 0.60 |
| 70 | E070W | W | 43.57 | 0.44 |
| 70 | E070K | K | 6.39 | 0.06 |
| 71 | L071V | V | 127.43 | 1.27 |
| 71 | L071I | I | 122.69 | 1.23 |
| 71 | L071D | D | 77.31 | 0.77 |
| 71 | L071M | M | 31.70 | 0.32 |
| 71 | L071T | T | 25.45 | 0.25 |
| 71 | L071P | P | 24.11 | 0.24 |
| 71 | L071R | R | 15.22 | 0.15 |
| 71 | L071K | K | 14.69 | 0.15 |
| 71 | L071S | S | 13.41 | 0.13 |
| 71 | L071W | W | 11.88 | 0.12 |
| 71 | L071Q | Q | 10.19 | 0.10 |
| 71 | L071E | E | 9.80 | 0.10 |
| 71 | L071C | C | 9.52 | 0.10 |
| 71 | L071G | G | 9.32 | 0.09 |
| 71 | L071H | H | 7.50 | 0.08 |
| 72 | L072V | V | 98.37 | 0.98 |
| 72 | L072C | C | 73.50 | 0.73 |
| 72 | L072K | K | 72.20 | 0.72 |
| 72 | L072R | R | 61.79 | 0.62 |
| 72 | L072H | H | 47.06 | 0.47 |
| 72 | L072M | M | 44.46 | 0.44 |
| 72 | L072N | N | 43.42 | 0.43 |
| 72 | L072T | T | 38.32 | 0.38 |
| 72 | L072G | G | 34.67 | 0.35 |
| 72 | L072Q | Q | 30.17 | 0.30 |
| 72 | L072Y | Y | 29.73 | 0.30 |
| 72 | L072W | W | 28.66 | 0.29 |
| 72 | L072D | D | 27.32 | 0.27 |
| 72 | L072E | E | 24.56 | 0.25 |
| 72 | L072S | S | 23.76 | 0.24 |
| 72 | L072A | A | 8.70 | 0.09 |
| 72 | L072P | P | 6.61 | 0.07 |
| 73 | H073W | W | 75.35 | 0.75 |
| 73 | H073S | S | 63.17 | 0.63 |
| 73 | H073F | F | 60.20 | 0.60 |
| 73 | H073K | K | 32.91 | 0.33 |
| 73 | H073C | C | 31.74 | 0.32 |
| 73 | H073R | R | 27.97 | 0.28 |
| 73 | H073T | T | 25.37 | 0.25 |
| 73 | H073G | G | 24.90 | 0.25 |
| 73 | H073Q | Q | 24.68 | 0.25 |
| 73 | H073V | V | 22.30 | 0.22 |
| 73 | H073N | N | 20.69 | 0.21 |
| 73 | H073M | M | 20.67 | 0.21 |
| 73 | H073I | I | 19.80 | 0.20 |
| 73 | H073L | L | 19.63 | 0.20 |
| 73 | H073D | D | 16.98 | 0.17 |
| 73 | H073P | P | 6.69 | 0.07 |
| 73 | H073Y | Y | 6.36 | 0.06 |
| 73 | H073A | A | 5.49 | 0.05 |
| 74 | E074Q | Q | 161.32 | 1.61 |
| 74 | E074R | R | 142.60 | 1.43 |
| 74 | E074V | V | 136.24 | 1.36 |
| 74 | E074K | K | 127.86 | 1.28 |
| 74 | E074A | A | 116.09 | 1.16 |
| 74 | E074I | I | 105.81 | 1.06 |
| 74 | E074S | S | 97.24 | 0.97 |
| 74 | E074T | T | 86.73 | 0.87 |
| 74 | E074C | C | 86.04 | 0.86 |
| 74 | E074H | H | 63.24 | 0.63 |
| 74 | E074W | W | 59.27 | 0.59 |
| 74 | E074L | L | 51.36 | 0.51 |
| 74 | E074Y | Y | 41.17 | 0.41 |
| 74 | E074F | F | 37.16 | 0.37 |
| 74 | E074G | G | 33.60 | 0.34 |
| 74 | E074D | D | 30.16 | 0.30 |
| 74 | E074P | P | 29.71 | 0.30 |
| 75 | F075Y | Y | 103.89 | 1.04 |
| 75 | F075W | W | 16.17 | 0.16 |
| 75 | F075M | M | 16.15 | 0.16 |
| 75 | F075P | P | 9.44 | 0.09 |
| 75 | F075L | L | 9.32 | 0.09 |
| 75 | F075H | H | 7.78 | 0.08 |
| 75 | F075C | C | 7.76 | 0.08 |
| 75 | F075T | T | 7.40 | 0.07 |
| 75 | F075K | K | 7.11 | 0.07 |
| 75 | F075S | S | 6.90 | 0.07 |
| 75 | F075R | R | 6.89 | 0.07 |
| 75 | F075N | N | 6.79 | 0.07 |
| 75 | F075G | G | 6.63 | 0.07 |
| 75 | F075E | E | 6.57 | 0.07 |
| 76 | E076K | K | 125.00 | 1.25 |
| 76 | E076S | S | 111.17 | 1.11 |
| 76 | E076T | T | 110.72 | 1.11 |
| 76 | E076H | H | 110.48 | 1.10 |
| 76 | E076N | N | 110.33 | 1.10 |
| 76 | E076D | D | 100.51 | 1.01 |
| 76 | E076R | R | 95.92 | 0.96 |
| 76 | E076Y | Y | 78.30 | 0.78 |
| 76 | E076L | L | 68.68 | 0.69 |
| 76 | E076C | C | 62.01 | 0.62 |
| 76 | E076M | M | 60.90 | 0.61 |
| 76 | E076G | G | 60.13 | 0.60 |
| 76 | E076A | A | 58.13 | 0.58 |
| 76 | E076F | F | 56.00 | 0.56 |
| 76 | E076V | V | 53.16 | 0.53 |
| 76 | E076I | I | 41.46 | 0.41 |
| 76 | E076W | W | 36.12 | 0.36 |
| 76 | E076P | P | 12.90 | 0.13 |
| 77 | T077N | N | 137.52 | 1.38 |
| 77 | T077H | H | 121.65 | 1.22 |
| 77 | T077Y | Y | 89.82 | 0.90 |

TABLE 2-continued

| POSITION* | VARIANT CODE | VARIANT AMINO ACID | PROTEIN CONCENTRATION | ACTIVITY RATIO# |
|---|---|---|---|---|
| 77 | T077S | S | 86.50 | 0.87 |
| 77 | T077R | R | 86.26 | 0.86 |
| 77 | T077W | W | 76.37 | 0.76 |
| 77 | T077E | E | 68.68 | 0.69 |
| 77 | T077C | C | 56.68 | 0.57 |
| 77 | T077M | M | 53.12 | 0.53 |
| 77 | T077F | F | 52.13 | 0.52 |
| 77 | T077A | A | 48.97 | 0.49 |
| 77 | T077G | G | 43.04 | 0.43 |
| 77 | T077K | K | 38.82 | 0.39 |
| 77 | T077I | I | 28.21 | 0.28 |
| 77 | T077V | V | 25.58 | 0.26 |
| 77 | T077L | L | 21.11 | 0.21 |
| 77 | T077P | P | 5.57 | 0.06 |
| 78 | I078T | T | 105.05 | 1.05 |
| 78 | I078F | F | 86.64 | 0.87 |
| 78 | I078L | L | 48.68 | 0.49 |
| 78 | I078V | V | 42.29 | 0.42 |
| 78 | I078H | H | 32.83 | 0.33 |
| 78 | I078C | C | 14.99 | 0.15 |
| 78 | I078Y | Y | 13.55 | 0.14 |
| 78 | I078S | S | 10.19 | 0.10 |
| 78 | I078W | W | 9.59 | 0.10 |
| 78 | I078A | A | 8.51 | 0.09 |
| 78 | I078G | G | 8.10 | 0.08 |
| 78 | I078K | K | 7.77 | 0.08 |
| 78 | I078P | P | 7.76 | 0.08 |
| 78 | I078R | R | 6.63 | 0.07 |
| 79 | P079S | S | 18.58 | 0.19 |
| 79 | P079Q | Q | 10.04 | 0.10 |
| 79 | P079M | M | 9.48 | 0.09 |
| 79 | P079K | K | 9.48 | 0.09 |
| 79 | P079R | R | 8.79 | 0.09 |
| 79 | P079G | G | 8.40 | 0.08 |
| 79 | P079E | E | 8.01 | 0.08 |
| 79 | P079T | T | 7.60 | 0.08 |
| 79 | P079V | V | 7.38 | 0.07 |
| 79 | P079L | L | 6.94 | 0.07 |
| 79 | P079C | C | 6.59 | 0.07 |
| 79 | P079A | A | 6.54 | 0.07 |
| 79 | P079I | I | 5.84 | 0.06 |
| 80 | V080C | C | 57.46 | 0.57 |
| 80 | V080I | I | 21.08 | 0.21 |
| 80 | V080T | T | 20.20 | 0.20 |
| 80 | V080S | S | 10.00 | 0.10 |
| 80 | V080L | L | 9.00 | 0.09 |
| 80 | V080E | E | 7.00 | 0.07 |
| 80 | V080M | M | 7.00 | 0.07 |
| 80 | V080Y | Y | 7.00 | 0.07 |
| 80 | V080N | N | 6.44 | 0.06 |
| 80 | V080W | W | 6.32 | 0.06 |
| 80 | V080P | P | 6.04 | 0.06 |
| 80 | V080D | D | 6.00 | 0.06 |
| 80 | V080G | G | 6.00 | 0.06 |
| 80 | V080H | H | 6.00 | 0.06 |
| 80 | V080K | K | 6.00 | 0.06 |
| 80 | V080R | R | 6.00 | 0.06 |
| 81 | L081V | V | 49.01 | 0.49 |
| 81 | L081A | A | 41.20 | 0.41 |
| 81 | L081M | M | 26.29 | 0.26 |
| 81 | L081T | T | 15.28 | 0.15 |
| 81 | L081F | F | 11.66 | 0.12 |
| 81 | L081W | W | 9.72 | 0.10 |
| 81 | L081Y | Y | 8.23 | 0.08 |
| 81 | L081S | S | 7.53 | 0.08 |
| 81 | L081P | P | 7.23 | 0.07 |
| 81 | L081D | D | 6.93 | 0.07 |
| 81 | L081G | G | 6.62 | 0.07 |
| 81 | L081E | E | 6.60 | 0.07 |
| 81 | L081H | H | 5.90 | 0.06 |
| 81 | L081R | R | 5.68 | 0.06 |
| 82 | S082L | L | 129.13 | 1.29 |
| 82 | S082Q | Q | 128.15 | 1.28 |
| 82 | S082V | V | 103.94 | 1.04 |
| 82 | S082H | H | 97.35 | 0.97 |
| 82 | S082Y | Y | 91.12 | 0.91 |
| 82 | S082W | W | 88.77 | 0.89 |
| 82 | S082A | A | 87.22 | 0.87 |
| 82 | S082E | E | 85.81 | 0.86 |
| 82 | S082F | F | 81.39 | 0.81 |
| 82 | S082C | C | 79.80 | 0.80 |
| 82 | S082N | N | 61.37 | 0.61 |
| 82 | S082R | R | 58.97 | 0.59 |
| 82 | S082G | G | 54.28 | 0.54 |
| 82 | S082T | T | 54.07 | 0.54 |
| 82 | S082D | D | 18.02 | 0.18 |
| 82 | S082P | P | 6.19 | 0.06 |
| 83 | V083N | N | 109.58 | 1.10 |
| 83 | V083Y | Y | 102.00 | 1.02 |
| 83 | V083L | L | 97.61 | 0.98 |
| 83 | V083G | G | 42.23 | 0.42 |
| 83 | V083H | H | 33.13 | 0.33 |
| 83 | V083K | K | 11.63 | 0.12 |
| 83 | V083C | C | 10.69 | 0.11 |
| 83 | V083T | T | 7.51 | 0.08 |
| 83 | V083Q | Q | 7.00 | 0.07 |
| 83 | V083D | D | 6.61 | 0.07 |
| 83 | V083I | I | 6.32 | 0.06 |
| 83 | V083M | M | 6.20 | 0.06 |
| 83 | V083R | R | 6.04 | 0.06 |
| 83 | V083E | E | 5.77 | 0.06 |
| 83 | V083P | P | 5.67 | 0.06 |
| 83 | V083S | S | 4.97 | 0.05 |
| 83 | V083W | W | 4.69 | 0.05 |
| 83 | V083F | F | 4.62 | 0.05 |
| 83 | V083A | A | 4.61 | 0.05 |
| 84 | E084L | L | 153.83 | 1.54 |
| 84 | E084K | K | 150.95 | 1.51 |
| 84 | E084V | V | 148.36 | 1.48 |
| 84 | E084M | M | 139.82 | 1.40 |
| 84 | E084S | S | 135.46 | 1.35 |
| 84 | E084A | A | 127.39 | 1.27 |
| 84 | E084G | G | 124.12 | 1.24 |
| 84 | E084T | T | 123.30 | 1.23 |
| 84 | E084R | R | 116.66 | 1.17 |
| 84 | E084F | F | 111.03 | 1.11 |
| 84 | E084Q | Q | 101.46 | 1.01 |
| 84 | E084N | N | 100.11 | 1.00 |
| 84 | E084W | W | 98.81 | 0.99 |
| 84 | E084I | I | 98.06 | 0.98 |
| 84 | E084C | C | 95.71 | 0.96 |
| 84 | E084Y | Y | 89.76 | 0.90 |
| 84 | E084H | H | 75.48 | 0.75 |
| 84 | E084D | D | 50.64 | 0.51 |
| 84 | E084P | P | 7.96 | 0.08 |
| 85 | L085F | F | 100.71 | 1.01 |
| 85 | L085V | V | 87.45 | 0.87 |
| 85 | L085A | A | 66.38 | 0.66 |
| 85 | L085G | G | 41.13 | 0.41 |
| 85 | L085T | T | 27.10 | 0.27 |
| 85 | L085Q | Q | 12.11 | 0.12 |
| 85 | L085N | N | 11.63 | 0.12 |
| 85 | L085R | R | 10.96 | 0.11 |
| 85 | L085W | W | 8.95 | 0.09 |
| 85 | L085H | H | 7.59 | 0.08 |
| 85 | L085E | E | 6.71 | 0.07 |
| 85 | L085K | K | 6.71 | 0.07 |
| 86 | S086R | R | 133.45 | 1.33 |
| 86 | S086D | D | 124.54 | 1.25 |
| 86 | S086K | K | 120.11 | 1.20 |
| 86 | S086N | N | 118.58 | 1.19 |
| 86 | S086A | A | 114.90 | 1.15 |
| 86 | S086C | C | 94.83 | 0.95 |
| 86 | S086L | L | 80.83 | 0.81 |
| 86 | S086M | M | 77.93 | 0.78 |
| 86 | S086Q | Q | 77.62 | 0.78 |
| 86 | S086E | E | 61.08 | 0.61 |
| 86 | S086I | I | 45.96 | 0.46 |
| 86 | S086G | G | 43.12 | 0.43 |
| 86 | S086P | P | 40.52 | 0.41 |
| 87 | P087K | K | 89.04 | 0.89 |
| 87 | P087R | R | 62.86 | 0.63 |

TABLE 2-continued

| POSITION* | VARIANT CODE | VARIANT AMINO ACID | PROTEIN CONCENTRATION | ACTIVITY RATIO# |
|---|---|---|---|---|
| 87 | P087T | T | 58.88 | 0.59 |
| 87 | P087H | H | 58.22 | 0.58 |
| 87 | P087S | S | 56.23 | 0.56 |
| 87 | P087N | N | 51.90 | 0.52 |
| 87 | P087V | V | 47.19 | 0.47 |
| 87 | P087Q | Q | 46.90 | 0.47 |
| 87 | P087I | I | 38.44 | 0.38 |
| 87 | P087G | G | 35.49 | 0.35 |
| 87 | P087M | M | 32.83 | 0.33 |
| 87 | P087D | D | 27.06 | 0.27 |
| 87 | P087L | L | 25.98 | 0.26 |
| 87 | P087W | W | 15.17 | 0.15 |
| 88 | E088P | P | 128.01 | 1.28 |
| 88 | E088D | D | 103.64 | 1.04 |
| 88 | E088G | G | 98.73 | 0.99 |
| 88 | E088I | I | 76.72 | 0.77 |
| 88 | E088Y | Y | 73.31 | 0.73 |
| 88 | E088R | R | 71.94 | 0.72 |
| 88 | E088T | T | 71.19 | 0.71 |
| 88 | E088V | V | 69.78 | 0.70 |
| 88 | E088W | W | 59.58 | 0.60 |
| 88 | E088S | S | 57.12 | 0.57 |
| 88 | E088Q | Q | 45.20 | 0.45 |
| 88 | E088N | N | 32.31 | 0.32 |
| 88 | E088H | H | 31.97 | 0.32 |
| 88 | E088L | L | 28.70 | 0.29 |
| 88 | E088K | K | 24.60 | 0.25 |
| 89 | D089K | K | 110.11 | 1.10 |
| 89 | D089H | H | 101.55 | 1.02 |
| 89 | D089A | A | 97.39 | 0.97 |
| 89 | D089N | N | 88.63 | 0.89 |
| 89 | D089C | C | 86.69 | 0.87 |
| 89 | D089S | S | 68.40 | 0.68 |
| 89 | D089M | M | 60.16 | 0.60 |
| 89 | D089T | T | 57.25 | 0.57 |
| 89 | D089R | R | 56.85 | 0.57 |
| 89 | D089F | F | 56.61 | 0.57 |
| 89 | D089Q | Q | 56.61 | 0.57 |
| 89 | D089G | G | 50.16 | 0.50 |
| 89 | D089V | V | 49.23 | 0.49 |
| 89 | D089E | E | 38.22 | 0.38 |
| 89 | D089L | L | 10.85 | 0.11 |
| 89 | D089P | P | 7.52 | 0.08 |
| 90 | V090K | K | 93.59 | 0.94 |
| 90 | V090A | A | 77.43 | 0.77 |
| 90 | V090L | L | 74.46 | 0.74 |
| 90 | V090R | R | 70.69 | 0.71 |
| 90 | V090I | I | 68.15 | 0.68 |
| 90 | V090C | C | 56.98 | 0.57 |
| 90 | V090T | T | 51.24 | 0.51 |
| 90 | V090S | S | 23.79 | 0.24 |
| 90 | V090M | M | 23.60 | 0.24 |
| 90 | V090H | H | 21.17 | 0.21 |
| 90 | V090Y | Y | 14.44 | 0.14 |
| 90 | V090F | F | 13.27 | 0.13 |
| 90 | V090W | W | 11.98 | 0.12 |
| 90 | V090G | G | 10.52 | 0.11 |
| 90 | V090P | P | 7.80 | 0.08 |
| 90 | V090N | N | 7.52 | 0.08 |
| 90 | V090D | D | 7.09 | 0.07 |
| 91 | D091E | E | 148.69 | 1.49 |
| 91 | D091P | P | 144.01 | 1.44 |
| 91 | D091A | A | 142.94 | 1.43 |
| 91 | D091T | T | 136.68 | 1.37 |
| 91 | D091N | N | 124.34 | 1.24 |
| 91 | D091K | K | 118.47 | 1.18 |
| 91 | D091W | W | 108.37 | 1.08 |
| 91 | D091R | R | 107.58 | 1.08 |
| 91 | D091F | F | 104.13 | 1.04 |
| 91 | D091M | M | 98.03 | 0.98 |
| 91 | D091C | C | 97.38 | 0.97 |
| 91 | D091V | V | 87.03 | 0.87 |
| 91 | D091L | L | 81.60 | 0.82 |
| 91 | D091G | G | 18.66 | 0.19 |
| 91 | D091S | S | 5.81 | 0.06 |
| 92 | A092R | R | 139.58 | 1.40 |
| 92 | A092K | K | 135.47 | 1.35 |
| 92 | A092T | T | 134.11 | 1.34 |
| 92 | A092M | M | 132.58 | 1.33 |
| 92 | A092V | V | 130.35 | 1.30 |
| 92 | A092Q | Q | 121.93 | 1.22 |
| 92 | A092I | I | 119.20 | 1.19 |
| 92 | A092L | L | 117.04 | 1.17 |
| 92 | A092S | S | 105.71 | 1.06 |
| 92 | A092E | E | 97.94 | 0.98 |
| 92 | A092C | C | 89.25 | 0.89 |
| 92 | A092H | H | 88.18 | 0.88 |
| 92 | A092Y | Y | 84.08 | 0.84 |
| 92 | A092D | D | 83.51 | 0.84 |
| 92 | A092F | F | 76.69 | 0.77 |
| 92 | A092W | W | 70.16 | 0.70 |
| 92 | A092P | P | 8.53 | 0.09 |
| 92 | A092G | G | 7.42 | 0.07 |
| 93 | L093F | F | 60.69 | 0.61 |
| 93 | L093I | I | 53.14 | 0.53 |
| 93 | L093M | M | 51.15 | 0.51 |
| 93 | L093V | V | 44.68 | 0.45 |
| 93 | L093Y | Y | 12.17 | 0.12 |
| 93 | L093W | W | 11.12 | 0.11 |
| 93 | L093A | A | 11.07 | 0.11 |
| 93 | L093T | T | 9.55 | 0.10 |
| 93 | L093N | N | 7.93 | 0.08 |
| 93 | L093R | R | 7.73 | 0.08 |
| 93 | L093Q | Q | 7.40 | 0.07 |
| 93 | L093K | K | 7.36 | 0.07 |
| 93 | L093G | G | 7.31 | 0.07 |
| 93 | L093E | E | 7.18 | 0.07 |
| 93 | L093P | P | 7.17 | 0.07 |
| 93 | L093H | H | 6.92 | 0.07 |
| 93 | L093S | S | 6.62 | 0.07 |
| 93 | L093C | C | 6.43 | 0.06 |
| 94 | E094A | A | 130.00 | 1.30 |
| 94 | E094M | M | 127.00 | 1.27 |
| 94 | E094T | T | 125.00 | 1.25 |
| 94 | E094R | R | 115.00 | 1.15 |
| 94 | E094S | S | 111.00 | 1.11 |
| 94 | E094L | L | 103.00 | 1.03 |
| 94 | E094F | F | 96.41 | 0.96 |
| 94 | E094V | V | 94.00 | 0.94 |
| 94 | E094C | C | 88.52 | 0.89 |
| 94 | E094N | N | 86.00 | 0.86 |
| 94 | E094D | D | 76.35 | 0.76 |
| 94 | E094G | G | 71.00 | 0.71 |
| 94 | E094P | P | 15.00 | 0.15 |
| 94 | E094I | I | 6.00 | 0.06 |
| 94 | E094K | K | 6.00 | 0.06 |
| 95 | L095E | E | 144.50 | 1.44 |
| 95 | L095R | R | 143.47 | 1.43 |
| 95 | L095K | K | 132.53 | 1.33 |
| 95 | L095S | S | 127.82 | 1.28 |
| 95 | L095C | C | 126.67 | 1.27 |
| 95 | L095A | A | 123.21 | 1.23 |
| 95 | L095T | T | 119.38 | 1.19 |
| 95 | L095D | D | 112.59 | 1.13 |
| 95 | L095G | G | 107.90 | 1.08 |
| 95 | L095V | V | 101.75 | 1.02 |
| 95 | L095H | H | 101.25 | 1.01 |
| 95 | L095Y | Y | 72.15 | 0.72 |
| 95 | L095I | I | 66.43 | 0.66 |
| 95 | L095F | F | 55.60 | 0.56 |
| 95 | L095W | W | 54.88 | 0.55 |
| 95 | L095M | M | 49.85 | 0.50 |
| 95 | L095P | P | 43.73 | 0.44 |
| 95 | L095N | N | 7.87 | 0.08 |
| 96 | D096Y | Y | 154.21 | 1.54 |
| 96 | D096H | H | 154.17 | 1.54 |
| 96 | D096C | C | 131.97 | 1.32 |
| 96 | D096S | S | 125.64 | 1.26 |
| 96 | D096L | L | 122.29 | 1.22 |
| 96 | D096E | E | 115.11 | 1.15 |
| 96 | D096I | I | 111.95 | 1.12 |
| 96 | D096W | W | 111.27 | 1.11 |

TABLE 2-continued

| POSITION* | VARIANT CODE | VARIANT AMINO ACID | PROTEIN CON-CENTRATION | ACTIVITY RATIO# |
|---|---|---|---|---|
| 96 | D096V | V | 103.05 | 1.03 |
| 96 | D096T | T | 91.78 | 0.92 |
| 96 | D096F | F | 81.46 | 0.81 |
| 96 | D096G | G | 66.73 | 0.67 |
| 96 | D096R | R | 54.25 | 0.54 |
| 96 | D096P | P | 30.89 | 0.31 |
| 96 | D096K | K | 24.76 | 0.25 |
| 96 | D096M | M | 7.93 | 0.08 |
| 96 | D096N | N | 7.71 | 0.08 |
| 97 | P097E | E | 73.24 | 0.73 |
| 97 | P097S | S | 66.40 | 0.66 |
| 97 | P097D | D | 63.49 | 0.63 |
| 97 | P097A | A | 58.83 | 0.59 |
| 97 | P097K | K | 57.21 | 0.57 |
| 97 | P097Q | Q | 54.30 | 0.54 |
| 97 | P097N | N | 47.24 | 0.47 |
| 97 | P097G | G | 46.89 | 0.47 |
| 97 | P097T | T | 45.56 | 0.46 |
| 97 | P097R | R | 45.09 | 0.45 |
| 97 | P097M | M | 33.57 | 0.34 |
| 97 | P097C | C | 29.31 | 0.29 |
| 97 | P097V | V | 22.34 | 0.22 |
| 97 | P097Y | Y | 21.56 | 0.22 |
| 97 | P097F | F | 20.98 | 0.21 |
| 97 | P097L | L | 19.17 | 0.19 |
| 97 | P097I | I | 18.76 | 0.19 |
| 97 | P097W | W | 15.10 | 0.15 |
| 98 | A098R | R | 132.47 | 1.32 |
| 98 | A098K | K | 131.64 | 1.32 |
| 98 | A098D | D | 102.97 | 1.03 |
| 98 | A098L | L | 102.06 | 1.02 |
| 98 | A098T | T | 91.56 | 0.92 |
| 98 | A098G | G | 89.92 | 0.90 |
| 98 | A098V | V | 70.86 | 0.71 |
| 98 | A098M | M | 48.09 | 0.48 |
| 98 | A098F | F | 40.13 | 0.40 |
| 98 | A098E | E | 36.13 | 0.36 |
| 99 | I099V | V | 77.11 | 0.77 |
| 99 | I099F | F | 13.83 | 0.14 |
| 99 | I099L | L | 13.75 | 0.14 |
| 99 | I099T | T | 10.36 | 0.10 |
| 99 | I099P | P | 7.86 | 0.08 |
| 99 | I099Q | Q | 7.27 | 0.07 |
| 99 | I099E | E | 7.21 | 0.07 |
| 99 | I099K | K | 6.92 | 0.07 |
| 99 | I099A | A | 6.85 | 0.07 |
| 99 | I099H | H | 6.53 | 0.07 |
| 99 | I099D | D | 6.44 | 0.06 |
| 99 | I099S | S | 6.42 | 0.06 |
| 99 | I099G | G | 6.26 | 0.06 |
| 99 | I099W | W | 6.22 | 0.06 |
| 99 | I099R | R | 5.85 | 0.06 |
| 99 | I099Y | Y | 5.59 | 0.06 |
| 100 | S100A | A | 103.00 | 1.03 |
| 100 | S100V | V | 97.27 | 0.97 |
| 100 | S100R | R | 91.59 | 0.92 |
| 100 | S100E | E | 87.00 | 0.87 |
| 100 | S100T | T | 81.00 | 0.81 |
| 100 | S100C | C | 75.00 | 0.75 |
| 100 | S100L | L | 61.00 | 0.61 |
| 100 | S100H | H | 59.00 | 0.59 |
| 100 | S100I | I | 53.00 | 0.53 |
| 100 | S100W | W | 43.04 | 0.43 |
| 100 | S100G | G | 35.00 | 0.35 |
| 100 | S100Q | Q | 21.00 | 0.21 |
| 100 | S100F | F | 13.00 | 0.13 |
| 100 | S100M | M | 7.00 | 0.07 |
| 101 | Y101F | F | 79.08 | 0.79 |
| 101 | Y101H | H | 34.40 | 0.34 |
| 101 | Y101R | R | 8.50 | 0.09 |
| 101 | Y101T | T | 7.52 | 0.08 |
| 101 | Y101C | C | 7.50 | 0.08 |
| 101 | Y101Q | Q | 7.46 | 0.07 |
| 101 | Y101S | S | 7.43 | 0.07 |
| 101 | Y101L | L | 7.42 | 0.07 |
| 101 | Y101N | N | 7.33 | 0.07 |
| 101 | Y101G | G | 7.03 | 0.07 |
| 101 | Y101E | E | 6.76 | 0.07 |
| 101 | Y101P | P | 6.39 | 0.06 |
| 102 | I102L | L | 32.85 | 0.33 |
| 102 | I102T | T | 12.31 | 0.12 |
| 102 | I102A | A | 11.19 | 0.11 |
| 102 | I102F | F | 7.57 | 0.08 |
| 102 | I102P | P | 7.53 | 0.08 |
| 102 | I102G | G | 6.21 | 0.06 |
| 102 | I102K | K | 5.78 | 0.06 |
| 102 | I102S | S | 5.77 | 0.06 |
| 102 | I102R | R | 5.60 | 0.06 |
| 102 | I102Y | Y | 5.40 | 0.05 |
| 102 | I102H | H | 5.15 | 0.05 |
| 102 | I102E | E | 5.10 | 0.05 |
| 102 | I102Q | Q | 4.91 | 0.05 |
| 103 | E103T | T | 113.38 | 1.13 |
| 103 | E103P | P | 111.36 | 1.11 |
| 103 | E103S | S | 86.19 | 0.86 |
| 103 | E103G | G | 81.52 | 0.82 |
| 103 | E103D | D | 56.43 | 0.56 |
| 103 | E103H | H | 33.35 | 0.33 |
| 103 | E103Q | Q | 10.36 | 0.10 |
| 103 | E103I | I | 8.00 | 0.08 |
| 103 | E103A | A | 7.62 | 0.08 |
| 103 | E103K | K | 7.55 | 0.08 |
| 103 | E103L | L | 7.25 | 0.07 |
| 103 | E103W | W | 7.22 | 0.07 |
| 103 | E103C | C | 7.10 | 0.07 |
| 103 | E103F | F | 6.98 | 0.07 |
| 103 | E103V | V | 6.88 | 0.07 |
| 103 | E103R | R | 6.04 | 0.06 |
| 104 | E104P | P | 124.98 | 1.25 |
| 104 | E104Q | Q | 98.83 | 0.99 |
| 104 | E104L | L | 95.33 | 0.95 |
| 104 | E104Y | Y | 91.66 | 0.92 |
| 104 | E104H | H | 87.15 | 0.87 |
| 104 | E104S | S | 81.74 | 0.82 |
| 104 | E104A | A | 76.42 | 0.76 |
| 104 | E104F | F | 71.58 | 0.72 |
| 104 | E104T | T | 69.53 | 0.70 |
| 104 | E104C | C | 64.06 | 0.64 |
| 104 | E104V | V | 57.67 | 0.58 |
| 104 | E104N | N | 48.45 | 0.48 |
| 104 | E104W | W | 43.19 | 0.43 |
| 104 | E104G | G | 33.84 | 0.34 |
| 105 | D105M | M | 25.47 | 0.25 |
| 105 | D105T | T | 16.88 | 0.17 |
| 105 | D105E | E | 14.77 | 0.15 |
| 105 | D105P | P | 7.10 | 0.07 |
| 105 | D105C | C | 6.97 | 0.07 |
| 105 | D105G | G | 6.51 | 0.07 |
| 105 | D105S | S | 6.19 | 0.06 |
| 105 | D105F | F | 5.83 | 0.06 |
| 105 | D105L | L | 5.71 | 0.06 |
| 105 | D105W | W | 5.66 | 0.06 |
| 105 | D105Y | Y | 5.36 | 0.05 |
| 106 | A106F | F | 108.54 | 1.09 |
| 106 | A106K | K | 106.67 | 1.07 |
| 106 | A106V | V | 106.21 | 1.06 |
| 106 | A106L | L | 105.12 | 1.05 |
| 106 | A106M | M | 102.59 | 1.03 |
| 106 | A106C | C | 95.21 | 0.95 |
| 106 | A106S | S | 94.82 | 0.95 |
| 106 | A106I | I | 88.65 | 0.89 |
| 106 | A106E | E | 84.86 | 0.85 |
| 106 | A106N | N | 80.65 | 0.81 |
| 106 | A106G | G | 66.53 | 0.67 |
| 106 | A106D | D | 44.78 | 0.45 |
| 107 | E107Q | Q | 112.74 | 1.13 |
| 107 | E107P | P | 102.05 | 1.02 |
| 107 | E107V | V | 99.68 | 1.00 |
| 107 | E107S | S | 99.06 | 0.99 |
| 107 | E107T | T | 93.40 | 0.93 |
| 107 | E107H | H | 89.38 | 0.89 |
| 107 | E107R | R | 87.40 | 0.87 |

TABLE 2-continued

| POSITION* | VARIANT CODE | VARIANT AMINO ACID | PROTEIN CON-CENTRATION | ACTIVITY RATIO# |
|---|---|---|---|---|
| 107 | E107L | L | 82.19 | 0.82 |
| 107 | E107G | G | 65.90 | 0.66 |
| 107 | E107C | C | 34.35 | 0.34 |
| 107 | E107D | D | 6.32 | 0.06 |
| 107 | E107Y | Y | 5.97 | 0.06 |
| 107 | E107I | I | 5.76 | 0.06 |
| 108 | V108I | I | 96.87 | 0.97 |
| 108 | V108A | A | 81.56 | 0.82 |
| 108 | V108L | L | 73.95 | 0.74 |
| 108 | V108C | C | 73.59 | 0.74 |
| 108 | V108T | T | 54.76 | 0.55 |
| 108 | V108G | G | 34.72 | 0.35 |
| 108 | V108E | E | 13.15 | 0.13 |
| 108 | V108S | S | 6.94 | 0.07 |
| 108 | V108H | H | 6.42 | 0.06 |
| 108 | V108P | P | 6.03 | 0.06 |
| 108 | V108Q | Q | 6.03 | 0.06 |
| 108 | V108R | R | 5.94 | 0.06 |
| 109 | T109Y | Y | 151.13 | 1.51 |
| 109 | T109E | E | 140.77 | 1.41 |
| 109 | T109G | G | 135.65 | 1.36 |
| 109 | T109N | N | 135.23 | 1.35 |
| 109 | T109S | S | 125.47 | 1.25 |
| 109 | T109M | M | 123.65 | 1.24 |
| 109 | T109R | R | 121.74 | 1.22 |
| 109 | T109Q | Q | 105.15 | 1.05 |
| 109 | T109W | W | 102.35 | 1.02 |
| 109 | T109K | K | 98.87 | 0.99 |
| 109 | T109L | L | 95.89 | 0.96 |
| 109 | T109A | A | 31.57 | 0.32 |
| 110 | T110V | V | 117.34 | 1.17 |
| 110 | T110L | L | 113.17 | 1.13 |
| 110 | T110P | P | 112.26 | 1.12 |
| 110 | T110M | M | 110.23 | 1.10 |
| 110 | T110C | C | 98.41 | 0.98 |
| 110 | T110K | K | 97.01 | 0.97 |
| 110 | T110E | E | 80.71 | 0.81 |
| 110 | T110G | G | 80.05 | 0.80 |
| 110 | T110R | R | 79.50 | 0.80 |
| 110 | T110N | N | 74.55 | 0.75 |
| 110 | T110Q | Q | 57.23 | 0.57 |
| 110 | T110S | S | 5.27 | 0.05 |
| 110 | T110W | W | 4.82 | 0.05 |
| 111 | M111N | N | 145.51 | 1.46 |
| 111 | M111T | T | 138.47 | 1.38 |
| 111 | M111Q | Q | 134.85 | 1.35 |
| 111 | M111L | L | 134.45 | 1.34 |
| 111 | M111W | W | 132.12 | 1.32 |
| 111 | M111E | E | 130.67 | 1.31 |
| 111 | M111C | C | 113.25 | 1.13 |
| 111 | M111G | G | 101.14 | 1.01 |
| 111 | M111I | I | 100.83 | 1.01 |
| 111 | M111V | V | 93.69 | 0.94 |
| 111 | M111R | R | 74.46 | 0.74 |
| 111 | M111K | K | 70.17 | 0.70 |
| 111 | M111P | P | 31.70 | 0.32 |

*"POSITION" refers to the amino acid position as numbered in the full-length V049 precursor protease of SEQ ID NO: 13. Positions 1-27 refer to amino acids at positions in the signal peptide portion of the V049 precursor enzyme, and positions 28-111 refer to the amino acids at positions in the pro region of the V049 precursor enzyme.
Activity Ratio is the Activity of the mature protease processed from a modified protease divided by the activity of the mature protease processed from an unmodified precursor protease.

Example 4

In this example, the pro region of the subtilisin from *Bacillus lentus*, called GG36 (SEQ ID NO:244), was mutagenized at position 33 and position 59 using the same experimental protocol described in the examples above. The precursor polynucleotide sequence (SEQ ID NO:240) was mutated, a construct was made, and the modifications were tested for increasing the protease expression as described above.

The results showed that amino acid substitutions E33G, E33Q and E33V all increased the production of the wild-type mature GG36 protease by at least 50% above that of the unmodified precursor. The mutation H32K increased the production of the wild-type mature protease by 20%.

These results show that mutations in the pro region of a full-length protease can improve the expression not only of variant precursor proteins, but also of naturally-occurring enzymes.

We claim:

1. An isolated polynucleotide encoding a modified protease, wherein the polynucleotide comprises a first polynucleotide sequence 5' and operably linked to a second polynucleotide sequence, wherein the first polynucleotide sequence encodes a modified pro sequence of the protease and the second polynucleotide sequence encodes a mature sequence of the protease, wherein the amino acid sequence encoded by the first polynucleotide sequence comprises at least 95% sequence identity to SEQ ID NO:7, SEQ ID NO:15 or SEQ ID NO:246 and comprises an amino acid substitution at amino acid position E6 of SEQ ID NO:7, SEQ ID NO:15 or SEQ ID NO:246, wherein the substitution of E6 is selected from the group consisting of E6D, E6I, E6S, E6N, E6K, E6H, E6Q and E6R, and the second polynucleotide sequence encodes a mature sequence of the protease, wherein the amino acid sequence encoded by the second polynucleotide comprises at least 70% amino acid sequence identity with a mature protease comprising an amino acid sequence of SEQ ID NO:8, 16 or 247.

2. The isolated polynucleotide of claim 1, further comprising a third polynucleotide sequence positioned 5' and operably linked to the first polynucleotide sequence, wherein the third polynucleotide sequence encodes a signal peptide comprising an amino acid sequence selected from the group consisting of SEQ ID NO:6, SEQ ID NO:14 and SEQ ID NO:245.

3. A vector comprising the modified polynucleotide of claim 1.

4. A host cell transformed with the vector of claim 3.

5. The host cell of claim 4, wherein said host cell is a microorganism.

6. The host cell of claim 4, wherein said host cell is a microorganism selected from the group consisting of Bacillus sp., Streptomyces sp., Escherichia sp. and Aspergillus sp.

7. The host cell of claim 4, wherein said host cell is a B. subtilis cell.

8. A method for producing a protease in a microorganism comprising culturing the host cell of claim 4 under suitable conditions to allow the production of said modified protease by said host cell.

9. The method of claim 8, wherein the mature region of said modified full length protease produced by said host cell is recovered.

10. The method of claim 8, wherein said host cell is selected from the group consisting of *B. licheniformis, B. lentus, B. subtilis, B. amyloliquefaciens, B. brevis, B. stearothermophilus, B. clausii, B. alkalophilus, B. halodurans, B. coagulans, B. circulans, B. pumilus,* and *B. thuringiensis*.

11. The method of claim 8, wherein said host cell is a *B. subtilis* host cell.

12. The method of claim 8, wherein said modified protease exhibits a ratio of production of at least 1.

13. A protease produced by the host cell of claim 4.

* * * * *

SEQUENCE LISTING

<160> NUMBER OF SEQ ID NOS: 247

<210> SEQ ID NO 1
<211> LENGTH: 1143
<212> TYPE: DNA
<213> ORGANISM: Bacillus clausii

<400> SEQUENCE: 1

```
atgaagaaac cgttggggaa aattgtcgca agcaccgcac tactcatttc tgttgctttt      60
agttcatcga tcgcatcggc tgctgaagaa gcaaaagaaa aatatttaat tggctttaat     120
gagcaggaag ctgtcagtga gtttgtagaa caagtagagg caaatgacga ggtcgccatt     180
ctctctgagg aagaggaagt cgaaattgaa ttgcttcatg aatttgaaac gattcctgtt     240
ttatccgttg agttaagccc agaagatgtg gacgcgcttg aactcgatcc agcgatttct     300
tatattgaag aggatgcaga agtaacgaca atggcgcaat cagtgccatg gggaattagc     360
cgtgtgcaag ccccagctgc ccataaccgt ggattgacag gttctggtgt aaaagttgct     420
gtcctcgata caggtatttc cactcatcca gacttaaata ttcgtggtgg cgctagcttt     480
gtaccagggg aaccatccac tcaagatggg aatgggcatg gcacgcatgt ggctgggacg     540
```

-continued

```
attgctgctt taaacaattc gattggcgtt cttggcgtag caccgaacgc ggaactatac    600
gctgttaaag tattaggggc gagcggttca ggttcggtca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta gaggcgttct tgttgtagcg    780
gcatctggga attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc ggcaacacgc   1140
taa                                                                 1143

<210> SEQ ID NO 2
<211> LENGTH: 81
<212> TYPE: DNA
<213> ORGANISM: Bacillus clausii

<400> SEQUENCE: 2
atgaagaaac cgttggggaa aattgtcgca agcaccgcac tactcatttc tgttgctttt     60
agttcatcga tcgcatcggc t                                               81

<210> SEQ ID NO 3
<211> LENGTH: 252
<212> TYPE: DNA
<213> ORGANISM: Bacillus clausii

<400> SEQUENCE: 3
gctgaagaag caaaagaaaa atatttaatt ggctttaatg agcaggaagc tgtcagtgag     60
tttgtagaac aagtagaggc aaatgacgag gtcgccattc tctctgagga agaggaagtc    120
gaaattgaat tgcttcatga atttgaaacg attcctgttt tatccgttga gttaagccca    180
gaagatgtgg acgcgcttga actcgatcca gcgatttctt atattgaaga ggatgcagaa    240
gtaacgacaa tg                                                        252

<210> SEQ ID NO 4
<211> LENGTH: 810
<212> TYPE: DNA
<213> ORGANISM: Bacillus clausii

<400> SEQUENCE: 4
gcgcaatcag tgccatgggg aattagccgt gtgcaagccc cagctgccca taaccgtgga     60
ttgacaggtt ctggtgtaaa agttgctgtc ctcgatacag gtatttccac tcatccagac    120
ttaaatattc gtggtggcgc tagctttgta ccaggggaac catccactca agatgggaat    180
gggcatggca cgcatgtggc tgggacgatt gctgctttaa acaattcgat tggcgttctt    240
ggcgtagcac cgaacgcgga actatacgct gttaaagtat tagggcgag cggttcaggt    300 tcggtcagct cgattgccca aggattgaa tgggcaggga caatggcat gcacgttgct    360 aatttgagtt taggaagccc ttcgccaagt gccacacttg agcaagctgt taatagcgcg    420
acttctagag gcgttcttgt tgtagcggca tctgggaatt caggtgcagg ctcaatcagc    480
tatccggccc gttatgcgaa cgcaatggca gtcggagcta ctgaccaaaa caacaaccgc    540
```

```
gccagctttt cacagtatgg cgcagggctt gacattgtcg caccaggtgt aaacgtgcag        600
agcacatacc caggttcaac gtatgccagc ttaaacggta catcgatggc tactcctcat        660
gttgcaggtg cagcagccct tgttaaacaa aagaaaccat cttggtccaa tgtacaaatc        720
cgcaatcatc taaagaatac ggcaacgagc ttaggaagca cgaacttgta tggaagcgga        780
cttgtcaatg cagaagcggc aacacgctaa                                         810
```

<210> SEQ ID NO 5
<211> LENGTH: 371
<212> TYPE: PRT
<213> ORGANISM: Bacillus clausii

<400> SEQUENCE: 5

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Arg
            100                 105                 110

Val Gln Ala Pro Ala Ala His Asn Arg Gly Leu Thr Gly Ser Gly Val
        115                 120                 125

Lys Val Ala Val Leu Asp Thr Gly Ile Ser Thr His Pro Asp Leu Asn
130                 135                 140

Ile Arg Gly Gly Ala Ser Phe Val Pro Gly Glu Pro Ser Thr Gln Asp
145                 150                 155                 160

Gly Asn Gly His Gly Thr His Val Ala Gly Thr Ile Ala Ala Leu Asn
                165                 170                 175

Asn Ser Ile Gly Val Leu Gly Val Ala Pro Asn Ala Glu Leu Tyr Ala
            180                 185                 190

Val Lys Val Leu Gly Ala Ser Gly Ser Gly Ser Val Ser Ser Ile Ala
        195                 200                 205

Gln Gly Leu Glu Trp Ala Gly Asn Asn Gly Met His Val Ala Asn Leu
    210                 215                 220

Ser Leu Gly Ser Pro Ser Pro Ser Ala Thr Leu Glu Gln Ala Val Asn
225                 230                 235                 240

Ser Ala Thr Ser Arg Gly Val Leu Val Ala Ala Ser Gly Asn Ser
                245                 250                 255

Gly Ala Gly Ser Ile Ser Tyr Pro Ala Arg Tyr Ala Asn Ala Met Ala
            260                 265                 270

Val Gly Ala Thr Asp Gln Asn Asn Asn Arg Ala Ser Phe Ser Gln Tyr
        275                 280                 285

Gly Ala Gly Leu Asp Ile Val Ala Pro Gly Val Asn Val Gln Ser Thr
    290                 295                 300

Tyr Pro Gly Ser Thr Tyr Ala Ser Leu Asn Gly Thr Ser Met Ala Thr
305                 310                 315                 320

Pro His Val Ala Gly Ala Ala Ala Leu Val Lys Gln Lys Asn Pro Ser
```

```
                    325                 330                 335
Trp Ser Asn Val Gln Ile Arg Asn His Leu Lys Asn Thr Ala Thr Ser
                340                 345                 350

Leu Gly Ser Thr Asn Leu Tyr Gly Ser Gly Leu Val Asn Ala Glu Ala
            355                 360                 365

Ala Thr Arg
        370

<210> SEQ ID NO 6
<211> LENGTH: 27
<212> TYPE: PRT
<213> ORGANISM: Bacillus clausii

<400> SEQUENCE: 6

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 7
<211> LENGTH: 84
<212> TYPE: PRT
<213> ORGANISM: Bacillus clausii

<400> SEQUENCE: 7

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 8
<211> LENGTH: 260
<212> TYPE: PRT
<213> ORGANISM: Bacillus clausii

<400> SEQUENCE: 8

Arg Val Gln Ala Pro Ala Ala His Asn Arg Gly Leu Thr Gly Ser Gly
1               5                   10                  15

Val Lys Val Ala Val Leu Asp Thr Gly Ile Ser Thr His Pro Asp Leu
            20                  25                  30

Asn Ile Arg Gly Gly Ala Ser Phe Val Pro Gly Glu Pro Ser Thr Gln
        35                  40                  45

Asp Gly Asn Gly His Gly Thr His Val Ala Gly Thr Ile Ala Ala Leu
    50                  55                  60

Asn Asn Ser Ile Gly Val Leu Gly Val Ala Pro Asn Ala Glu Leu Tyr
65                  70                  75                  80

Ala Val Lys Val Leu Gly Ala Ser Gly Ser Gly Ser Val Ser Ser Ile
            85                  90                  95

Ala Gln Gly Leu Glu Trp Ala Gly Asn Asn Gly Met His Val Ala Asn
        100                 105                 110
```

```
Leu Ser Leu Gly Ser Pro Ser Pro Ser Ala Thr Leu Glu Gln Ala Val
            115                 120                 125
Asn Ser Ala Thr Ser Arg Gly Val Leu Val Val Ala Ala Ser Gly Asn
    130                 135                 140
Ser Gly Ala Gly Ser Ile Ser Tyr Pro Ala Arg Tyr Ala Asn Ala Met
145                 150                 155                 160
Ala Val Gly Ala Thr Asp Gln Asn Asn Asn Arg Ala Ser Phe Ser Gln
                165                 170                 175
Tyr Gly Ala Gly Leu Asp Ile Val Ala Pro Gly Val Asn Val Gln Ser
            180                 185                 190
Thr Tyr Pro Gly Ser Thr Tyr Ala Ser Leu Asn Gly Thr Ser Met Ala
        195                 200                 205
Thr Pro His Val Ala Gly Ala Ala Ala Leu Val Lys Gln Lys Asn Pro
    210                 215                 220
Ser Trp Ser Asn Val Gln Ile Arg Asn His Leu Lys Asn Thr Ala Thr
225                 230                 235                 240
Ser Leu Gly Ser Thr Asn Leu Tyr Gly Ser Gly Leu Val Asn Ala Glu
                245                 250                 255
Ala Ala Thr Arg
            260
```

<210> SEQ ID NO 9
<211> LENGTH: 1143
<212> TYPE: DNA
<213> ORGANISM: Bacillus clausii

<400> SEQUENCE: 9

```
gtgagaagca aaaaattgtg atcgtcgcg tcgaccgcac tactcatttc tgttgctttt      60
agttcatcga tcgcatcggc tgctgaagaa gcaaaagaaa atatttaat tggctttaat    120
gagcaggaag ctgtcagtga gtttgtagaa caagtagagg caaatgacga ggtcgccatt    180
ctctctgagg aagaggaagt cgaaattgaa ttgcttcatg aatttgaaac gattcctgtt    240
ttatccgttg agttaagccc agaagatgtg gacgcgcttg aactcgatcc agcgatttct    300
tatattgaag aggatgcaga agtaacgaca atggcgcaat cggtaccatg ggaattagc    360
cgtgtgcaag ccccagctgc ccataaccgt ggattgacag ttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggctgggacg    540
attgctgctt taaacaattc gattggcgtt cttggcgtag caccgaacgc ggaactatac    600
gctgttaaag tattaggggc gagcggttca ggttcggtca gctcgattgc ccaaggattg    660
gaatgggcag ggaacaatgt tatgcacgtt gctaatttga gtttaggact gcaggcacca    720
agtgccacac ttgagcaagc tgttaatagc gcgacttcta gaggcgttct tgttgtagcg    780
gcatctggga attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catccttggtc caatgtacaa atccgcaatc atctaaagaa tacggcaacg   1080
agcttaggaa gcacgaactt gtatggaagc ggacttgtca atgcagaagc ggcaacacgt   1140
taa                                                                 1143
```

<210> SEQ ID NO 10
<211> LENGTH: 81
<212> TYPE: DNA
<213> ORGANISM: Bacillus clausii

<400> SEQUENCE: 10

```
gtgagaagca aaaaattgtg gatcgtcgcg tcgaccgcac tactcatttc tgttgctttt    60
agttcatcga tcgcatcggc t                                              81
```

<210> SEQ ID NO 11
<211> LENGTH: 252
<212> TYPE: DNA
<213> ORGANISM: Bacillus clausii

<400> SEQUENCE: 11

```
gctgaagaag caaagaaaa atatttaatt ggctttaatg agcaggaagc tgtcagtgag    60
tttgtagaac aagtagaggc aaatgacgag gtcgccattc tctctgagga agaggaagtc   120
gaaattgaat tgcttcatga atttgaaacg attcctgttt tatccgttga gttaagccca   180
gaagatgtgg acgcgcttga actcgatcca gcgatttctt atattgaaga ggatgcagaa   240
gtaacgacaa tg                                                       252
```

<210> SEQ ID NO 12
<211> LENGTH: 810
<212> TYPE: DNA
<213> ORGANISM: Bacillus clausii

<400> SEQUENCE: 12

```
gcgcaatcgg taccatgggg aattagccgt gtgcaagccc cagctgccca taaccgtgga    60
ttgacaggtt ctggtgtaaa agttgctgtc ctcgatacag gtatttccac tcatccagac   120
ttaaatattc gtggtggcgc tagctttgta ccaggggaac catccactca agatgggaat   180
gggcatggca cgcatgtggc tgggacgatt gctgctttaa acaattcgat ggcgttctt   240 ggcgtagcac cgaacgcgga actatacgct gttaaagtat taggggcgag cggttcaggt   300
tcggtcagct cgattgccca aggattggaa tgggcaggga caatgttat gcacgttgct   360 aatttgagtt taggactgca ggcaccaagt gccacacttg agcaagctgt taatagcgcg   420
acttctagag gcgttcttgt tgtagcggca tctgggaatt caggtgcagg ctcaatcagc   480
tatccggccc gttatgcgaa cgcaatggca gtcggagcta ctgaccaaaa caacaaccgc   540
gccagctttt cacagtatgg cgcagggctt gacattgtcg caccaggtgt aaacgtgcag   600
agcacatacc aggttcaac gtatgccagc ttaaacggta catcgatggc tactcctcat   660
gttgcaggtg cagcagccct tgttaaacaa agaaacccat cttggtccaa tgtacaaatc   720
cgcaatcatc taaagaatac ggcaacgagc ttaggaagca cgaacttgta tggaagcgga   780
cttgtcaatg cagaagcggc aacacgttaa                                    810
```

<210> SEQ ID NO 13
<211> LENGTH: 380
<212> TYPE: PRT
<213> ORGANISM: Bacillus clausii

<400> SEQUENCE: 13

```
Val Arg Ser Lys Lys Leu Trp Ile Val Ala Ser Thr Ala Leu Leu Ile
 1               5                  10                  15

Ser Val Ala Phe Ser Ser Ser Ile Ala Ser Ala Ala Glu Glu Ala Lys
            20                  25                  30
```

```
Glu Lys Tyr Leu Ile Gly Phe Asn Glu Gln Ala Val Ser Glu Phe
             35                  40                  45

Val Glu Gln Val Glu Ala Asn Asp Glu Val Ala Ile Leu Ser Glu Glu
 50                  55                  60

Glu Glu Val Glu Ile Glu Leu Leu His Glu Phe Glu Thr Ile Pro Val
 65                  70                  75                  80

Leu Ser Val Glu Leu Ser Pro Glu Asp Val Asp Ala Leu Glu Leu Asp
                 85                  90                  95

Pro Ala Ile Ser Tyr Ile Glu Glu Asp Ala Glu Val Thr Thr Met Ala
             100                 105                 110

Gln Ser Val Pro Trp Gly Ile Ser Arg Val Gln Ala Pro Ala Ala His
             115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Asn Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
            210                 215                 220

Asn Asn Val Met His Val Ala Asn Leu Ser Leu Gly Leu Gln Ala Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380

<210> SEQ ID NO 14
<211> LENGTH: 27
<212> TYPE: PRT
<213> ORGANISM: Bacillus clausii

<400> SEQUENCE: 14

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala
            20                  25
```

<210> SEQ ID NO 15
<211> LENGTH: 84
<212> TYPE: PRT
<213> ORGANISM: Bacillus clausii

<400> SEQUENCE: 15

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Val Glu Ile Glu Leu Leu His Glu Phe
        35                  40                  45

Glu Thr Ile Pro Val Leu Ser Val Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 16
<211> LENGTH: 269
<212> TYPE: PRT
<213> ORGANISM: Bacillus clausii

<400> SEQUENCE: 16

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Val Met His Val Ala Asn Leu Ser Leu Gly Leu Gln Ala
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

```
Arg Asn His Leu Lys Asn Thr Ala Thr Ser Leu Gly Ser Thr Asn Leu
            245                 250                 255
Tyr Gly Ser Gly Leu Val Asn Ala Glu Ala Ala Thr Arg
        260                 265

<210> SEQ ID NO 17
<211> LENGTH: 6748
<212> TYPE: DNA
<213> ORGANISM: Artificial
<220> FEATURE:
<223> OTHER INFORMATION: synthetic plasmid sequence

<400> SEQUENCE: 17
aattcctcca ttttcttctg ctatcaaaat aacagactcg tgattttcca aacgagcttt      60
caaaaaagcc tctgcccctt gcaaatcgga tgcctgtcta taaaattccc gatattggct     120
taaacagcgg cgcaatggcg gccgcatctg atgtctttgc ttggcgaatg ttcatcttat     180
ttcttcctcc ctctcaataa tttttttcatt ctatcccttt tctgtaaagt ttatttttca     240
gaatactttt atcatcatgc tttgaaaaaa tatcacgata atatccattg ttctcacgga     300
agcacacgca ggtcatttga acgaattttt tcgacaggaa tttgccggga ctcaggagca     360
tttaacctaa aaaagcatga catttcagca taatgaacat ttactcatgt ctattttcgt     420
tcttttctgt atgaaaatag ttatttcgag tctctacgga aatagcgaga gatgatatac     480
ctaaatagag ataaaatcat ctcaaaaaaa tgggtctact aaaatattat tccatctatt     540
acaataaatt cacagaatag tcttttaagt aagtctactc tgaattttt taaaaggaga     600 gggtaaagag tgagaagcaa aaaattgtgg atcgtcgcgt cgaccgcact actcatttct     660 gttgcttta gttcatcgat cgcatcggct gctgaagaag caaagaaaa atatttaatt     720 ggctttaatg agcaggaagc tgtcagtgag tttgtagaac aagtagaggc aaatgacgag     780
gtcgccattc tctctgagga agaggaagtc gaaattgaat tgcttcatga atttgaaacg     840
attcctgttt tatccgttga gttaagccca gaagatgtgg acgcgcttga actcgatcca     900
gcgatttctt atattgaaga ggatgcagaa gtaacgacaa tggcgcaatc ggtaccatgg     960
ggaattagcc gtgtgcaagc cccagctgcc cataaccgtg gattgacagg ttctggtgta    1020
aaagttgctg tcctcgatac aggtatttcc actcatccag acttaaatat tcgtggtggc    1080
gctagctttg taccagggga accatccact caagatggga atgggcatgg cacgcatgtg    1140
gctgggacga ttgctgcttt aaacaattcg attggcgttc ttggcgtagc accgaacgcg    1200
gaactatacg ctgttaaagt attagggcg agcggttcag gttcggtcag ctcgattgcc    1260
caaggattgg aatgggcagg gaacaatgtt atgcacgttg ctaatttgag tttaggactg    1320
caggcaccaa gtgccacact tgagcaagct gttaatagcg cgacttctag aggcgttctt    1380
gttgtagcgg catctgggaa ttcaggtgca ggctcaatca gctatccggc ccgttatgcg    1440
aacgcaatgg cagtcggagc tactgaccaa aacaacaacc gcgccagctt ttcacagtat    1500
ggcgcagggc ttgacattgt cgcaccaggt gtaaacgtgc agagcacata cccaggttca    1560
acgtatgcca gcttaaacgg tacatcgatg ctactcctc atgttgcagg tgcagcagcc    1620
cttgttaaac aaaagaaccc atcttggtcc aatgtacaaa tccgcaatca tctaaagaat    1680
acggcaacga gcttaggaag cacgaacttg tatggaagcg gacttgtcaa tgcagaagcg    1740
gcaacacgtt aatcaataaa aaaacgctgt gcggttaaag ggcacagcgt ttttttgtgt    1800
atgaatcggg atcctcgatc gagactagag tcgatttta caagaattag ctttatataa    1860
tttctgtttt tctaaagttt tatcagctac aaaagacaga aatgtattgc aatcttcaac    1920
```

```
taaatccatt tgattctctc caatatgacg tttaataaat ttctgaaata cttgatttct   1980
ttgttttttc tcagtatact tttccatgtt ataacacata aaaacaactt agttttcaca   2040
aactatgaca ataaaaaaag ttgcttttc cccttctat gtatgttttt tactagtcat     2100
ttaaaacgat acattaatag gtacgaaaaa gcaactttt ttgcgcttaa aaccagtcat    2160
accaataact aagggtaac tagcctcgcc ggcaatagtt acccttatta tcaagataag    2220
aaagaaaagg attttcgct acgctcaaat cctttaaaaa aacacaaaag accacatttt    2280
ttaatgtggt ctttattctt caactaaagc acccattagt tcaacaaacg aaaattggat   2340
aaagtgggat attttaaaa tatatattta tgttacagta atattgactt ttaaaaagg     2400 attgattcta atgaagaaag cagacaagta agcctcctaa attcactta gataaaaatt    2460 taggaggcat atcaaatgaa ctttaataaa attgatttag acaattggaa gagaaaagag   2520
atatttaatc attatttgaa ccaacaaacg acttttagta taaccacaga aattgatatt   2580
agtgttttat accgaaacat aaaacaagaa ggatataaat tttaccctgc atttattttc   2640
ttagtgacaa gggtgataaa ctcaaataca gcttttagaa ctggttacaa tagcgacgga   2700
gagttaggtt attgggataa gttagagcca ctttatacaa tttttgatgg tgtatctaaa   2760
acattctctg gtatttggac tcctgtaaag aatgacttca aagagtttta tgatttatac   2820
ctttctgatg tagagaaata taatggttcg gggaaattgt ttcccaaaac acctatacct   2880
gaaaatgctt tttctctttc tattattcca tggacttcat ttactgggtt taacttaaat   2940
atcaataata atagtaatta ccttctaccc attattacag caggaaaatt cattaataaa   3000
ggtaattcaa tatatttacc gctatcttta caggtacatc attctgtttg tgatggttat   3060
catgcaggat tgtttatgaa ctctattcag gaattgtcag ataggcctaa tgactggctt   3120
ttataatatg agataatgcc gactgtactt tttacagtcg gttttctaat gtcactaacc   3180
tgccccgtta gttgaagaag gtttttatat tacagctcca gatccatatc cttcttttc    3240 tgaaccgact tctccttttt cgcttcttta ttccaattgc tttattgacg ttgagcctcg   3300
gaacccttaa caatcccaaa acttgtcgaa tggtcggctt aatagctcac gctatgccga   3360
cattcgtctg caagtttagt taagggttct tctcaacgca caataaattt tctcggcata   3420
aatgcgtggt ctaattttta ttttaataa ccttgatagc aaaaaatgcc attccaatac    3480
aaaaccacat acctataatc gacctgcagg aattaattcc tccattttct tctgctatca   3540
aaataacaga ctcgtgattt tccaaacgag cttcaaaaa agcctctgcc ccttgcaaat    3600
cggatgcctg tctataaaat tcccgatatt ggcttaaaca gcggcgcaat ggcggccgca   3660
tctgatgtct ttgcttggcg aatgttcatc ttatttcttc ctccctctca ataattttt    3720 cattctatcc cttttctgta aagtttattt ttcagaatac ttttatcatc atgctttgaa   3780
aaaatatcac gataatatcc attgttctca cggaagcaca cgcaggtcat ttgaacgaat   3840
tttttcgaca ggaatttgcc gggactcagg agcatttaac ctaaaaagc atgacatttc    3900 agcataatga acatttactc atgtctattt tcgttctttt ctgtatgaaa atagttattt    3960
cgagtctcta cggaaatagc gagagatgat atacctaaat agagataaaa tcatctcaaa   4020
aaaatgggtc tactaaaata ttattccatc tattacaata aattcacaga atagtctttt   4080
aagtaagtct actctgaatt tttttatcaa gctagcttgg cgtaatcatg gtcatagctg    4140
tttcctgtgt gaaattgtta tccgctcaca attccacaca acatacgagc cggaagcata   4200
aagtgtaaag cctggggtgc ctaatgagtg agctaactca cattaattgc gttgcgctca   4260
```

```
ctgcccgctt tccagtcggg aaacctgtcg tgccagctgc attaatgaat cggccaacgc    4320
gcggggagag gcggtttgcg tattgggcgc tcttccgctt cctcgctcac tgactcgctg    4380
cgctcggtcg ttcggctgcg gcgagcggta tcagctcact caaaggcggt aatacggtta    4440
tccacagaat caggggataa cgcaggaaag aacatgtgag caaaaggcca gcaaaaggcc    4500
aggaaccgta aaaaggccgc gttgctggcg ttttccata ggctccgccc ccctgacgag    4560
catcacaaaa atcgacgctc aagtcagagg tggcgaaacc cgacaggact ataaagatac    4620
caggcgtttc cccctggaag ctccctcgtg cgctctcctg ttccgaccct gccgcttacc    4680
ggatacctgt ccgcctttct cccttcggga agcgtggcgc tttctcatag ctcacgctgt    4740
aggtatctca gttcggtgta ggtcgttcgc tccaagctgg gctgtgtgca cgaaccccc    4800 gttcagcccg accgctgcgc cttatccggt aactatcgtc ttgagtccaa cccggtaaga    4860
cacgacttat cgccactggc agcagccact ggtaacagga ttagcagagc gaggtatgta    4920
ggcggtgcta cagagttctt gaagtggtgg cctaactacg gctacactag aaggacagta    4980
tttggtatct gcgctctgct gaagccagtt accttcggaa aaagagttgg tagctcttga    5040
tccggcaaac aaaccaccgc tggtagcggt ggttttttg tttgcaagca gcagattacg    5100
cgcagaaaaa aaggatctca agaagatcct ttgatctttt ctacggggtc tgacgctcag    5160
tggaacgaaa actcacgtta agggattttg gtcatgagat tatcaaaaag gatcttcacc    5220
tagatccttt taaattaaaa atgaagtttt aaatcaatct aaagtatata tgagtaaact    5280
tggtctgaca gttaccaatg cttaatcagt gaggcaccta tctcagcgat ctgtctattt    5340
cgttcatcca tagttgcctg actccccgtc gtgtagataa ctacgatacg ggagggctta    5400
ccatctggcc ccagtgctgc aatgataccg cgagacccac gctcaccggc tccagattta    5460
tcagcaataa accagccagc cggaagggcc gagcgcagaa gtggtcctgc aactttatcc    5520
gcctccatcc agtctattaa ttgttgccgg gaagctagag taagtagttc gccagttaat    5580
agtttgcgca acgttgttgc cattgctaca ggcatcgtgg tgtcacgctc gtcgtttggt    5640
atggcttcat tcagctccgg ttcccaacga tcaaggcgag ttacatgatc ccccatgttg    5700
tgcaaaaaag cggttagctc cttcggtcct ccgatcgttg tcagaagtaa gttggccgca    5760
gtgttatcac tcatggttat ggcagcactg cataattctc ttactgtcat gccatccgta    5820
agatgctttt ctgtgactgg tgagtactca accaagtcat tctgagaata gtgtatgcgg    5880
cgaccgagtt gctcttgccc ggcgtcaata cgggataata ccgcgccaca tagcagaact    5940
ttaaaagtgc tcatcattgg aaaacgttct cggggcgaa aactctcaag gatcttaccg    6000
ctgttgagat ccagttcgat gtaacccact cgtgcaccca actgatcttc agcatctttt    6060
actttcacca gcgtttctgg gtgagcaaaa acaggaaggc aaaatgccgc aaaaaaggga    6120
ataagggcga cacggaaatg ttgaatactc atactcttcc tttttcaata ttattgaagc    6180
atttatcagg gttattgtct catgagcgga tacatatttg aatgtattta gaaaaataaa    6240
caaatagggg ttccgcgcac atttccccga aaagtgccac ctgacgtcta agaaaccatt    6300
attatcatga cattaaccta taaaaatagg cgtatcacga ggccctttcg tctcgcgcgt    6360
ttcggtgatg acggtgaaaa cctctgacac atgcagctcc cggagacggt cacagcttgt    6420
ctgtaagcgg atgccgggag cagacaagcc cgtcagggcg cgtcagcggg tgttggcggg    6480
tgtcggggct ggcttaacta tgcggcatca gagcagattg tactgagagt gcaccatatg    6540
cggtgtgaaa taccgcacag atgcgtaagg agaaaatacc gcatcaggcg ccattcgcca    6600
ttcaggctgc gcaactgttg ggaagggcga tcggtgcggg cctcttcgct attacgccag    6660
```

```
ctggcgaaag ggggatgtgc tgcaaggcga ttaagttggg taacgccagg gttttcccag      6720
tcacgacgtt gtaaaacgac ggccagtg                                        6748
```

<210> SEQ ID NO 18
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 18

```
ttaaaaggag agggtaaaga nnsagaagca aaaaattgtg                             40
```

<210> SEQ ID NO 19
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 19

```
ggagagggta aagagtgnns agcaaaaaat tgtggatc                               38
```

<210> SEQ ID NO 20
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 20

```
gagggtaaag agtgaganns aaaaaattgt ggatcgtc                               38
```

<210> SEQ ID NO 21
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 21

```
ggtaaagagt gagaagcnns aaattgtgga tcgtcgc                                37
```

<210> SEQ ID NO 22
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)

<223> OTHER INFORMATION: n is a, c, g, or t

<400> SEQUENCE: 22
gtaaagagtg agaagcaaan nsttgtggat cgtcgcgtc                                    39

<210> SEQ ID NO 23
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 23
gagtgagaag caaaaaanns tggatcgtcg cgtcgac                                      37

<210> SEQ ID NO 24
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 24
gtgagaagca aaaaattgnn satcgtcgcg tcgaccgc                                     38

<210> SEQ ID NO 25
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 25
gaagcaaaaa attgtggnns gtcgcgtcga ccgcactac                                    39

<210> SEQ ID NO 26
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 26
gcaaaaaatt gtggatcnns gcgtcgaccg cactactc                                     38

<210> SEQ ID NO 27
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 27
caaaaaattg tggatcgtcn nstcgaccgc actactcatt tc                42

<210> SEQ ID NO 28
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 28
aaaaattgtg gatcgtcgcg nnsaccgcac tactcatttc                  40

<210> SEQ ID NO 29
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 29
aattgtggat cgtcgcgtcg nnsgcactac tcatttctgt tg               42

<210> SEQ ID NO 30
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 30
ggatcgtcgc gtcgaccnns ctactcattt ctgttgc                     37

<210> SEQ ID NO 31
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 31
gatcgtcgcg tcgaccgcan nsctcatttc tgttgctttt ag               42

<210> SEQ ID NO 32
<211> LENGTH: 38
<212> TYPE: DNA
<213> ORGANISM: Artificial
<220> FEATURE:
<223> OTHER INFORMATION: synthetic primer
<220> FEATURE:

<221> NAME/KEY: misc_feature
<222> LOCATION: (19)..(20)
<223> OTHER INFORMATION: n is a, c, g, or t

<400> SEQUENCE: 32
gtcgcgtcga ccgcactann satttctgtt gcttttag        38

<210> SEQ ID NO 33
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 33
cgtcgaccgc actactcnns tctgttgctt ttagttc         37

<210> SEQ ID NO 34
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 34
cgaccgcact actcattnns gttgcttta gttcatc          37

<210> SEQ ID NO 35
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 35
ccgcactact catttctnns gcttttagtt catcgatc        38

<210> SEQ ID NO 36
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 36
cactactcat ttctgttnns tttagttcat cgatcgc         37

<210> SEQ ID NO 37
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 37
ctactcattt ctgttgctnn sagttcatcg atcgcatc                              38

<210> SEQ ID NO 38
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 38
ctcatttctg ttgcttttnn stcatcgatc gcatcggc                              38

<210> SEQ ID NO 39
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 39
catttctgtt gcttttagtn nstcgatcgc atcggctgc                             39

<210> SEQ ID NO 40
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 40
ctgttgcttt tagttcanns atcgcatcgg ctgctgaag                             39

<210> SEQ ID NO 41
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 41
gttgctttta gttcatcgnn sgcatcggct gctgaagaag                            40

<210> SEQ ID NO 42
<211> LENGTH: 37
<212> TYPE: DNA
<213> ORGANISM: Artificial
<220> FEATURE:

```
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 42
cttttagttc atcgatcnns tcggctgctg aagaagc                    37

<210> SEQ ID NO 43
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 43
cttttagttc atcgatcgca nnsgctgctg aagaagcaaa ag              42

<210> SEQ ID NO 44
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 44
gttcatcgat cgcatcgnns gctgaagaag caaaagaaaa                 40

<210> SEQ ID NO 45
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 45
catcgatcgc atcggctnns gaagaagcaa aagaaaaata                 40

<210> SEQ ID NO 46
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 46
cgatcgcatc ggctgctnns gaagcaaaag aaaaatattt                 40

<210> SEQ ID NO 47
<211> LENGTH: 42
<212> TYPE: DNA
<213> ORGANISM: Artificial
```

```
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 47
gatcgcatcg gctgctgaan nsgcaaaaga aaaatattta at          42

<210> SEQ ID NO 48
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 48
catcggctgc tgaagaanns aaagaaaaat atttaattg              39

<210> SEQ ID NO 49
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 49
cggctgctga agaagcanns gaaaaatatt taattgg                37

<210> SEQ ID NO 50
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 50
ctgctgaaga agcaaaanns aaatatttaa ttggctttaa             40

<210> SEQ ID NO 51
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 51
ctgaagaagc aaaagaanns tatttaattg gctttaatg              39

<210> SEQ ID NO 52
<211> LENGTH: 39
<212> TYPE: DNA
```

<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 52
gaagaagcaa aagaaaaann sttaattggc tttaatgag       39

<210> SEQ ID NO 53
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 53
gaagcaaaag aaaaatatnn sattggcttt aatgagcag       39

<210> SEQ ID NO 54
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 54
caaaagaaaa atatttanns ggctttaatg agcaggaag       39

<210> SEQ ID NO 55
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 55
caaaagaaaa atatttaatt nnstttaatg agcaggaagc      40

<210> SEQ ID NO 56
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 56 gaaaatatt taattggcnn saatgagcag gaagctgtc        39

<210> SEQ ID NO 57
<211> LENGTH: 40

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 57
aaaaatattt aattggcttt nnsgagcagg aagctgtcag                              40

<210> SEQ ID NO 58
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 58
aatatttaat tggctttaat nnscaggaag ctgtcagtga g                            41

<210> SEQ ID NO 59
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 59
atttaattgg ctttaatgag nnsgaagctg tcagtgagtt tg                           42

<210> SEQ ID NO 60
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 60
taattggctt taatgagcag nnsgctgtca gtgagtttgt ag                           42

<210> SEQ ID NO 61
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 61
gctttaatga gcaggaanns gtcagtgagt ttgtagaac                               39

<210> SEQ ID NO 62
```

```
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 62
ctttaatgag caggaagctn nsagtgagtt tgtagaacaa g                41

<210> SEQ ID NO 63
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 63
ttaatgagca ggaagctgtc nnsgagtttg tagaacaagt ag               42

<210> SEQ ID NO 64
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 64
gagcaggaag ctgtcagtnn stttgtagaa caagtagag                   39

<210> SEQ ID NO 65
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 65
caggaagctg tcagtgagnn sgtagaacaa gtagaggc                    38

<210> SEQ ID NO 66
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 66
gaagctgtca gtgagtttnn sgaacaagta gaggcaaatg                  40
```

```
<210> SEQ ID NO 67
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 67
ctgtcagtga gtttgtanns caagtagagg caaatgac                       38

<210> SEQ ID NO 68
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 68
gtcagtgagt ttgtagaann sgtagaggca aatgacgag                      39

<210> SEQ ID NO 69
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 69
gtgagtttgt agaacaanns gaggcaaatg acgaggtc                       38

<210> SEQ ID NO 70
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 70
gagtttgtag aacaagtann sgcaaatgac gaggtcgc                       38

<210> SEQ ID NO 71
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 71
gtttgtagaa caagtagagn nsaatgacga ggtcgccatt c                   41
```

```
<210> SEQ ID NO 72
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 72
gtagaacaag tagaggcann sgacgaggtc gccattctc                              39

<210> SEQ ID NO 73
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 73
gaacaagtag aggcaaatnn sgaggtcgcc attctctc                               38

<210> SEQ ID NO 74
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 74
caagtagagg caaatgacnn sgtcgccatt ctctctgag                              39

<210> SEQ ID NO 75
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 75
gtagaggcaa atgacgagnn sgccattctc tctgaggaag                             40

<210> SEQ ID NO 76
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 76
gaggcaaatg acgaggtcnn sattctctct gaggaagag                              39
```

<210> SEQ ID NO 77
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 77
caaatgacga ggtcgccnns ctctctgagg aagaggaag                39

<210> SEQ ID NO 78
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 78
caaatgacga ggtcgccatt nnstctgagg aagaggaagt c             41

<210> SEQ ID NO 79
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 79
gacgaggtcg ccattctcnn sgaggaagag gaagtcgaaa t             41

<210> SEQ ID NO 80
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 80
gaggtcgcca ttctctctnn sgaagaggaa gtcgaaattg               40

<210> SEQ ID NO 81
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 81

-continued gtcgccattc tctctgagnn sgaggaagtc gaaattgaat t          41

<210> SEQ ID NO 82
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 82
ccattctctc tgaggaanns gaagtcgaaa ttgaattg          38

<210> SEQ ID NO 83
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 83
cattctctct gaggaagagn nsgtcgaaat tgaattgctt c          41

<210> SEQ ID NO 84
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 84
ctctctgagg aagaggaann sgaaattgaa ttgcttcatg          40

<210> SEQ ID NO 85
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 85
ctgaggaaga ggaagtcnns attgaattgc ttcatgaatt          40

<210> SEQ ID NO 86
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 86
gaggaagagg aagtcgaann sgaattgctt catgaatttg        40

<210> SEQ ID NO 87
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 87
gaagaggaag tcgaaattnn sttgcttcat gaatttgaaa c        41

<210> SEQ ID NO 88
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 88
gaggaagtcg aaattgaann scttcatgaa tttgaaac        38

<210> SEQ ID NO 89
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 89
gaagtcgaaa ttgaattgnn scatgaattt gaaacgattc        40

<210> SEQ ID NO 90
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 90
gtcgaaattg aattgcttnn sgaatttgaa acgattcc        38

<210> SEQ ID NO 91
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 91
gaaattgaat tgcttcatnn stttgaaacg attcctgttt t                          41

<210> SEQ ID NO 92
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 92
aaattgaatt gcttcatgaa nnsgaaacga ttcctgtttt atc                        43

<210> SEQ ID NO 93
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 93
gaattgcttc atgaatttnn sacgattcct gttttatc                              38

<210> SEQ ID NO 94
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 94
aattgcttca tgaatttgaa nnsattcctg ttttatccgt tg                         42

<210> SEQ ID NO 95
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 95
cttcatgaat ttgaaacgnn scctgtttta tccgttgag                             39

<210> SEQ ID NO 96
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

```
<400> SEQUENCE: 96
catgaatttg aaacgattnn sgttttatcc gttgagttaa g                         41

<210> SEQ ID NO 97
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 97
gaatttgaaa cgattcctnn sttatccgtt gagttaag                             38

<210> SEQ ID NO 98
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 98
aatttgaaac gattcctgtt nnstccgttg agttaagccc                           40

<210> SEQ ID NO 99
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 99
gaaacgattc ctgttttann sgttgagtta agcccagaag                           40

<210> SEQ ID NO 100
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 100
cgattcctgt tttatccnns gagttaagcc cagaagatg                            39

<210> SEQ ID NO 101
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
```

```
<223> OTHER INFORMATION: n is a, c, g, or t

<400> SEQUENCE: 101
gattcctgtt ttatccgttn nsttaagccc agaagatgtg                                    40

<210> SEQ ID NO 102
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 102
ctgttttatc cgttgagnns agcccagaag atgtggac                                      38

<210> SEQ ID NO 103
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 103
gttttatccg ttgagttann sccagaagat gtggacgc                                      38

<210> SEQ ID NO 104
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 104
ttttatccgt tgagttaagc nnsgaagatg tggacgcgct tg                                  42

<210> SEQ ID NO 105
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 105
ccgttgagtt aagcccanns gatgtggacg cgcttgaac                                     39

<210> SEQ ID NO 106
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
```

```
<222> LOCATION: (19)..(20)
<223> OTHER INFORMATION: n is a, c, g, or t

<400> SEQUENCE: 106
gttgagttaa gcccagaann sgtggacgcg cttgaactc                    39

<210> SEQ ID NO 107
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 107
gagttaagcc cagaagatnn sgacgcgctt gaactcgatc                   40

<210> SEQ ID NO 108
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 108
gttaagccca gaagatgtgn nsgcgcttga actcgatcc                    39

<210> SEQ ID NO 109
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 109
gcccagaaga tgtggacnns cttgaactcg atccagc                      37

<210> SEQ ID NO 110
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 110
cagaagatgt ggacgcgnns gaactcgatc cagcgatttc                   40

<210> SEQ ID NO 111
<211> LENGTH: 38
<212> TYPE: DNA
<213> ORGANISM: Artificial
<220> FEATURE:
<223> OTHER INFORMATION: synthetic primer
<220> FEATURE:
```

<221> NAME/KEY: misc_feature
<222> LOCATION: (19)..(20)
<223> OTHER INFORMATION: n is a, c, g, or t

<400> SEQUENCE: 111
gaagatgtgg acgcgcttnn sctcgatcca gcgatttc                                38

<210> SEQ ID NO 112
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 112
gatgtggacg cgcttgaann sgatccagcg atttcttata t                            41

<210> SEQ ID NO 113
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 113
gtggacgcgc ttgaactcnn sccagcgatt tcttatattg                              40

<210> SEQ ID NO 114
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 114
gacgcgcttg aactcgatnn sgcgatttct tatattgaag                              40

<210> SEQ ID NO 115
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 115
cgcttgaact cgatccanns atttcttata ttgaagag                                38

<210> SEQ ID NO 116
<211> LENGTH: 40
<212> TYPE: DNA
<213> ORGANISM: Artificial
<220> FEATURE:
<223> OTHER INFORMATION: synthetic primer

```
<220> FEATURE:
<221> NAME/KEY: misc_feature
<222> LOCATION: (19)..(20)
<223> OTHER INFORMATION: n is a, c, g, or t

<400> SEQUENCE: 116
cttgaactcg atccagcgnn stcttatatt gaagaggatg                                    40

<210> SEQ ID NO 117
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 117
gaactcgatc cagcgattnn statattgaa gaggatgc                                      38

<210> SEQ ID NO 118
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 118
ctcgatccag cgatttctnn sattgaagag gatgcagaag                                    40

<210> SEQ ID NO 119
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 119
gatccagcga tttcttatnn sgaagaggat gcagaagtaa c                                  41

<210> SEQ ID NO 120
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 120
cagcgatttc ttatattnns gaggatgcag aagtaac                                       37

<210> SEQ ID NO 121
<211> LENGTH: 37
<212> TYPE: DNA
<213> ORGANISM: Artificial
<220> FEATURE:
```

<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 121
cgatttctta tattgaanns gatgcagaag taacgac                37

<210> SEQ ID NO 122
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 122
gatttcttat attgaagagn nsgcagaagt aacgacaatg             40

<210> SEQ ID NO 123
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (18)..(19)
<223> OTHER INFORMATION: n is a, c, g, or t

<400> SEQUENCE: 123
cttatattga agaggatnns gaagtaacga caatggc                37

<210> SEQ ID NO 124
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 124
cttatattga agaggatgca nnsgtaacga caatggcgca atc         43

<210> SEQ ID NO 125
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 125
atattgaaga ggatgcagaa nnsacgacaa tggcgcaatc             40

<210> SEQ ID NO 126
<211> LENGTH: 40
<212> TYPE: DNA
<213> ORGANISM: Artificial

<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 126
gaagaggatg cagaagtann sacaatggcg caatcggtac                    40

<210> SEQ ID NO 127
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 127
gaggatgcag aagtaacgnn satggcgcaa tcggtacc                      38

<210> SEQ ID NO 128
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 128
gatgcagaag taacgacann sgcgcaatcg gtaccatg                      38

<210> SEQ ID NO 129
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 129
cacaattttt tgcttctsnn tctttaccct ctccttttaa                    40

<210> SEQ ID NO 130
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 130
gatccacaat tttttgctsn ncactcttta ccctctcc                      38

<210> SEQ ID NO 131
<211> LENGTH: 38
<212> TYPE: DNA

<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 131
gacgatccac aattttttsn ntctcactct ttaccctc        38

<210> SEQ ID NO 132
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 132
gcgacgatcc acaatttsnn gcttctcact ctttacc        37

<210> SEQ ID NO 133
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 133
gacgcgacga tccacaasnn tttgcttctc actctttac        39

<210> SEQ ID NO 134
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 134
gtcgacgcga cgatccasnn tttttgctt ctcactc        37

<210> SEQ ID NO 135
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 135
gcggtcgacg cgacgatsnn caatttttg cttctcac        38

<210> SEQ ID NO 136
<211> LENGTH: 39

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 136
gtagtgcggt cgacgcgacs nnccacaatt ttttgcttc                             39

<210> SEQ ID NO 137
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 137
gagtagtgcg gtcgacgcsn ngatccacaa ttttttgc                              38

<210> SEQ ID NO 138
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 138
gaaatgagta gtgcggtcga snngacgatc cacaattttt tg                         42

<210> SEQ ID NO 139
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 139
gaaatgagta gtgcggtsnn cgcgacgatc cacaattttt                            40

<210> SEQ ID NO 140
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 140
caacagaaat gagtagtgcs nncgacgcga cgatccacaa tt                         42

<210> SEQ ID NO 141
```

```
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 141
gcaacagaaa tgagtagsnn ggtcgacgcg acgatcc                           37

<210> SEQ ID NO 142
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 142
ctaaaagcaa cagaaatgag snntgcggtc gacgcgacga tc                     42

<210> SEQ ID NO 143
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 143
ctaaaagcaa cagaaatsnn tagtgcggtc gacgcgac                          38

<210> SEQ ID NO 144
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 144
gaactaaaag caacagasnn gagtagtgcg gtcgacg                           37

<210> SEQ ID NO 145
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 145
gatgaactaa aagcaacsnn aatgagtagt gcggtcg                           37
```

```
<210> SEQ ID NO 146
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 146
gatcgatgaa ctaaaagcsn nagaaatgag tagtgcgg                                  38

<210> SEQ ID NO 147
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 147
gcgatcgatg aactaaasnn aacagaaatg agtagtg                                   37

<210> SEQ ID NO 148
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 148
gatgcgatcg atgaactsnn agcaacagaa atgagtag                                  38

<210> SEQ ID NO 149
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 149
gccgatgcga tcgatgasnn aaaagcaaca gaaatgag                                  38

<210> SEQ ID NO 150
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 150
gcagccgatg cgatcgasnn actaaaagca acagaaatg                                 39
```

```
<210> SEQ ID NO 151
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 151
cttcagcagc cgatgcgats nntgaactaa aagcaacag                              39

<210> SEQ ID NO 152
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 152
cttcttcagc agccgatgcs nncgatgaac taaaagcaac                             40

<210> SEQ ID NO 153
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 153
gcttcttcag cagccgasnn gatcgatgaa ctaaaag                                37

<210> SEQ ID NO 154
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 154
cttttgcttc ttcagcagcs nntgcgatcg atgaactaaa ag                          42

<210> SEQ ID NO 155
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 155
ttttcttttg cttcttcagc snncgatgcg atcgatgaac                             40
```

<210> SEQ ID NO 156
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 156 tattttctt ttgcttcttc snnagccgat gcgatcgatg                    40

<210> SEQ ID NO 157
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 157
aaatattttt cttttgcttc snnagcagcc gatgcgatcg                    40

<210> SEQ ID NO 158
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 158
attaaatatt tttcttttgc snnttcagca gccgatgcga tc                 42

<210> SEQ ID NO 159
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 159
caattaaata tttttcttts nnttcttcag cagccgatg                     39

<210> SEQ ID NO 160
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 160

```
ccaattaaat attttcsnn tgcttcttca gcagccg                              37
```

<210> SEQ ID NO 161
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 161

```
ttaaagccaa ttaaatattt snnttttgct tcttcagcag                          40
```

<210> SEQ ID NO 162
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 162

```
cattaaagcc aattaaatas nnttcttttg cttcttcag                           39
```

<210> SEQ ID NO 163
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 163

```
ctcattaaag ccaattaasn nttttctttt tgcttcttc                           39
```

<210> SEQ ID NO 164
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 164

```
ctgctcatta aagccaatsn natattttc ttttgcttc                            39
```

<210> SEQ ID NO 165
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 165
cttcctgctc attaaagccs nntaaatatt tttcttttg                                39

<210> SEQ ID NO 166
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 166
gcttcctgct cattaaasnn aattaaatat ttttcttttg                                40

<210> SEQ ID NO 167
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 167
gacagcttcc tgctcattsn ngccaattaa atattttc                                 39

<210> SEQ ID NO 168
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 168
ctgacagctt cctgctcsnn aaagccaatt aaatattttt                                40

<210> SEQ ID NO 169
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 169
ctcactgaca gcttcctgsn nattaaagcc aattaaatat t                              41

<210> SEQ ID NO 170
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 170
caaactcact gacagcttcs nnctcattaa agccaattaa at                              42

<210> SEQ ID NO 171
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 171
ctacaaactc actgacagcs nnctgctcat taaagccaat ta                              42

<210> SEQ ID NO 172
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 172
gttctacaaa ctcactgacs nnttcctgct cattaaagc                                  39

<210> SEQ ID NO 173
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 173
cttgttctac aaactcacts nnagcttcct gctcattaaa g                               41

<210> SEQ ID NO 174
<211> LENGTH: 42
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 174
ctacttgttc tacaaactcs nngacagctt cctgctcatt aa                              42

<210> SEQ ID NO 175
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 175
ctctacttgt tctacaaasn nactgacagc ttcctgctc                                    39

<210> SEQ ID NO 176
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 176
gcctctactt gttctacsnn ctcactgaca gcttcctg                                     38

<210> SEQ ID NO 177
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 177
catttgcctc tacttgttcs nnaaactcac tgacagcttc                                   40

<210> SEQ ID NO 178
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 178
gtcatttgcc tctacttgsn ntacaaactc actgacag                                     38

<210> SEQ ID NO 179
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 179
ctcgtcattt gcctctacsn nttctacaaa ctcactgac                                    39

<210> SEQ ID NO 180
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)

<223> OTHER INFORMATION: n is a, c, g, or t

<400> SEQUENCE: 180
gacctcgtca tttgcctcsn nttgttctac aaactcac                                    38

<210> SEQ ID NO 181
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 181
gcgacctcgt catttgcsnn tacttgttct acaaactc                                    38

<210> SEQ ID NO 182
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 182
gaatggcgac ctcgtcatts nnctctactt gttctacaaa c                                41

<210> SEQ ID NO 183
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 183
gagaatggcg acctcgtcsn ntgcctctac ttgttctac                                   39

<210> SEQ ID NO 184
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 184
gagagaatgg cgacctcsnn atttgcctct acttgttc                                    38

<210> SEQ ID NO 185
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 185
ctcagagaga atggcgacsn ngtcatttgc ctctacttg          39

<210> SEQ ID NO 186
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 186
cttcctcaga gagaatggcs nnctcgtcat ttgcctctac          40

<210> SEQ ID NO 187
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 187
ctcttcctca gagagaatsn ngacctcgtc atttgcctc          39

<210> SEQ ID NO 188
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 188
cttcctcttc ctcagagags nnggcgacct cgtcatttg          39

<210> SEQ ID NO 189
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 189
gacttcctct tcctcagasn naatggcgac ctcgtcattt g          41

<210> SEQ ID NO 190
<211> LENGTH: 41
<212> TYPE: DNA
<213> ORGANISM: Artificial
<220> FEATURE:
<223> OTHER INFORMATION: synthetic primer
<220> FEATURE:

<221> NAME/KEY: misc_feature
<222> LOCATION: (22)..(23)
<223> OTHER INFORMATION: n is a, c, g, or t

<400> SEQUENCE: 190
atttcgactt cctcttcctc snngagaatg gcgacctcgt c        41

<210> SEQ ID NO 191
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 191
caatttcgac ttcctcttcs nnagagagaa tggcgacctc          40

<210> SEQ ID NO 192
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 192
aattcaattt cgacttcctc snnctcagag agaatggcga c        41

<210> SEQ ID NO 193
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 193
caattcaatt tcgacttcsn nttcctcaga gagaatgg            38

<210> SEQ ID NO 194
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 194
gaagcaattc aatttcgacs nnctcttcct cagagagaat g        41

<210> SEQ ID NO 195
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 195
catgaagcaa ttcaatttcs nnttcctctt cctcagagag          40

<210> SEQ ID NO 196
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 196
aattcatgaa gcaattcaat snngacttcc tcttcctcag          40

<210> SEQ ID NO 197
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 197
caaattcatg aagcaattcs nnttcgactt cctcttcctc          40

<210> SEQ ID NO 198
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 198
gtttcaaatt catgaagcaa snnaatttcg acttcctctt c          41

<210> SEQ ID NO 199
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 199
gtttcaaatt catgaagsnn ttcaatttcg acttcctc          38

<210> SEQ ID NO 200
<211> LENGTH: 40
<212> TYPE: DNA
<213> ORGANISM: Artificial
<220> FEATURE:

<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 200
gaatcgtttc aaattcatgs nncaattcaa tttcgacttc                                40

<210> SEQ ID NO 201
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 201
ggaatcgttt caaattcsnn aagcaattca atttcgac                                 38

<210> SEQ ID NO 202
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 202
aaaacaggaa tcgtttcaaa snnatgaagc aattcaattt c                             41

<210> SEQ ID NO 203
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 203
gataaaacag gaatcgtttc snnttcatga agcaattcaa ttt                           43

<210> SEQ ID NO 204
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 204
gataaaacag gaatcgtsnn aaattcatga agcaattc                                 38

<210> SEQ ID NO 205
<211> LENGTH: 42
<212> TYPE: DNA
<213> ORGANISM: Artificial

<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 205
caacggataa aacaggaats nnttcaaatt catgaagcaa tt                42

<210> SEQ ID NO 206
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 206
ctcaacggat aaaacaggsn ncgtttcaaa ttcatgaag                    39

<210> SEQ ID NO 207
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 207
cttaactcaa cggataaaac snnaatcgtt tcaaattcat g                 41

<210> SEQ ID NO 208
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 208
cttaactcaa cggataasnn aggaatcgtt tcaaattc                     38

<210> SEQ ID NO 209
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 209
gggcttaact caacggasnn aacaggaatc gtttcaaatt                   40

<210> SEQ ID NO 210
<211> LENGTH: 40
<212> TYPE: DNA

<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 210
cttctgggct taactcaacs nntaaaacag gaatcgtttc         40

<210> SEQ ID NO 211
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 211
catcttctgg gcttaactcs nnggataaaa caggaatcg         39

<210> SEQ ID NO 212
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 212
cacatcttct gggcttaasn naacggataa aacaggaatc         40

<210> SEQ ID NO 213
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 213
gtccacatct tctgggctsn nctcaacgga taaaacag         38

<210> SEQ ID NO 214
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 214
gcgtccacat cttctggsnn taactcaacg gataaaac         38

<210> SEQ ID NO 215
<211> LENGTH: 42

-continued

```
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 215
caagcgcgtc cacatcttcs nngcttaact caacggataa aa                    42

<210> SEQ ID NO 216
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 216
gttcaagcgc gtccacatcs nntgggctta actcaacgg                        39

<210> SEQ ID NO 217
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 217
gagttcaagc gcgtccacsn nttctgggct taactcaac                        39

<210> SEQ ID NO 218
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 218
gatcgagttc aagcgcgtcs nnatcttctg ggcttaactc                       40

<210> SEQ ID NO 219
<211> LENGTH: 39
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 219
ggatcgagtt caagcgcsnn cacatcttct gggcttaac                        39

<210> SEQ ID NO 220
```

```
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 220
gctggatcga gttcaagsnn gtccacatct tctgggc                               37

<210> SEQ ID NO 221
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 221
gaaatcgctg gatcgagttc snncgcgtcc acatcttctg                            40

<210> SEQ ID NO 222
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 222
gaaatcgctg gatcgagsnn aagcgcgtcc acatcttc                              38

<210> SEQ ID NO 223
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 223
atataagaaa tcgctggatc snnttcaagc gcgtccacat c                          41

<210> SEQ ID NO 224
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 224
caatataaga aatcgctggs nngagttcaa gcgcgtccac                            40
```

```
<210> SEQ ID NO 225
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 225
cttcaatata agaaatcgcs nnatcgagtt caagcgcgtc                               40

<210> SEQ ID NO 226
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 226
ctcttcaata taagaaatsn ntggatcgag ttcaagcg                                 38

<210> SEQ ID NO 227
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 227
catcctcttc aatataagas nncgctggat cgagttcaag                               40

<210> SEQ ID NO 228
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 228
gcatcctctt caatatasnn aatcgctgga tcgagttc                                 38

<210> SEQ ID NO 229
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 229
cttctgcatc ctcttcaats nnagaaatcg ctggatcgag                               40
```

<210> SEQ ID NO 230
<211> LENGTH: 41
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 230
gttacttctg catcctcttc snnataagaa atcgctggat c                            41

<210> SEQ ID NO 231
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 231
gttacttctg catcctcsnn aatataagaa atcgctg                                 37

<210> SEQ ID NO 232
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 232
gtcgttactt ctgcatcsnn ttcaatataa gaaatcg                                 37

<210> SEQ ID NO 233
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (20)..(21)
<223> OTHER INFORMATION: n is a, c, g, or t

<400> SEQUENCE: 233
cattgtcgtt acttctgcsn nctcttcaat ataagaaatc                              40

<210> SEQ ID NO 234
<211> LENGTH: 37
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 234
gccattgtcg ttacttcsnn atcctcttca atataag                                 37

<210> SEQ ID NO 235
<211> LENGTH: 43
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (22)..(23)
<223> OTHER INFORMATION: n is a, c, g, or t

<400> SEQUENCE: 235
gattgcgcca ttgtcgttac snntgcatcc tcttcaatat aag    43

<210> SEQ ID NO 236
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 236
gattgcgcca ttgtcgtsnn ttctgcatcc tcttcaatat    40

<210> SEQ ID NO 237
<211> LENGTH: 40
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (21)..(22)
<223> OTHER INFORMATION: n is a, c, g, or t

<400> SEQUENCE: 237
gtaccgattg cgccattgts nntacttctg catcctcttc    40

<210> SEQ ID NO 238
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 238
ggtaccgatt gcgccatsnn cgttacttct gcatcctc    38

<210> SEQ ID NO 239
<211> LENGTH: 38
<212> TYPE: DNA
<213> ORGANISM: Artificial
<220> FEATURE:
<223> OTHER INFORMATION: synthetic primer
<220> FEATURE:
<221> NAME/KEY: misc_feature
<222> LOCATION: (19)..(20)
<223> OTHER INFORMATION: n is a, c, g, or t

<400> SEQUENCE: 239

-continued catggtaccg attgcgcsnn tgtcgttact tctgcatc 38

<210> SEQ ID NO 240
<211> LENGTH: 1140
<212> TYPE: DNA
<213> ORGANISM: Bacillus lentus

<400> SEQUENCE: 240
gtgagaagca aaaaattgtg gatcgtcgcg tcgaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaat cagtgccatg gggaattagc 360
cgtgtgcaag ccccagctgc ccataaccgt ggattgacag gttctggtgt aaaagttgct 420
gtcctcgata caggtatttc cactcatcca gacttaaata ttcgtggtgg cgctagcttt 480
gtaccagggg aaccatccac tcaagatggg aatgggcatg gcacgcatgt ggccgggacg 540
attgctgctc taaacaattc gattggcgtt cttggcgtag cgccgagcgc ggaactatac 600
gctgttaaag tattaggggc gagcggttca ggctcggtca gctcgattgc ccaaggattg 660
gaatgggcag ggaacaatgg catgcacgtt gctaatttga gtttaggaag cccttcgcca 720
agtgccacac ttgagcaagc tgttaatagc gcgacttcta gaggcgttct tgttgtagcg 780
gcatctggaa attcaggtgc aggctcaatc agctatccgg cccgttatgc gaacgcaatg 840
gcagtcggag ctactgacca aaacaacaac cgcgccagct tttcacagta tggcgcaggg 900
cttgacattg tcgcaccagg tgtaaacgtg cagagcacat acccaggttc aacgtatgcc 960
agcttaaacg gtacatcgat ggctactcct catgttgcag gtgcagcagc ccttgttaaa 1020
caaaagaacc catcttggtc caatgtacaa atccgcaatc atctaaagaa tacggcaacg 1080
agcttaggaa gcacgaactt gtatggaagc ggacttgtca atgcagaagc tgcaactcgt 1140

<210> SEQ ID NO 241
<211> LENGTH: 81
<212> TYPE: DNA
<213> ORGANISM: Bacillus lentus

<400> SEQUENCE: 241
gtgagaagca aaaaattgtg gatcgtcgcg tcgaccgcac tactcatttc tgttgctttt 60
agttcatcga tcgcatcggc t 81

<210> SEQ ID NO 242
<211> LENGTH: 252
<212> TYPE: DNA
<213> ORGANISM: Bacillus lentus

<400> SEQUENCE: 242
gctgaagaag caaaagaaaa atatttaatt ggctttaatg agcaggaagc tgtcagtgag 60
tttgtagaac aagtagaggc aaatgacgag gtcgccattc tctctgagga agaggaagtc 120
gaaattgaat tgcttcatga atttgaaacg attcctgttt tatccgttga gttaagccca 180
gaagatgtgg acgcgcttga actcgatcca gcgatttctt atattgaaga ggatgcagaa 240
gtaacgacaa tg 252

-continued

```
<210> SEQ ID NO 243
<211> LENGTH: 809
<212> TYPE: DNA
<213> ORGANISM: Bacillus lentus

<400> SEQUENCE: 243
gcgcaatcag tgccatgggg aattagccgt gtgcaagccc cagctgccca taaccgtgga      60
ttgacaggtt ctggtgtaaa agttgctgtc ctcgatacag gtatttccac tcatccagac     120
ttaaatattc gtggtggcgc tagctttgta ccagggaaac catccactca agatgggaat     180
gggcatggca cgcatgtggc cgggacgatt gctgctctaa acaattcgat tggcgttctt     240
ggcgtagcgc cgagcgcgga actatacgct gttaaagtat taggggcgag cggttcaggc     300
tcggtcagct cgattgccca aggattggaa tgggcaggga caatggcat gcacgttgct     360 aatttgagtt taggaagccc ttcgccaagt gccacacttg agcaagctgt taatagcgcg     420
acttctagag gcgttcttgt tgtagcggca tctggaaatt caggtgcagg ctcaatcagc     480
tatccggccc gttatgcgaa cgcaatggca gtcggagcta ctgaccaaaa caacaaccgc     540
gccagctttt cacagtatgg cgcagggctt gacattgtcg caccaggtgt aaacgtgcag     600
agcacatacc caggttcaac gtatgccagc ttaaacggta tcgatggc tactcctcat     660 gttgcaggtg cagcagccct tgttaaacaa aagaacccat cttggtccaa tgtacaaatc     720
cgcaatcatc taaagaatac ggcaacgagc ttaggaagca cgaacttgta tggaagcgga     780
cttgtcaatg cagaagctgc aactcgtta                                       809

<210> SEQ ID NO 244
<211> LENGTH: 380
<212> TYPE: PRT
<213> ORGANISM: Bacillus lentus

<400> SEQUENCE: 244

Met Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190
```

```
Val Ala Pro Ser Ala Glu Leu Tyr Ala Val Lys Val Leu Gly Ala Ser
            195                 200                 205

Gly Ser Gly Ser Val Ser Ser Ile Ala Gln Gly Leu Glu Trp Ala Gly
        210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
            245                 250                 255

Leu Val Val Ala Ala Ser Gly Asn Ser Gly Ala Gly Ser Ile Ser Tyr
        260                 265                 270

Pro Ala Arg Tyr Ala Asn Ala Met Ala Val Gly Ala Thr Asp Gln Asn
            275                 280                 285

Asn Asn Arg Ala Ser Phe Ser Gln Tyr Gly Ala Gly Leu Asp Ile Val
290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
            325                 330                 335

Ala Leu Val Lys Gln Lys Asn Pro Ser Trp Ser Asn Val Gln Ile Arg
        340                 345                 350

Asn His Leu Lys Asn Thr Ala Thr Ser Leu Gly Ser Thr Asn Leu Tyr
            355                 360                 365

Gly Ser Gly Leu Val Asn Ala Glu Ala Ala Thr Arg
        370                 375                 380

<210> SEQ ID NO 245
<211> LENGTH: 27
<212> TYPE: PRT
<213> ORGANISM: Bacillus lentus

<400> SEQUENCE: 245

Met Arg Ser Lys Lys Leu Trp Ile Val Ala Ser Thr Ala Leu Leu Ile
1               5                   10                  15

Ser Val Ala Phe Ser Ser Ser Ile Ala Ser Ala
            20                  25

<210> SEQ ID NO 246
<211> LENGTH: 84
<212> TYPE: PRT
<213> ORGANISM: Bacillus lentus

<400> SEQUENCE: 246

Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met

<210> SEQ ID NO 247
<211> LENGTH: 269
<212> TYPE: PRT
```

```
<213> ORGANISM: Bacillus lentus

<400> SEQUENCE: 247

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
    195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```